(12) United States Patent
Cai et al.

(10) Patent No.: US 12,018,027 B2
(45) Date of Patent: Jun. 25, 2024

(54) MACROCYCLIC DERIVATIVES ACTING AS XIa FACTOR INHIBITOR

(71) Applicant: CHINA RESOURCES BIOPHARMACEUTICAL COMPANY LIMITED, Beijing (CN)

(72) Inventors: Yaxian Cai, Shanghai (CN); Xiaobing Yan, Shanghai (CN); Ting Wang, Shanghai (CN); Chengde Wu, Shanghai (CN); Charles Z. Ding, Shanghai (CN); Shuhui Chen, Shanghai (CN)

(73) Assignee: China Resources Biopharmaceutical Company Limited, Beijing (CN)

( * ) Notice: Subject to any disclaimer, the term of this patent is extended or adjusted under 35 U.S.C. 154(b) by 470 days.

(21) Appl. No.: 17/604,336

(22) PCT Filed: Apr. 15, 2020

(86) PCT No.: PCT/CN2020/084932
§ 371 (c)(1),
(2) Date: Oct. 15, 2021

(87) PCT Pub. No.: WO2020/211781
PCT Pub. Date: Oct. 22, 2020

(65) Prior Publication Data
US 2022/0204508 A1 Jun. 30, 2022

(30) Foreign Application Priority Data
Apr. 16, 2019 (CN) .......................... 201910303358.4
Mar. 20, 2020 (CN) .......................... 202010200778.2

(51) Int. Cl.
C07D 471/18 (2006.01)

(52) U.S. Cl.
CPC ................................ C07D 471/18 (2013.01)

(58) Field of Classification Search
CPC .................................................. C07D 471/18
USPC ...................................................... 514/293
See application file for complete search history.

(56) References Cited

FOREIGN PATENT DOCUMENTS

| CN | 105980384 A | 9/2016 |
|---|---|---|
| CN | 106459051 A | 2/2017 |
| CN | 106795161 A | 5/2017 |
| WO | 2011/100401 A1 | 8/2011 |
| WO | 2011/100402 A1 | 8/2011 |
| WO | 2013/022814 A1 | 2/2013 |
| WO | 2013/022818 A1 | 2/2013 |
| WO | 2014/022766 A1 | 2/2014 |
| WO | 2014/022767 A1 | 2/2014 |
| WO | 2015/116882 A1 | 8/2015 |
| WO | 2015/116885 A1 | 8/2015 |
| WO | 2015/116886 A1 | 8/2015 |
| WO | 2016/053455 A1 | 4/2016 |
| WO | 2017/074832 A1 | 5/2017 |
| WO | 2017/074833 A1 | 5/2017 |
| WO | 2018/133793 A1 | 7/2018 |

OTHER PUBLICATIONS

Australian Office Action for Application No. 2020257911, dated Sep. 26, 2022, 3 pages.
European Office Action for Application No. 20792125.5, dated Dec. 13, 2022, 6 pages.
Japanese Office Action for Application No. 2021-561779, dated Dec. 12, 2022, 4 pages.
International Search Report and Written Opinion for Application No. PCT/CN2020/084932, dated Jun. 30, 2020, 017 pages.
Mar. 7, 2023 First Office Action issued in Canadian Patent Application No. 3136861.
Mar. 2, 2023 First Office Action issued in Chinese Patent Application No. 202080028108.5.
Feb. 27, 2023 Search Report issued in Chinese Patent Application No. 202080028108.5.

Primary Examiner — Kristin A Vajda
(74) Attorney, Agent, or Firm — McCarter & English, LLP; Maneesh Gulati

(57) ABSTRACT

Disclosed are a class of macrocyclic derivatives, a preparation method therefor, a pharmaceutical composition containing the derivatives, and the use thereof as therapeutic agents, particularly as XIa factor inhibitors and in the preparation of a drug for treating and preventing thromboembolisms and other diseases. Particularly disclosed are compounds shown by formula (I), an isomer thereof and a pharmaceutically acceptable salt thereof.

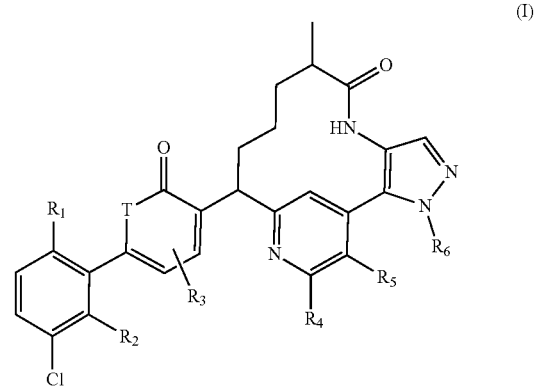

(I)

20 Claims, No Drawings

MACROCYCLIC DERIVATIVES ACTING AS XIa FACTOR INHIBITOR

RELATED APPLICATIONS

This application is a 35 U.S.C. § 371 national stage filing of International Application No. PCT/CN2020/084932, filed on Apr. 15, 2020, which in turn claims the benefit of Chinese Patent Application No. 201910303358.4, filed on Apr. 16, 2019, and Chinese Patent Application No. 202010200778.2, filed on Mar. 20, 2020. The entire contents of each of the foregoing applications are incorporated herein by reference.

TECHNICAL FIELD

The present disclosure relates to novel macrocyclic derivatives, a preparation method therefor, a pharmaceutical composition containing the macrocyclic derivative, and use of the macrocyclic derivatives and the pharmaceutical composition as a therapeutic agent, in particular as a factor XIa inhibitor, and use thereof in a medicament for treating and preventing diseases such as thromboembolism.

BACKGROUND

Antithrombotic drugs are mainly classified into antiplatelet drugs (such as clopidogrel, aspirin and ticagrelor), anticoagulant drugs (such as heparin, low-molecular heparin, hirudin and warfarin) and thrombolytic drugs (such as urokinase, streptokinase and plasmin). In clinical application, antiplatelet drugs and anticoagulant drugs are mainly used for preventing arterial and venous thrombus, and thrombolytic drugs are used for dissolving thrombus. As the incidence of cardiovascular and cerebrovascular diseases of China continuously rises in recent years, the sales of antithrombotic drugs witnesses steady annual increase of 15-20%, with the sales in 2016 hitting nearly 20 billion yuan. The incidence of cardiovascular and cerebrovascular diseases is expected to remain high in the future with the aggravation of aging, and the market for antithrombotic drugs will continuously grow.

The anticoagulant drugs can be widely used for treating and preventing various arterial and venous thrombus, such as acute coronary syndrome, cerebral apoplexy, transient cerebral ischemia, deep venous embolism, pulmonary venous embolism and peripheral atherosclerosis occlusion, and they are of great significance in various authoritative guidelines. Particularly, novel oral anticoagulant drugs on the market in recent years are included in authoritative guidelines successively, and they have displaced the traditional anticoagulant drugs such as warfarin and heparin as the first-choice drugs recommended by the guidelines by virtue of better therapeutic effects and safety shown in clinical trials.

Human blood coagulation process comprises two processes: intrinsic and extrinsic pathways and a common pathway. The extrinsic pathway refers to the fact that the tissue factor binds to activated factor VII (FVIIa) to form a complex in the case of injury and various external stimuli and the complex then reactivates factor X (FX) to form activated FX (FXa). FXa then converts prothrombin to thrombin, which catalyzes the formation of fibrin from fibrinogen, thus playing a role in blood coagulation. The intrinsic pathway is an inherent pathway of the body, and all factors involved in blood coagulation come from blood. By cascade reaction, factor XII (FXII) is activated, factor XI (FXI) is then activated by activated FXII (FXIIa), factor IX (FIX) is activated by activated FXI (FXIa), and further FX is activated by activated FIX (FIXa). Thrombin is later produced via a common pathway, which in turn can activate FXI.

The risk of bleeding is a major concern of antithrombotic drugs. Therefore, coagulation factors that are directed against the intrinsic pathway but do not affect the extrinsic and common pathways are ideal targets of antithrombotic drugs. Due to the unique role of FXI/FXIa in the coagulation pathway and process, as well as the important features of FXI gene deficiency being capable of preventing thrombosis without significantly increasing the risk of bleeding, FXI/FXIa has become an important target for the development of novel anticoagulant drugs. The FXI zymogen protein is a 160-kDa disulfide bond-linked dimer having identical subunits, and each subunit comprises 4 "apple domains" and 1 C-terminal catalytic domain. FXI, after being activated, becomes enzymatically active FXIa, and the downstream zymogen protein FIX is cleaved via the catalytic domain and is thus activated.

Antithrombotic drugs targeting FXI/FXIa comprise antisense drugs, monoclonal antibodies and small molecule inhibitors, and there are on-going clinical researches for each type, wherein the research for antisense drugs progresses most rapidly as a key clinical phase II trial has been completed and a positive result obtained, and the effectiveness and safety of the antithrombotic drugs targeting FXI/FXIa are verified in the human body.

At present, several companies have published patents involving using macrocyclic derivatives as FXIa inhibitors, such as patents WO2011100401, WO2011100402, WO2013022814, WO2013022818, WO2014022766, WO2014022767, WO2015116882, WO2015116885, WO2015116886 and WO2016053455 of BMS, patents WO2017074832 and WO2017074833 of Merck, and patent WO2018133793 of Sunshine Lake Pharma Co., Ltd. The macrocyclic compounds disclosed in these patents are generally high in activity, but the in vivo pharmacokinetic results are not ideal due to the large molecular weight.

Content of the Invention

In one aspect, the present disclosure provides a compound of formula (I), an isomer thereof, or a pharmaceutically acceptable salt thereof,

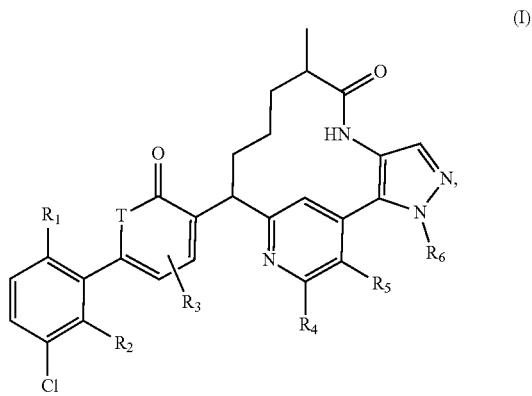

wherein,

T is —O— or —N($R_a$)—;

$R_a$ is H or $C_{1-3}$ alkyl;

$R_1$ is triazolyl or tetrazolyl, wherein the triazolyl and tetrazolyl are optionally substituted with $R_b$;

R₂ is H or F;

R₃ is H, F, Cl, Br, CN, $C_{1-6}$ alkyl, $C_{1-6}$ alkoxy or $C_{1-6}$ alkylamino;

R₄ and R₅ are each independently H, F, Cl, Br, I, $C_{1-3}$ alkyl, $C_{1-3}$ haloalkyl or $C_{1-3}$ alkoxy;

R₆ is $C_{1-3}$ alkyl optionally substituted with 1, 2 or 3 $R_c$;

$R_b$ and $R_c$ are each independently F, Cl, Br, I, $C_{1-3}$ alkyl, $C_{1-3}$ haloalkyl, $C_{1-3}$ alkoxy or $C_{3-4}$ cycloalkyl.

The present disclosure provides a compound of formula (I), an isomer thereof or a pharmaceutically acceptable salt thereof, (I)

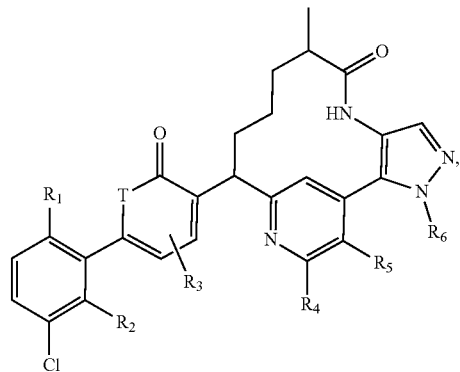

wherein,

T is —O— or —N($R_a$)—;

$R_a$ is H or $C_{1-3}$ alkyl;

R₁ is triazolyl or tetrazolyl, wherein the triazolyl and tetrazolyl are optionally substituted with $R_b$;

R₂ is H or F;

R₃ is H, F, Cl, Br, CN, $C_{1-6}$ alkyl, $C_{1-6}$ alkoxy or $C_{1-6}$ alkylamino;

R₄ and Rs are each independently H, F, Cl, Br, I, $C_{1-3}$ alkyl, $C_{1-3}$ haloalkyl or $C_{1-3}$ alkoxy;

R₆ is $C_{1-3}$ alkyl optionally substituted with 1, 2 or 3 $R_c$;

$R_b$ and $R_c$ are each independently F, Cl, Br, I, $C_{1-3}$ alkyl, $C_{1-3}$ alkoxy or $C_{3-4}$ cycloalkyl.

In some embodiments of the present disclosure, the above compound has a structure shown as formula (I-1) or (I-2):

(I-1)

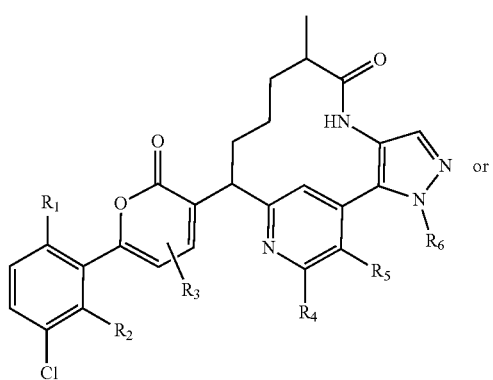

(I-2)

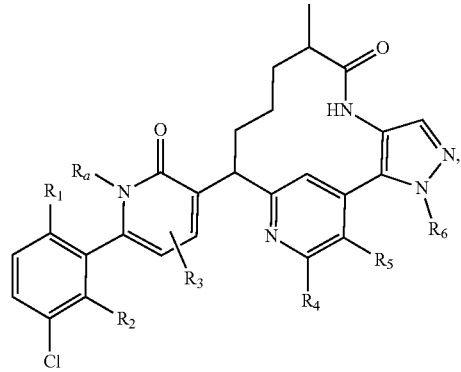

wherein R₁, R₂, R₃, R₄, R₅, R₆ and $R_a$ are as defined in the present disclosure.

In some embodiments of the present disclosure, the above compound has a structure shown as formula (I-1-a) or (I-2-a):

(I-1-a)

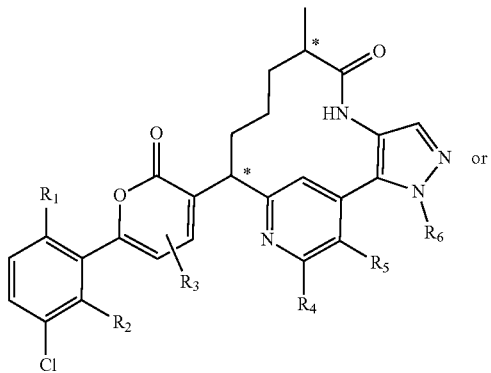

or (I-2-a)

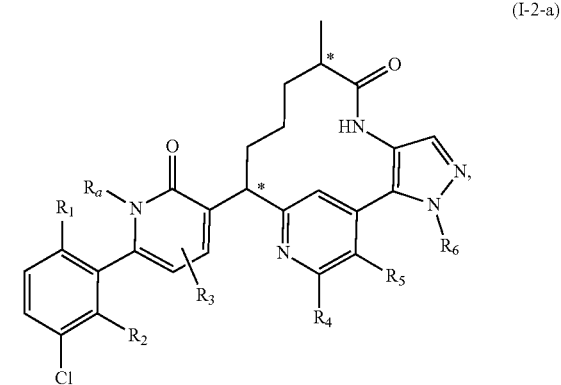

wherein the carbon atom with "*" is a chiral carbon atom present in a form of single (R) or (S) enantiomer or in a form enriched with one enantiomer; R₁, R₂, R₃, R₄, R₅, R₆ and $R_a$ are as defined in the present disclosure.

In some embodiments of the present disclosure, the above compound has a structure shown as formula (I-1-b) or (I-2-b):

(I-1-b)

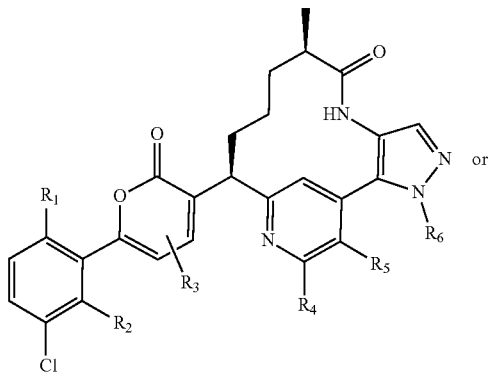

or (I-2-b)

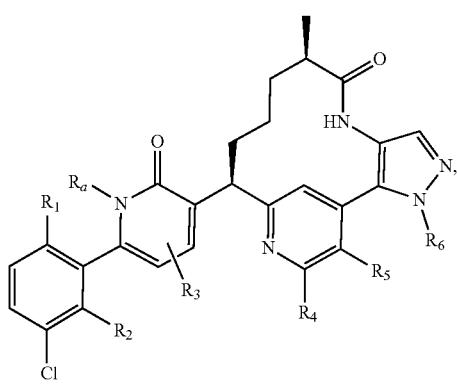

wherein $R_1$, $R_2$, $R_3$, $R_4$, $R_5$, $R_6$ and $R_a$ are as defined in the present disclosure.

In some embodiments of the present disclosure, $R_a$ is H, —$CH_3$ or —$CH_2CH_3$, and the other variables are as defined in the present disclosure.

In some embodiments of the present disclosure, T is —O—, —NH— or —N($CH_3$)—, and the other variables are as defined in the present disclosure. In some embodiments of the present disclosure, T is —O— or —NH—, and the other variables are as defined in the present disclosure.

In some embodiments of the present disclosure, $R_b$ and $R_c$ are each independently F, Cl, methyl, —$CHF_2$, ethoxy or cyclopropyl, and the other variables are as defined in the present disclosure.

In some embodiments of the present disclosure, $R_b$ and $R_c$ are each independently F, Cl, methyl, ethoxy or cyclopropyl, and the other variables are as defined in the present disclosure.

In some embodiments of the present disclosure, $R_b$ is Cl, —$CHF_2$, ethoxy or cyclopropyl, and the other variables are as defined in the present disclosure.

In some embodiments of the present disclosure, $R_c$ is F, and the other variables are as defined in the present disclosure.

In some embodiments of the present disclosure, $R_1$ is

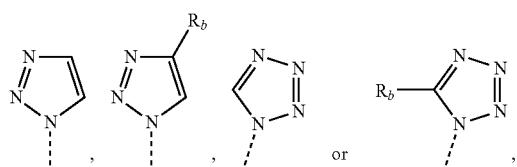

and $R_b$ and the other variables are as defined in the present disclosure.

In some embodiments of the present disclosure, $R_1$ is

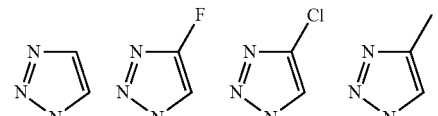

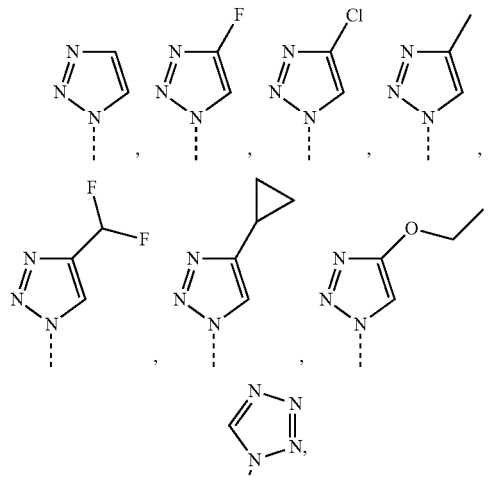

and the other variables are as defined in the present disclosure.

In some embodiments of the present disclosure, $R_1$ is

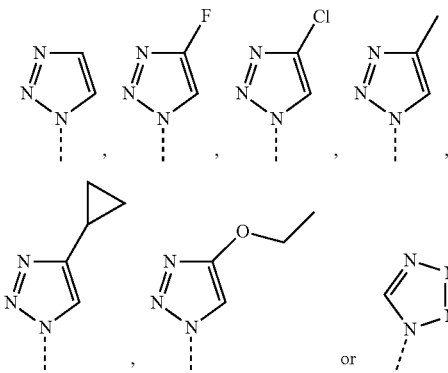

and the other variables are as defined in the present disclosure.

In some embodiments of the present disclosure, $R_3$ is H, F, Cl, Br, CN, $C_{1-3}$ alkyl, $C_{1-3}$ alkoxy or $C_{1-3}$ alkylamino, and the other variables are as defined in the present disclosure.

In some embodiments of the present disclosure, $R_3$ is H, F, Cl, Br, CN, —$CH_3$, —$OCH_3$,

and the other variables are as defined in the present disclosure.

In some embodiments of the present disclosure, $R_4$ and $R_5$ are each independently H, F, Cl, Br, I,

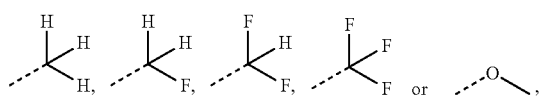

and the other variables are as defined in the present disclosure.

In some embodiments of the present disclosure, R₆ is —CH₃ optionally substituted with 1, 2 or R_c, and R_c and the other variables are as defined in the present disclosure.

In some embodiments of the present disclosure, R₆ is

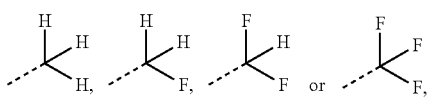

and the other variables are as defined in the present disclosure.

In some embodiments of the present disclosure,

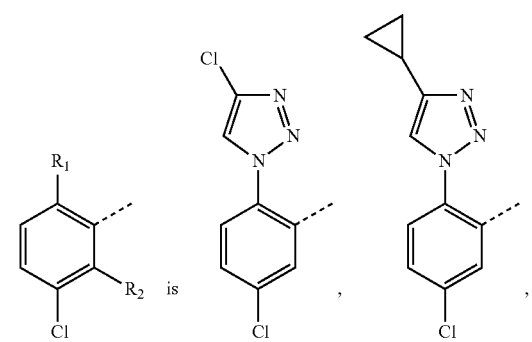

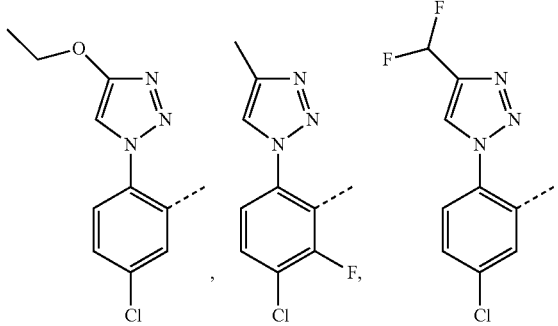

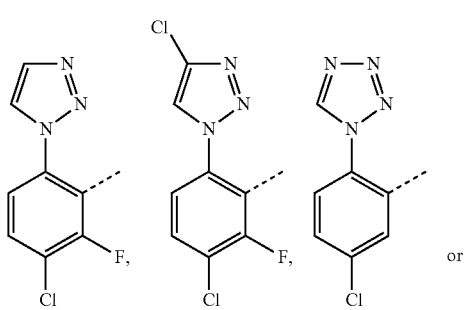

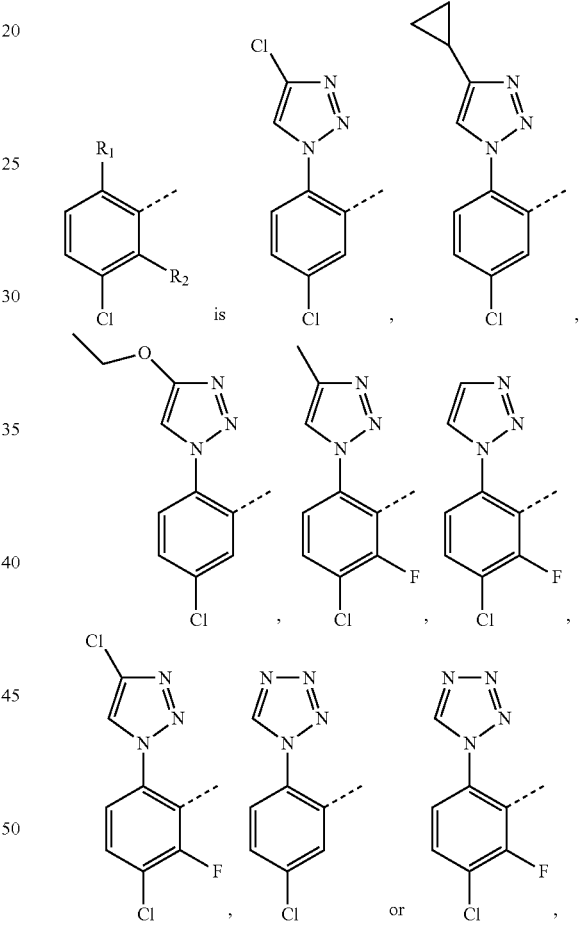

and the other variables are as defined in the present disclosure.

In some embodiments of the present disclosure,

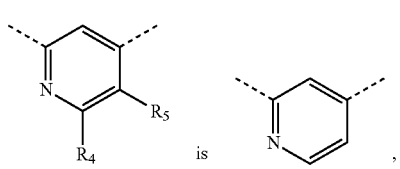

-continued

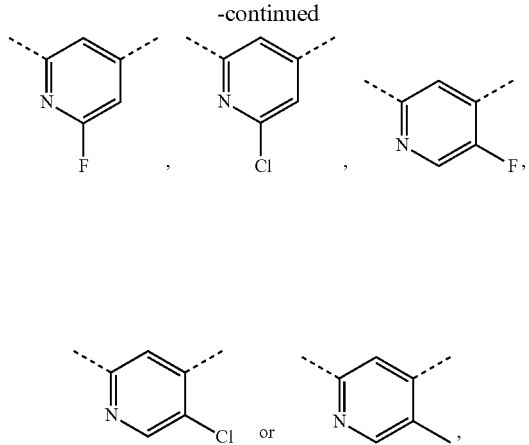

and the other variables are as defined in the present disclosure.

In some embodiments of the present disclosure, the above compound has a structure shown as formula (I-3):

(I-3)

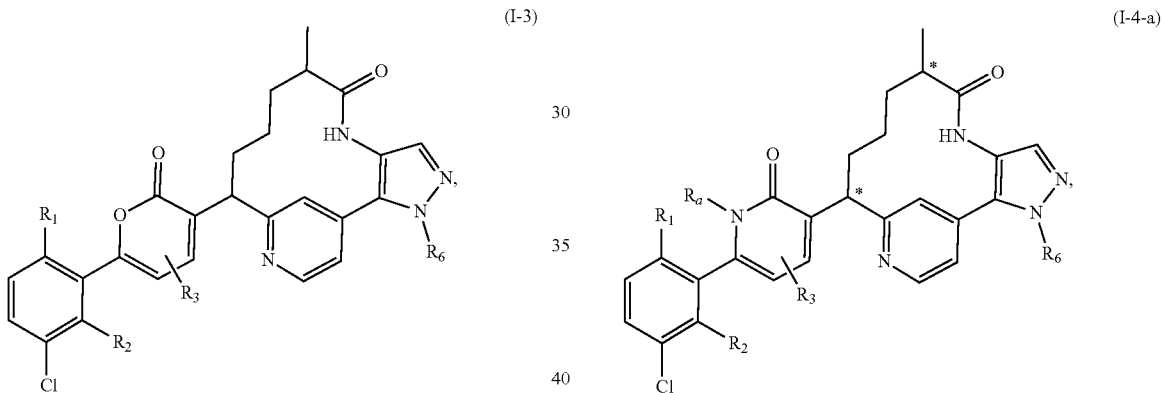

wherein $R_1$, $R_2$, $R_3$ and $R_6$ are as defined in the present disclosure.

In some embodiments of the present disclosure, the above compound has a structure shown as formula (I-4):

(I-4)

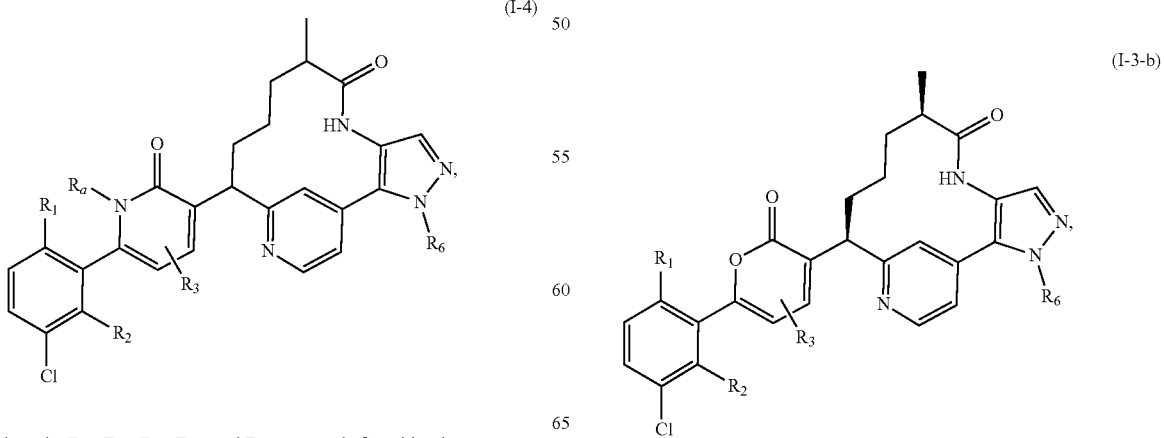

wherein $R_1$, $R_2$, $R_3$, $R_a$ and $R_6$ are as defined in the present disclosure.

In some embodiments of the present disclosure, the above compound has a structure shown as formula (I-3-a):

(I-3-a)

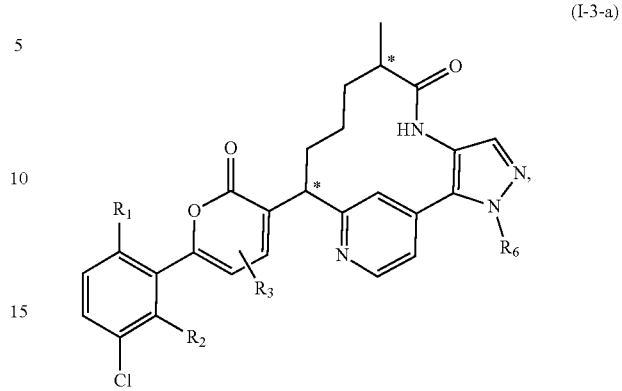

wherein the carbon atom with "*" is a chiral carbon atom present in a form of a single (R) or (S) enantiomer or in a form enriched with one enantiomer;

$R_1$, $R_2$, $R_3$ and $R_6$ are as defined in the present disclosure.

In some embodiments of the present disclosure, the above compound has a structure shown as formula (I-4-a):

(I-4-a)

wherein the carbon atom with "*" is a chiral carbon atom present in a form of a single (R) or (S) enantiomer or in a form enriched with one enantiomer;

$R_1$, $R_2$, $R_3$, $R_a$ and $R_6$ are as defined in the present disclosure.

In some embodiments of the present disclosure, the above compound has a structure shown as formula (I-3-b):

(I-3-b)

wherein $R_1$, $R_2$, $R_3$ and $R_6$ are as defined in the present disclosure.

In some embodiments of the present disclosure, the above compound has a structure shown as formula (I-4-b):

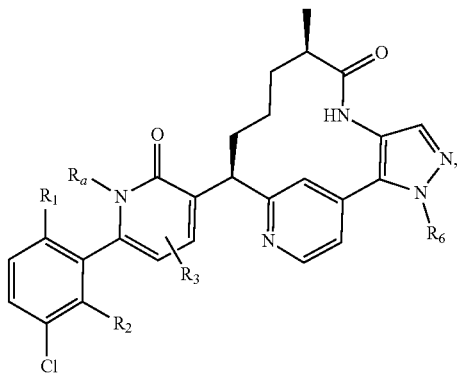

(I-4-b)

wherein $R_1$, $R_2$, $R_3$, $R_a$ and $R_6$ are as defined in the present disclosure.

In some embodiments of the present disclosure, the above compound has a structure shown as (I-5) or (I-6):

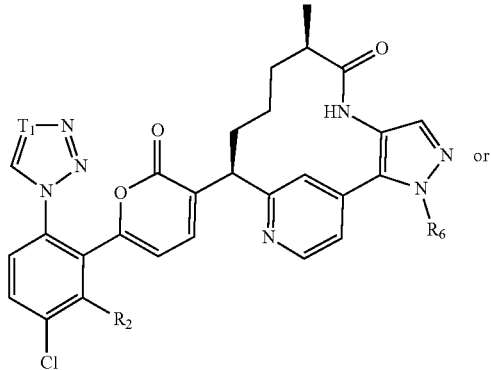

(I-5)

or

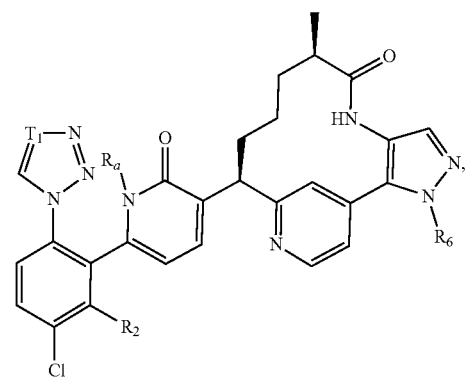

(I-6)

wherein $T_1$ is N or $CR_b$; $R_2$, $R_a$, $R_6$ and $R_b$ are as defined in the present disclosure.

Still some other embodiments of the present disclosure are derived from any combination of the variables described above.

In some embodiments of the present disclosure, the above compound is:

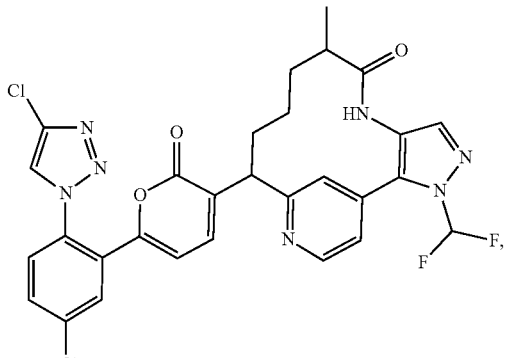

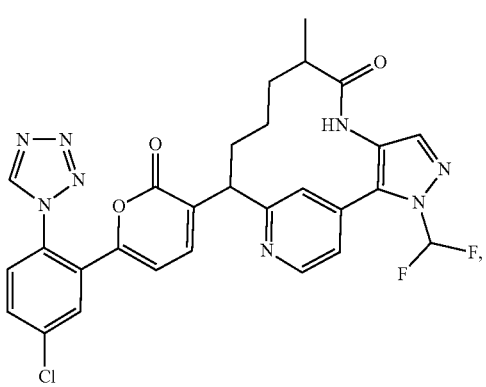

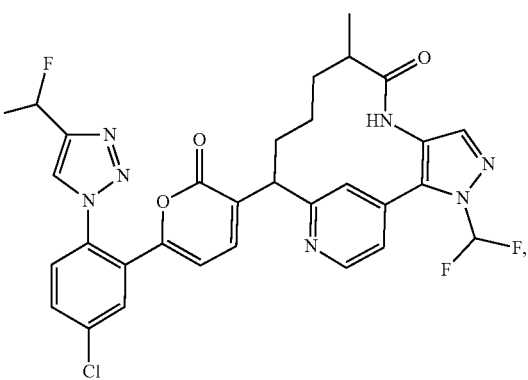

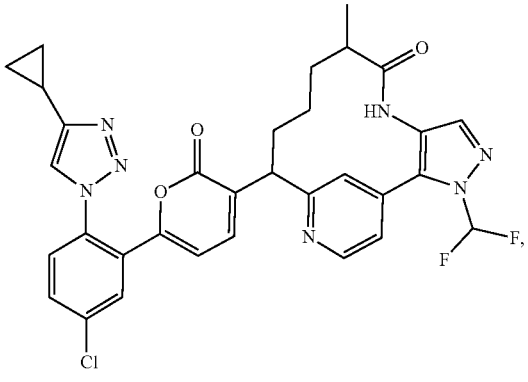

13
-continued
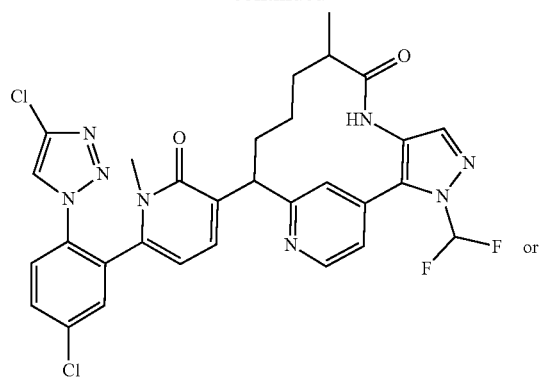
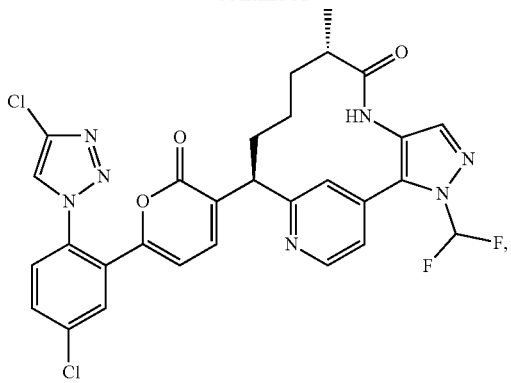
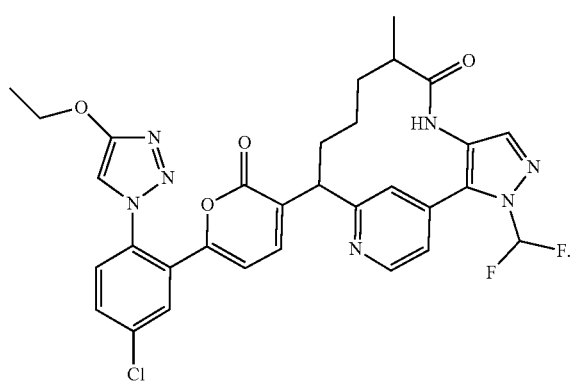
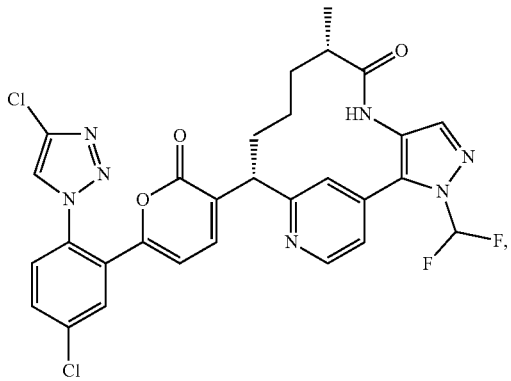
In some embodiments of the present disclosure, the above compound is:
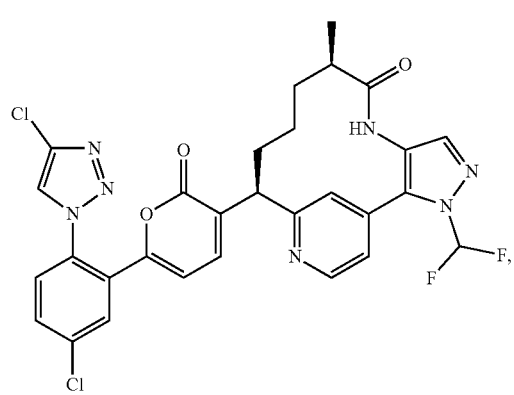
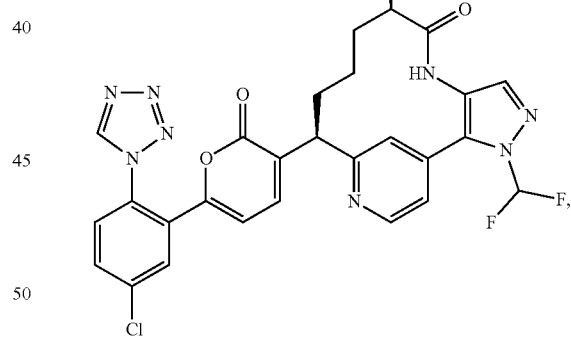
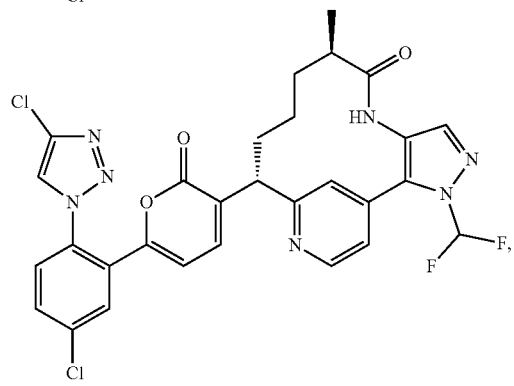
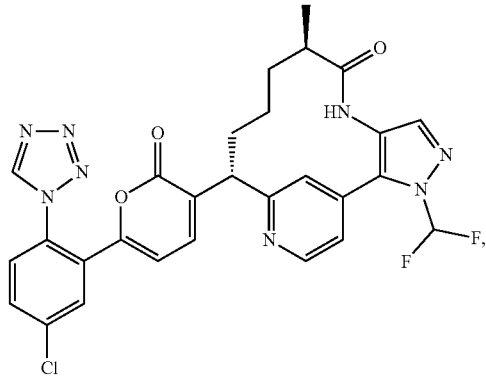

-continued
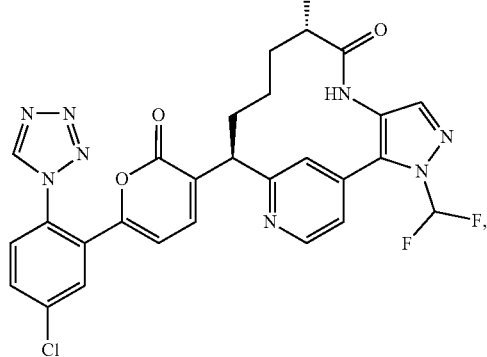
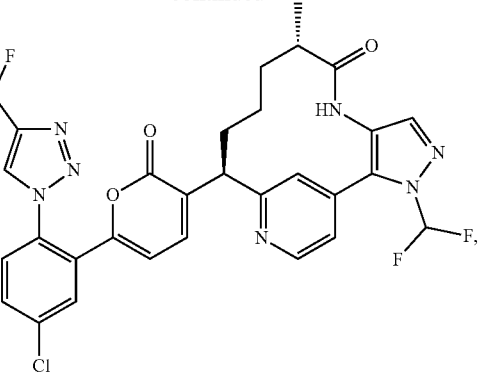
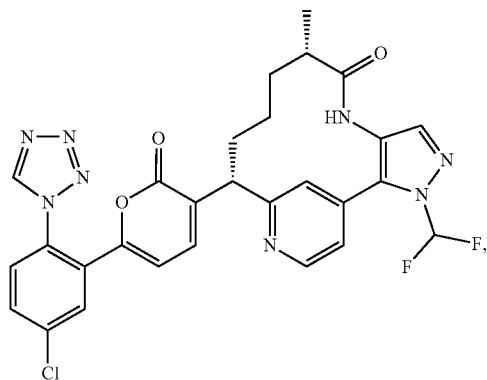
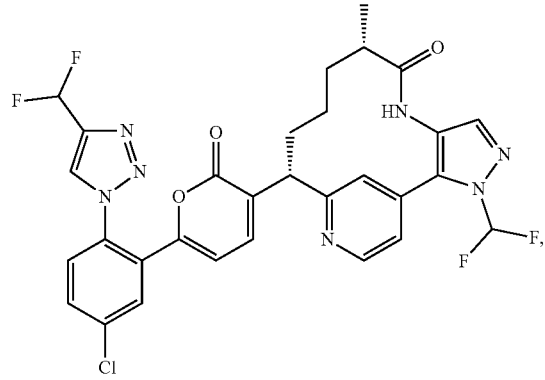
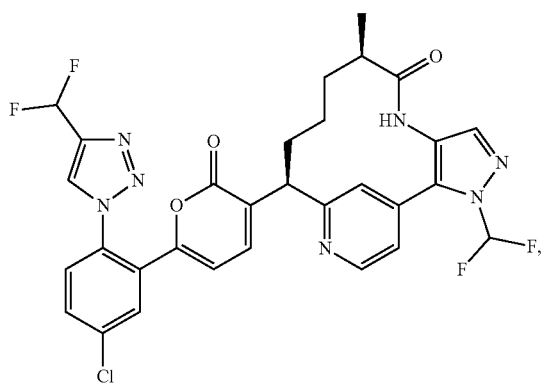
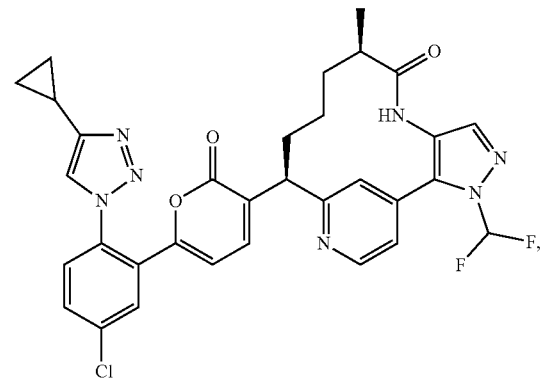
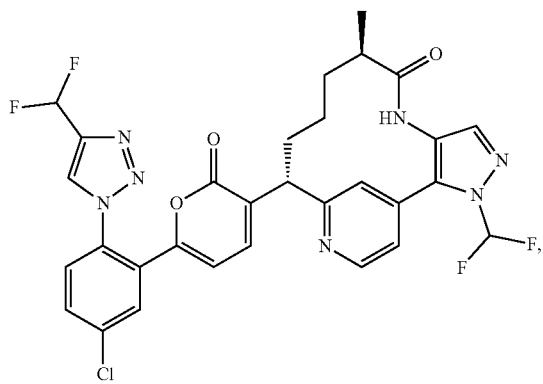
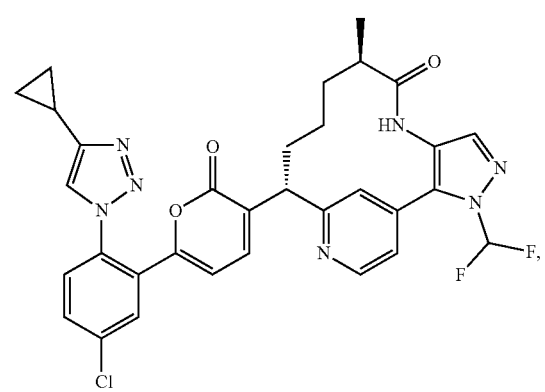

17
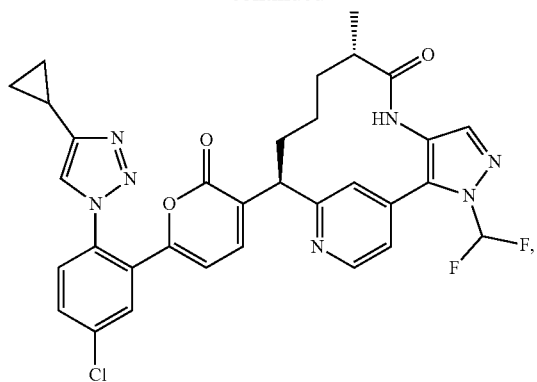
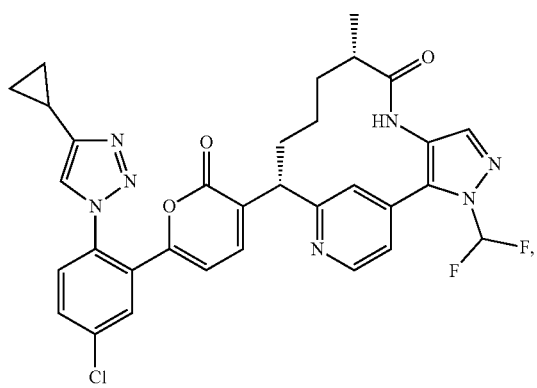
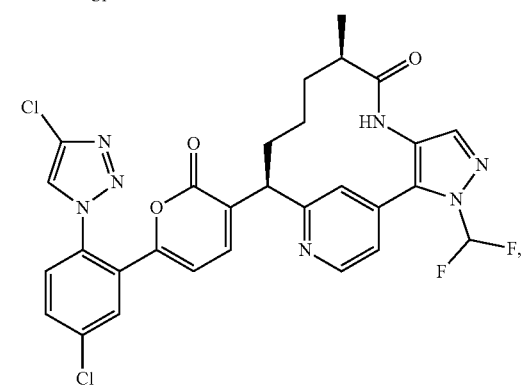
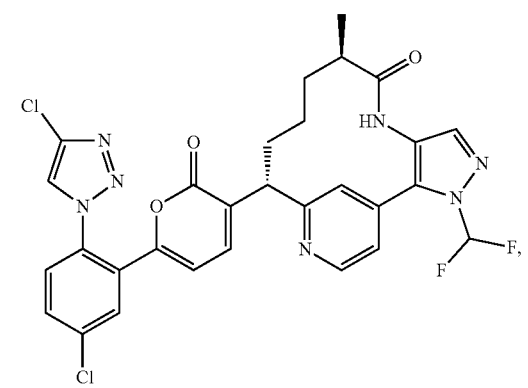
18
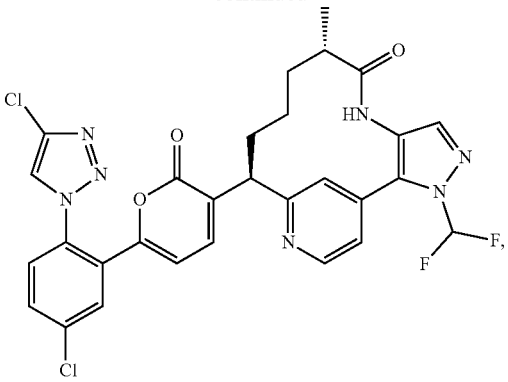
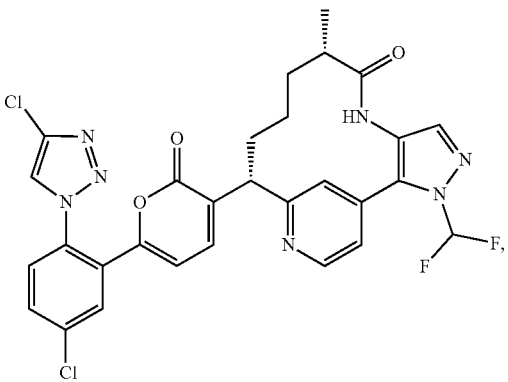
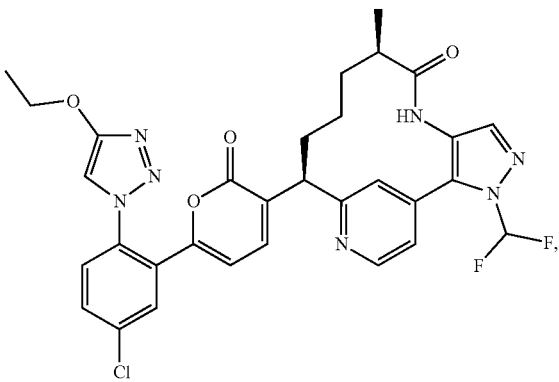
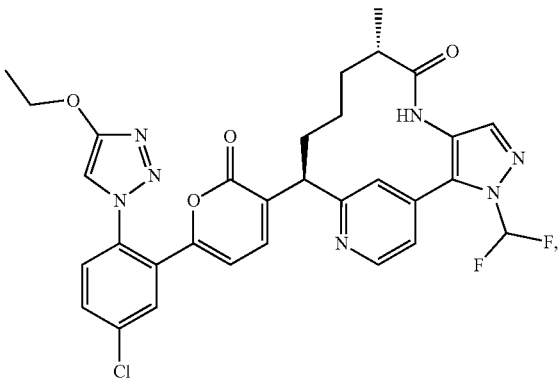

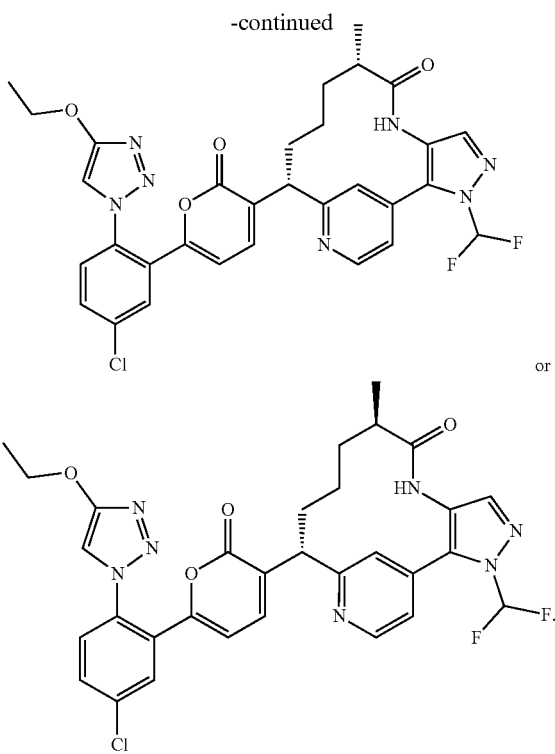

or

In another aspect, the present disclosure provides a pharmaceutical composition comprising a therapeutically effective amount of the compound, the isomer thereof or the pharmaceutically acceptable salt thereof described above and a pharmaceutically acceptable carrier.

The present disclosure further provides use of the compound, the isomer thereof or the pharmaceutically acceptable salt thereof described above or the pharmaceutical composition described above in preparing a medicament as a factor XIa inhibitor.

Technical effects

The object of the present disclosure is to provide a macrocyclic compound suitable for an FXIa enzyme inhibitor, an analog thereof, and a pharmaceutical combination comprising the macrocyclic compound; such a macrocyclic compound or pharmaceutical composition is effective in treating and preventing thromboembolic diseases. Such a compound not only has higher FXIa enzyme activity and human blood in vitro anticoagulation effect, but also has better in vivo pharmacokinetic properties.

Definitions and description

Unless otherwise stated, the following terms and phrases used herein are intended to have the following meanings. A particular term or phrase, unless otherwise specifically defined, should not be considered as uncertain or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents disclosed herein and a relatively nontoxic acid or base. When the compound of the present disclosure contains a relatively acidic functional group, a base addition salt can be obtained by contacting such a compound with a sufficient amount of a base in a pure solution or a suitable inert solvent. Pharmaceutically acceptable base addition salts include sodium, potassium, calcium, ammonium, organic amine, or magnesium salts, or similar salts. When the compound disclosed herein contains a relatively basic functional group, an acid addition salt can be obtained by contacting such a compound with a sufficient amount of an acid in a pure solution or a suitable inert solvent. Examples of pharmaceutically acceptable acid addition salts include salts derived from inorganic acids, such as hydrochloric acid, hydrobromic acid, nitric acid, carbonic acid, bicarbonate radical, phosphoric acid, monohydrogen phosphate, dihydrogen phosphate, sulfuric acid, hydrogen sulfate, hydroiodic acid and phosphorous acid; and salts derived from organic acids, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid. Also included are salts of amino acids (e.g., arginine) and salts of organic acids such as glucuronic acid. Certain specific compounds disclosed herein contain both basic and acidic functional groups that allow the compounds to be converted into either base or acid addition salts.

The pharmaceutically acceptable salts of the present disclosure can be synthesized from a parent compound having an acidic or basic group by conventional chemical methods. In general, such salts are prepared by the following method: performing a reaction of the free acid or base form of the compound and a stoichiometric amount of the appropriate base or acid in water or an organic solvent or a mixture thereof.

The compound of the present disclosure may have a specific geometric or stereoisomeric form. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereomer enriched mixture, all of which are encompassed within the scope of the present disclosure. Substituents such as alkyl may have an additional asymmetric carbon atom. All these isomers and mixtures thereof are encompassed within the scope of the present disclosure.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers in which molecules each have two or more chiral centers and are not mirror images of each other.

Unless otherwise stated, "(+)" stands for dextrorotation, "(−)" stands for levorotation, and "(±)" stands for racemization.

Unless otherwise stated, the absolute configuration of a stereogenic center is represented by a wedged solid bond ( ◢ ) and a wedged dashed bond ( ◌ ) and the relative configuration of a stereogenic center is represented by a straight solid bond ( ◢ ) and a straight dashed bond ( ◌ ). A wavy line ( ∿ ) represents a wedged solid bond ( ◢ ) or a wedged dashed bond ( ) or a wavy line ( ) represents a straight solid bond ( ) and a straight dashed bond ( ).

Unless otherwise stated, the term "enriched with one isomer", "isomer enriched", "enriched with one enantiomer" or "enantiomer enriched" means that the content of one of the isomers or enantiomers is less than 100% and more than or equal to 60%, 70%, 80%, 90%, 95%, 96%, 97%, 98%, 99%, 99.5%, 99.6%, 99.7%, 99.8% or 99.9%.

Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. If one enantiomer of a certain compound disclosed herein is to be obtained, the desired pure enantiomer can be prepared by asymmetric synthesis or derivatization using a chiral auxiliary, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to get the pure enantiomer. Furthermore, the enantiomer and the diastereoisomer are generally isolated through chromatography using a chiral stationary phase, optionally in combination with chemical derivatization (e.g., carbamate generated from amines). The compound of the present disclosure may contain an unnatural proportion of atomic isotope at one or more of the atoms that constitute the compound. For example, the compound may be labeled with a radioisotope, such as tritium ($^3$H), iodine-125 ($^{125}$I), or C-14 ($^{14}$C). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compound of the present disclosure, whether radioactive or not, are encompassed within the scope of the present disclosure. "Optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituents which may include deuterium and hydrogen variants, as long as the valence of the specific atom is normal and the substituted compound is stable. When the substituent is an oxygen (i.e., =O), it means that two hydrogen atoms are substituted. Substitution by oxygen does not occur on aromatic groups. The term "optionally substituted" means that an atom can be substituted by a substituent or not. Unless otherwise specified, the type and number of the substituent may be arbitrary as long as being chemically achievable.

When any variable (e.g., R) occurs more than once in the constitution or structure of a compound, the variable is independently defined in each case. Thus, for example, if a group is substituted by 0-2 R, the group can be optionally substituted by two R at most, and the definition of R in each case is independent. Furthermore, a combination of a substituent and/or a variant thereof is permissible only if the combination can result in a stable compound.

When the number of a linking group is 0, for example, —(CRR)$_0$—, it means that the linking group is a single bond.

When one of variants is selected from single bond, then two groups bonding by this variant are bonded directly. For example, in A-L-Z, when L represents a single bond, it means that the structure is actually A-Z.

When a substituent is absent, it means that the substituent does not exist. For example, when X in A-X is absent, the structure is actually A. When it is not specified by which atom the listed substituent is connected to the group to be substituted, the substituent can be connected via any atom of the group. For example, pyridinyl as a substituent can be connected to the group to be substituted via any carbon atom on the pyridine ring.

When the enumerative linking group does not indicate the direction for linking, the direction for linking is arbitrary. For example, when the linking group L contained in

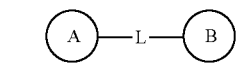

is -M-W-, -M-W-can either link ring A and ring B in a direction same as left-to-right reading order to form

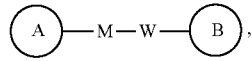, or link ring A and ring B in an opposing direction to form

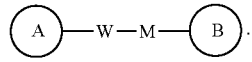.

A combination of the linking group, a substituent and/or a variant thereof is permissible only if the combination can result in a stable compound.

Unless otherwise specified, when a group has one or more connectable sites, any one or more of the sites of the group may be connected to other groups by chemical bonds. The chemical bond that connects the site to another group may be represented by a straight solid bond ( ), a straight dashed line bond ( ), or a wavy line ( ). For example, the straight solid line in —OCH$_3$ indicates that the group is connected to another group through the oxygen atom; in

the straight dashed line indicates that the group is connected to another group through the two ends of the nitrogen atom; in

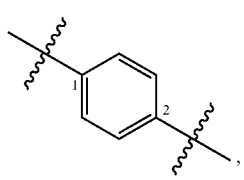 [SMILES: *c1ccc(*)cc1]

the wavy line indicates that the phenyl group is connected to another group through the carbon atoms on positions 1 and 2.

Unless otherwise specified, the number of atoms on a ring is generally defined as the member number of the ring. For example, "5-7 membered ring" refers to a "ring" on which 5 to 7 atoms are arranged in a circle.

Unless otherwise specified, the "5 membered ring" refers to cycloalkyl, heterocycloalkyl, cycloalkenyl, heterocycloalkenyl, cycloalkynyl, heterocycloalkynyl, aryl or heteroaryl consisting of 5 ring atoms. The ring may be monocyclic or bicyclic, wherein the bicyclic ring system includes a spiro ring, a fused ring, a bridged ring, etc. Unless otherwise specified, the ring optionally contains 1, 2, or 3 heteroatoms independently selected from O, S, and N. The term "ring" also includes a ring system containing at least one ring, in which each "ring" independently meets the above definition.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc., and may be monovalent (e.g., methyl), divalent (e.g., methylene), or polyvalent (e.g., methenyl). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like.

Unless otherwise specified, the term "$C_{1-5}$ alkyl" refers to a linear or branched saturated hydrocarbon group consisting of 1 to 5 carbon atoms. The $C_{1-5}$ alkyl includes $C_{1-4}$, $C_{1-3}$, $C_{1-2}$, $C_{2-5}$, $C_{2-4}$ and $C_5$ alkyl, and the like; it may be monovalent (e.g., methyl), divalent (e.g., methylene) or polyvalent (e.g., methenyl). Examples of $C_{1-5}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), and the like.

Unless otherwise specified, the term "$C_{1-4}$ alkyl" refers to a linear or branched saturated hydrocarbon group consisting of 1 to 4 carbon atoms. The $C_{1-4}$ alkyl includes, but is not limited to, $C_{1-2}$, $C_{1-3}$ and $C_{2-3}$ alkyl, and the like, and may be monovalent (e.g., methyl), divalent (e.g., methylene) or polyvalent (e.g., methenyl). Examples of $C_{1-4}$ alkyl include, but are not limited to, methyl (Me), ethyl (Et), propyl (including n-propyl and isopropyl), butyl (including n-butyl, isobutyl, s-butyl and t-butyl), and the like.

Unless otherwise specified, the term "$C_{1-3}$ alkyl" refers to a linear or branched saturated hydrocarbon group consisting of 1 to 3 carbon atoms. The $C_{1-3}$ alkyl includes, but is not limited to, $C_{1-2}$ and $C_{2-3}$ alkyl, etc., and may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), and the like.

Unless otherwise specified, the term "$C_{1-3}$ haloalkyl" refers to monohaloalkyl and polyhaloalkyl containing 1 to 3 carbon atoms. The $C_{1-3}$ haloalkyl includes $C_{1-2}$, $C_{2-3}$, $C_3$, $C_2$ and $C_1$ haloalkyl, and the like. Examples of $C_{1-3}$ haloalkyl include, but are not limited to, trifluoromethyl, trichloromethyl, 2,2,2-trifluoroethyl, pentafluoroethyl, pentachloroethyl, 3-bromopropyl, and the like.

Unless otherwise specified, the term "$C_{1-6}$ alkoxy" refers to those alkyl groups that each contains 1 to 6 carbon atoms and is connected to the rest part of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy and the like. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, and the like.

Unless otherwise specified, the term "$C_{1-4}$ alkoxy" refers to those alkyl groups that each contains 1 to 4 carbon atoms and is connected to the rest part of the molecule through an oxygen atom. The $C_{1-4}$ alkoxy includes $C_1$-3, $C_{1-2}$, $C_{2-4}$, $C_4$ and $C_3$ alkoxy, and the like. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, and the like.

Unless otherwise specified, the term "$C_{1-3}$ alkoxy" refers to those alkyl groups that each contains 1 to 3 carbon atoms and is connected to the rest part of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

Unless otherwise specified, the term "$C_{1-6}$ alkylamino" refers to those alkyl groups that each contains 1 to 6 carbon atoms and is connected to the rest part of the molecule through an amino group. The $C_{1-6}$ alkylamino includes $C_{1-4}$, $C_1$-3, $C_{1-2}$, $C_{2-6}$, $C_{2-4}$, $C_6$, $C_5$, $C_4$, $C_3$ and $C_2$ alkylamino and the like. Examples of $C_{1-6}$ alkylamino include, but are not limited to, —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, and the like.

Unless otherwise specified, the term "$C_{1-4}$ alkylamino" refers to those alkyl groups that each contains 1 to 4 carbon atoms and is connected to the rest part of the molecule through an amino group. The $C_{1-4}$ alkylamino includes $C_1$-3, $C_{1-2}$, $C_{2-4}$, $C_4$, $C_3$ and $C_2$ alkylamino and the like. Examples of $C_{1-4}$ alkylamino include, but are not limited to, —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, and the like.

Unless otherwise specified, the term "$C_{1-3}$ alkylamino" refers to those alkyl groups that each contains 1 to 3 carbon atoms and is connected to the rest part of the molecule through an amino group. The $C_1$-3 alkylamino includes $C_{1-2}$, $C_3$ and $C_2$ alkylamino and the like. Examples of $C_{1-3}$ alkylamino include, but are not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, and the like.

Unless otherwise specified, "$C_{3-4}$ cycloalkyl" refers to a saturated cyclic hydrocarbon group consisting of 3 to 4 carbon atoms, and it is a monocyclic ring system and can be monovalent, divalent or polyvalent. Examples of $C_{3-4}$ cycloalkyl include, but are not limited to, cyclopropyl, cyclobutyl, and the like.

Unless otherwise specified, the terms "$C_{6-10}$ romatic ring" and "$C_{6-10}$ aryl" are used interchangeably. The term "$C_{6-10}$ aromatic ring" or "$C_{6-10}$ aryl" refers to a cyclic hydrocarbon group consisting of 6 to 10 carbon atoms and having a conjugated π-electron system. The group may be a monocyclic, fused bicyclic or fused tricyclic system, where the rings are aromatic. It may be monovalent, divalent or polyvalent, and the $C_{6-10}$ aryl includes $C_6$-9, $C_9$, Cio and $C_6$ aryl groups, etc. Examples of $C_{6-10}$ aryl include, but are not limited to, phenyl, naphthyl (including 1-naphthyl, 2-naphthyl, etc.).

Unless otherwise specified, $C_{n-n+m}$ or $C_n-C_{n+m}$ includes any one of the specific cases of n to n+m carbon atoms. For example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$. Also, any range within n to n+m may be included. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc. Similarly, n–n+m membered represents that the number of atoms on the ring is n to n+m. For example, 3-12 membered ring includes 3 membered ring, 4 membered ring, 5 membered ring, 6 membered ring, 7 membered ring, 8 membered ring, 9 membered ring, 10 membered ring, 11 membered ring and 12 membered ring. n–n+m membered also represents any range within n to n+m. For example, 3-12 membered ring includes 3-6 membered ring, 3-9 membered ring, 5-6 membered ring, 5-7 membered ring, 6-7 membered ring, 6-8 membered ring, 6-10 membered ring, etc.

The term "leaving group" refers to a functional group or atom that can be replaced by another functional group or atom through a substitution reaction (e.g., nucleophilic substitution). For example, representative leaving groups include triflate; chlorine, bromine and iodine; sulfonate groups, such as mesylate, tosylate, p-bromobenzenesulfonate and p-toluenesulfonate; acyloxy groups, such as acetoxy, and trifluoroacetoxy.

The term "protecting group" includes, but is not limited to, "amino protecting group", "hydroxy protecting group" or "sulfydryl protecting group". The term "amino protecting group" refers to a protecting group suitable for preventing side reactions at the nitrogen atom of the amino. Representative amino protecting groups include, but are not limited to: formyl; acyl, such as alkanoyl (such as acetyl, trichloroacetyl or trifluoroacetyl); alkoxycarbonyl, such as tert-butoxycarbonyl (Boc); arylmethyloxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl)methyl; and silyl, such as trimethylsilyl (TMS) and tert-butyldimethylsilyl (TBS). The term "hydroxy protecting group" refers to a protecting group suitable for preventing side reactions of the hydroxyl group. Representative hydroxy protecting groups include, but are not limited to: alkyl, such as methyl, ethyl, and tent-butyl; acyl, such as alkanoyl (such as acetyl); arylmethyl, such as benzyl (Bn), p-methoxybenzyl (PMB), 9-fluorenylmethyl (Fm) and diphenylmethyl (DPM); and silyl, such as trimethylsilyl (TMS) and tert-butyldimethylsilyl (TBS).

The compounds of the present disclosure can be prepared by a variety of synthetic methods well known to those skilled in the art, including the specific embodiments listed below, embodiments formed by combinations thereof with other chemical synthetic methods, and equivalents thereof known to those skilled in the art. Preferred embodiments include, but are not limited to, the examples disclosed herein.

The solvent used in the present disclosure can be commercially available. The following abbreviations are used in the present disclosure: EtOH represents ethanol; PE represents petroleum ether; EA represents ethyl acetate; MeOH represents methanol; DCM represents dichloromethane; $CHCl_3$ represents trichloromethane; THF represents tetrahydrofuran; $PPh_3$ represents triphenylphosphine; n-BuLi represents n-butyl lithium; DMSO represents dimethyl sulfoxide; LiCl represents lithium chloride; TBSCl represents tert-butyldimethylsilyl chloride; DMAP represents 4-dimethylaminopyridine; $Pd(OAc)_2$ represents palladium acetate; $NH_4Cl$ represents ammonium chloride; KOH represents potassium hydroxide; DMA represents N,N-dimethylacetamide; HATU represents O-(7-azabenzotriazol-1-yl)-N,N,N',N' tetramethyluronium hexafluorophosphate; DIEA represents diisopropylethylamine; HCl represents hydrochloric acid; T3P represents propylphosphonic anhydride; NCS represents 1-chloropyrrolidine-2,5-dione; AcOH represents acetic acid; TLC represents thin layer chromatography; SFC represents supercritical fluid chromatography.

DETAILED DESCRIPTION OF THE EMBODIMENT

The present disclosure is described in detail below by way of examples. However, this is by no means disadvantageously limiting the scope of the present disclosure. Although the present disclosure has been described in detail herein and specific examples have also been disclosed, it will be apparent to those skilled in the art that various changes and modifications can be made to the specific examples without departing from the spirit and scope of the present disclosure.

Synthesis of Intermediate A1

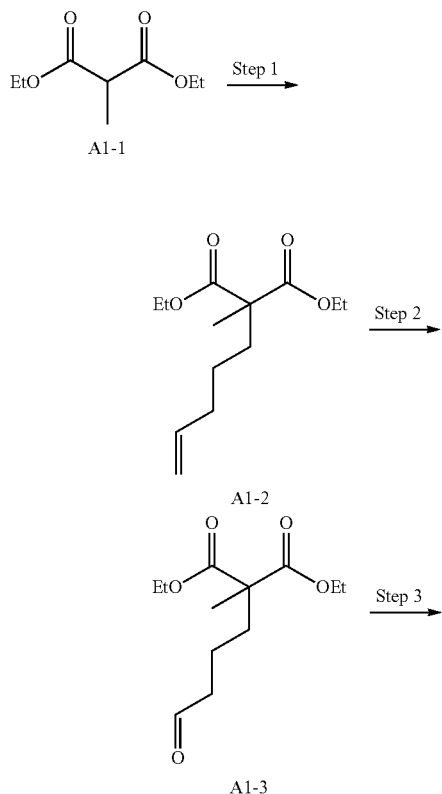

-continued

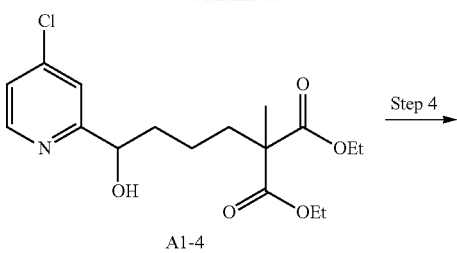
A1-4

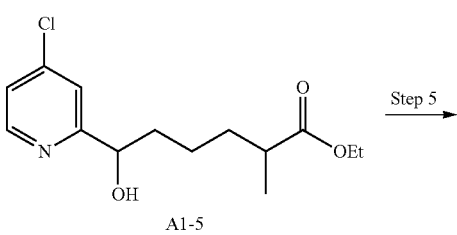
A1-5

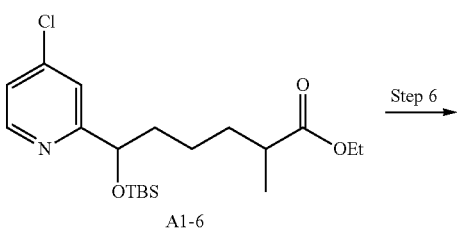
A1-6

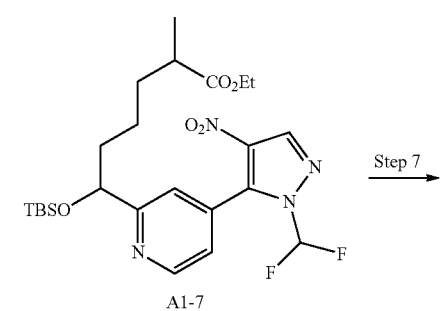
A1-7

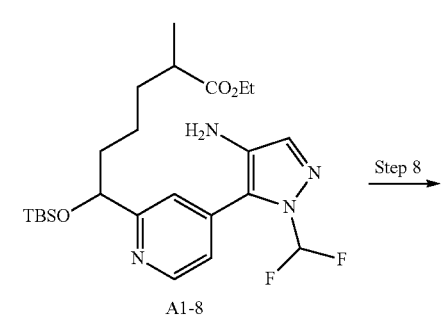
A1-8

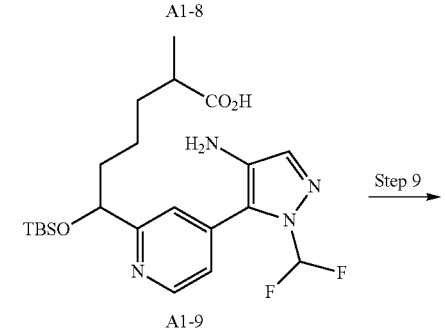
A1-9

-continued

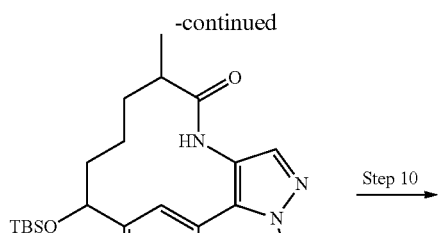
A1-10

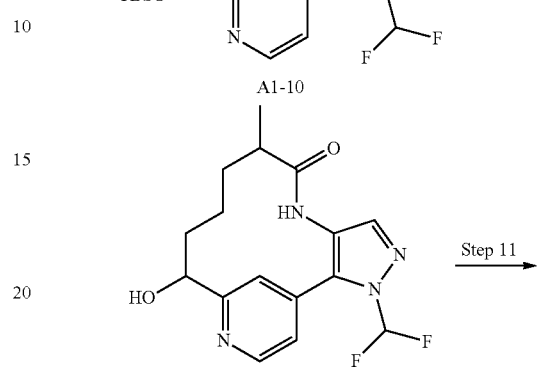
A1-11

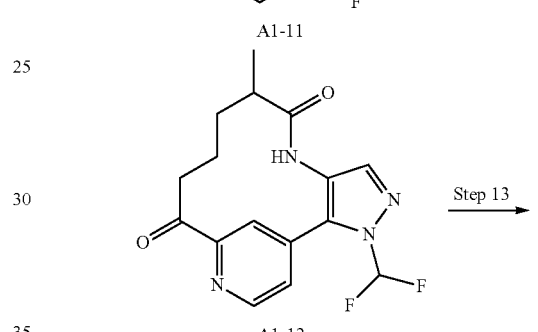
A1-12

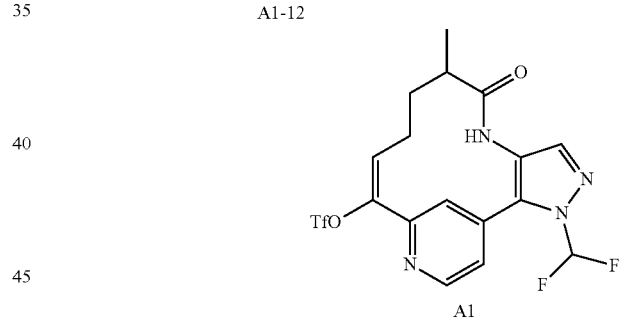
A1

Step 1

EtOH (120 mL) and sodium metal (3.96 g, 172.22 mmol) were added into a pre-dried flask and stirred at 25° C. for 0.5 h, and then starting material A1-1 (30 g, 172.22 mmol) and 5-bromo-1-pentene (25.67 g, 172.22 mmol) were added to the mixture. After three vacuum/nitrogen purge cycles, the reaction mixture was stirred at 95° C. for 5 h and then cooled to room temperature. Saturated aqueous citric acid solution (200 mL) was poured into the reaction mixture, and then ethyl acetate (100 mL) was added. The organic phase was separated out, and the aqueous phase was extracted with ethyl acetate (100 mL×3). The organic phases were combined and washed with water (100 mL×2). After combining the organic phases, concentration under reduced pressure was performed, and the crude product was purified by an automated chromatographic system COMBI-FLASH (gradient elution: PE:EA=300:1 to 100:1) to obtain compound A1-2. $^1$H NMR (400 MHz, CDCl$_3$): δ 5.79 (tdd, J=6.6, 10.2, 17.0 Hz, 1H), 5.06-4.93 (m, 2H), 4.18 (q, J=7.0 Hz, 4H), 2.11-2.03 (m, 2H), 1.91-1.83 (m, 2H), 1.40 (s, 3H), 1.39-1.30 (m, 2H), 1.25 (t, J=7.0 Hz, 6H).

Step 2

A1-2 (43 g, 177.46 mmol) was added to a 500 mL three-necked flask, and then MeOH (120 mL) and DCM (240 mL) were added. Ozone (8.52 g, 177.46 mmol) was introduced into the reaction mixture at −70° C. until the solution turned blue. After the reaction mixture was stirred at −70° C. for 0.5 h, nitrogen was introduced into the solution for 10 min and PPh$_3$ (51.20 g, 195.20 mmol) was added. The resulting reaction mixture was warmed to 25° C. and stirred for 2 h. The reaction mixture was concentrated under reduced pressure, and the crude product was purified by an automated chromatographic system COMBI-FLASH (gradient elution: PE:EA=100:1 to 20:1) to obtain compound A1-3.

Step 3

2-bromo-4-chloropyridine (28.60 g, 148.60 mmol) and toluene (500 mL) were added into a pre-dried flask, and then the reaction mixture was cooled to −78° C. n-BuLi (59.44 mL, 2.5 M) was added. A1-3 (33 g, 135.09 mmol) and toluene (500 mL) were added into another flask, the lithium reagent solution described above was added dropwise slowly to this solution at −78° C., and the resulting reaction mixture was stirred at this temperature for 0.5 h. The reaction mixture was poured into a saturated ammonium chloride solution (200 mL), and ethyl acetate (200 mL) was added thereto. The resulting mixture was left standing for separation.

The organic phase was separated out, and the aqueous phase was extracted with ethyl acetate (100 mL×3). The organic phases were combined and concentrated under reduced pressure. The crude product was purified by an automated chromatographic system COMBI-FLASH (gradient elution: PE:EA=100:1 to 3:1) to obtain compound A1-4. LCMS m/z (ESI): 358.1 (M+1).

$^1$H NMR (400 MHz, CDCl$_3$): δ 8.44 (d, J=5.6 Hz, 1H), 7.32 (d, J=1.6 Hz, 1H), 7.22 (dd, J=2.0, 5.5 Hz, 1H), 4.73 (td, J=4.6, 8.8 Hz, 1H), 4.23-4.11 (m, 4H), 3.78 (d, J=5.6 Hz, 1H), 2.07-1.80 (m, 3H), 1.68 (dt, J=8.0, 14.3 Hz, 1H), 1.46-1.36 (m, 4H), 1.28-1.19 (m, 6H).

Step 4

DMSO (120 mL), A1-4 (38 g, 106.20 mmol), LiCl (9.00 g, 212.39 mmol) and water (1.91 g, 106.20 mmol) were added into a pre-dried flask. After three vacuum/nitrogen purge cycles, the reaction mixture was heated to 180° C. and stirred for 24 h. The reaction mixture was poured into water (200 mL), and ethyl acetate (200 mL) was added. The organic phase was separated off, washed with saturated brine (200 mL×3), and concentrated under reduced pressure to obtain compound A1-5. LCMS m/z (ESI): 286.1 (M+1).

Step 5

A1-5 (27 g, 94.48 mmol) and DCM (200 mL) were added into a pre-dried flask, and then TBSCl (28.48 g, 188.97 mmol), DMAP (8.66 g, 70.86 mmol) and imidazole (16.08 g, 236.21 mmol) were added. The reaction mixture was stirred at 20° C. for 2 h. The reaction mixture was filtered to remove a white solid formed in the reaction system, and the filtrate was concentrated under reduced pressure. The residue was purified by an automated chromatographic system COMBI-FLASH (gradient elution: PE:EA=300:1 to 10:1) to obtain compound A1-6. LCMS m/z (ESI): 400.2 (M+1).

$^1$H NMR (400 MHz, CDCl$_3$): δ 8.38 (d, J=5.4 Hz, 1H), 7.51-7.47 (m, 1H), 7.16 (dd, J=2.0, 5.4 Hz, 1H), 4.78 (t, J=6.0 Hz, 1H), 4.18-4.05 (m, 2H), 2.39 (qd, J=6.8, 13.7 Hz, 1H), 1.78-1.58 (m, 2H), 1.49-1.30 (m, 2H), 1.26-1.20 (m, 5H), 1.11 (d, J=7.6 Hz, 3H), 0.99-0.90 (m, 9H), 0.07 (s, 3H), −0.07 (s, 3H).

Step 6

A1-6 (11 g, 27.50 mmol), 1-difluoromethyl-4-nitropyrazole (4.48 g, 27.50 mmol), n-butylbis(1-adamantyl)phosphine (2.96 g, 8.25 mmol), K$_2$CO$_3$ (9.50 g, 68.75 mmol), 2,2-dimethylpropionic acid (842.53 mg, 8.25 mmol) and 1,4-dioxane (220 mL) were added into a pre-dried flask. After three vacuum/nitrogen purge cycles, Pd(OAc)$_2$ (1.23 g, 5.50 mmol) was added. The reaction mixture was heated to 100° C. and stirred for 13 h. The reaction mixture was filtered, and ethyl acetate (50 mL) and water (50 mL) were added directly to the filtrate. The organic phase was separated out, and the aqueous phase was extracted with ethyl acetate (50 mL×3). The organic phases were combined and concentrated under reduced pressure. The crude product was purified by an automated chromatographic system COMBI-FLASH (gradient elution: PE:EA=300:1 to 10:1) to obtain compound A1-7.

$^1$H NMR (400 MHz, CDCl$_3$): δ 8.71 (d, J=5.0 Hz, 1H), 8.34 (s, 1H), 7.57 (s, 1H), 7.25 (s, 1H), 7.10 (t, J=57.2Hz, 1H), 4.98-4.86 (m, 1H), 4.21-4.03 (m, 2H), 2.45-2.33 (m, 1H), 1.87-1.74 (m, 2H), 1.47-1.31 (m, 2H), 1.29-1.20 (m, 5H), 1.10 (d, J=7.0 Hz, 3H), 0.88 (s, 9H), 0.08 (s, 3H), −0.07 (s, 3H).

Step 7

A1-7 (11 g, 20.89 mmol), EtOH (110 mL) and water (30 mL) were added into a pre-dried flask. After three vacuum/nitrogen purge cycles, NH$_4$Cl (5.59 g, 104.43 mmol) and iron powder (5.83 g, 104.43 mmol) were added, and the reaction was performed at 80° C. for 1 h. The reaction mixture was filtered, and the filter cake was washed with ethyl acetate (30 mL×3). The filtrates were combined and concentrated under reduced pressure to obtain compound A1-8.

$^1$H NMR (400 MHz, CDCl$_3$): δ 8.62 (d, J=5.4 Hz, 1H), 7.60 (s, 1H), 7.43 (s, 1H), 7.26-6.95 (m, 2H), 4.94-4.83 (m, 1H), 4.18-4.03 (m, 2H), 3.18 (br s, 2H), 2.45-2.32 (m, 1H), 1.87-1.73 (m, 2H), 1.71-1.54 (m, 1H), 1.47-1.32 (m, 3H), 1.24-1.17 (m, 3H), 1.10 (dd, J=1.0, 6.8 Hz, 3H), 0.91 (s, 9H), 0.09 (s, 3H), −0.07 (s, 3H).

Step 8

A1-8 (8 g, 16.11 mmol), THF (100 mL) and water (50 mL) were added into a pre-dried flask, and then KOH (1.81 g, 32.21 mmol) was added to the mixture. The resulting reaction mixture was stirred at 30° C. for 12 h. Most of the organic solvent was removed from the reaction mixture under reduced pressure. Saturated sodium hydroxide solution was added to the remaining aqueous phase until pH=13, and then the mixture was extracted with ethyl acetate (50 mL×3). The organic phases were combined and concentrated under reduced pressure to obtain compound A1-9. LCMS m/z (ESI): 469.3 (M+1).

$^1$H NMR (400 MHz, CDCl$_3$): δ 8.52-8.45 (m, 1H), 7.57 (br d, J=2.4 Hz, 1H), 7.37-7.31 (m, 1H), 7.26-6.89 (m, 2H), 4.79 (br d, J=2.9 Hz, 1H), 2.14-2.05 (m, 1H), 1.76-1.61 (m, 2H), 1.56-1.41 (m, 1H), 1.32-1.12 (m, 3H), 0.95-0.80 (m, 12H), 0.06-0.02 (m, 3H), -0.10-0.18 (m, 3H).

Step 9

A1-9 (2.5 g, 5.33 mmol) and DMA (2.5 L) were added into a pre-dried flask, and then HATU (4.06 g, 10.67 mmol) and DIEA (1.38 g, 10.67 mmol) were added at 20° C. The reaction mixture was stirred at 100° C. for 24 h and then directly concentrated under reduced pressure. The crude product was purified by an automated chromatographic system COMBI-FLASH (gradient elution: PE:EA=100:1 to 1:1) to obtain compound A1-10. $^1$H NMR (400 MHz, CD$_3$OD): δ 9.22 (s, 1H), 8.66-8.60 (m, 1H), 7.82-7.61 (m, 2H), 7.54-7.42 (m, 1H), 5.13 (td, J=4.6, 11.4 Hz, 1H), 2.59-2.47 (m, 0.5H), 2.36-2.23 (m, 0.5H), 2.14-1.66 (m, 4H), 1.43-1.14 (m, 2H), 1.13-0.95 (m, 3H), 0.92 (d, J=2.4 Hz, 9H), 0.12 (d, J=6.0 Hz, 3H), 0.01 (d, J=13.6 Hz, 3H).

Step 10

MeOH (35 mL), A1-10 (3.8 g, 8.43 mmol) and HCl/MeOH (6.32 mL, 4 M) were added into a pre-dried flask, and the reaction mixture was stirred at 30° C. for 10 h and then concentrated under reduced pressure. The resulting crude product was dissolved in water (20 mL), and ethyl acetate (20 mL) was added. The reaction mixture was stirred for 5 min, and the organic phase was separated out to remove impurities. Saturated sodium carbonate solution was added to the aqueous phase until pH=8, and then ethyl acetate (20 mL) was added. The organic phase was separated out. The aqueous phase was extracted with ethyl acetate (20 mL×5), and the organic phases were combined and concentrated under reduced pressure to obtain compound A1-11. LCMS m/z (ESI): 337.2 (M+1).

$^1$H NMR (400 MHz, CD$_3$OD): δ 8.66 (t, J=5.4 Hz, 1H), 7.81-7.48 (m, 3H), 7.46 (d, J=4.8 Hz, 1H), 5.04-4.93 (m, 1H), 2.53-2.36 (m, 1H), 1.98-1.71 (m, 3H), 1.61-1.45 (m, 1H), 1.34-1.21 (m, 1H), 1.10-1.01 (m, 3H), 0.94-0.72 (m, 1H).

Step 11

A1-11 (1.9 g, 5.65 mmol), DCM (20 mL) and Dess-Martin reagent (2.88 g, 6.78 mmol) were added into a pre-dried flask, and the reaction mixture was heated to 40° C. and stirred for 12 h. To the reaction mixture was added saturated sodium thiosulfate solution (50 mL) and the resulting mixture was stirred for 10 min. The organic phase was separated out and the aqueous phase was extracted with DCM (20 mL×3). The organic phases were combined and then concentrated under reduced pressure. The crude product was purified by an automated chromatographic system COMBI-FLASH (gradient elution: DCM:MeOH=100:1 to 0:1) to obtain compound A1-12. LCMS m/z (ESI): 335.1 (M+1).

Step 12

THF (450 mL) and A1-12 (1.6 g, 4.79 mmol) were added into a pre-dried flask, and then the reaction mixture was cooled to -70° C. LiHMDS (11.98 mL, 1 M) was added, and the resulting mixture was stirred for 0.5 h. N-phenylbis(trifluoromethanesulfonyl)imide (2.05 g, 5.75 mmol) was added, and the resulting reaction mixture was warmed to 25° C. and stirred for 12 h. To the reaction mixture was added water (20 mL) to quench the reaction, and the resulting mixture was then concentrated under reduced pressure to remove most of the THF. Ethyl acetate (30 mL) was added and the reaction mixture was separated to obtain an organic phase. The aqueous phase was extracted with ethyl acetate (30 mL×3). The organic phases were combined and concentrated under reduced pressure. The crude product was purified by an automated chromatographic system COMBI-FLASH (gradient elution: PE:EA=20:1 to 1:1) to obtain compound A1. LCMS m/z (ESI): 467.1 (M+1).

$^1$H NMR (400 MHz, CD$_3$OD): δ 8.84 (d, J=5.0 Hz, 1H), 7.91-7.66 (m, 1H), 7.57 (s, 1H), 7.42-7.33 (m, 1H), 7.31-7.22 (m, 1H), 6.39-6.28 (m, 1H), 2.59 (br s, 1H), 2.24 (br s, 1H), 2.00-1.77 (m, 1H), 1.38-1.27 (m, 1H), 1.20-1.08 (m, 3H), 0.99-0.76 (m, 1H).

Synthesis of Intermediate A2

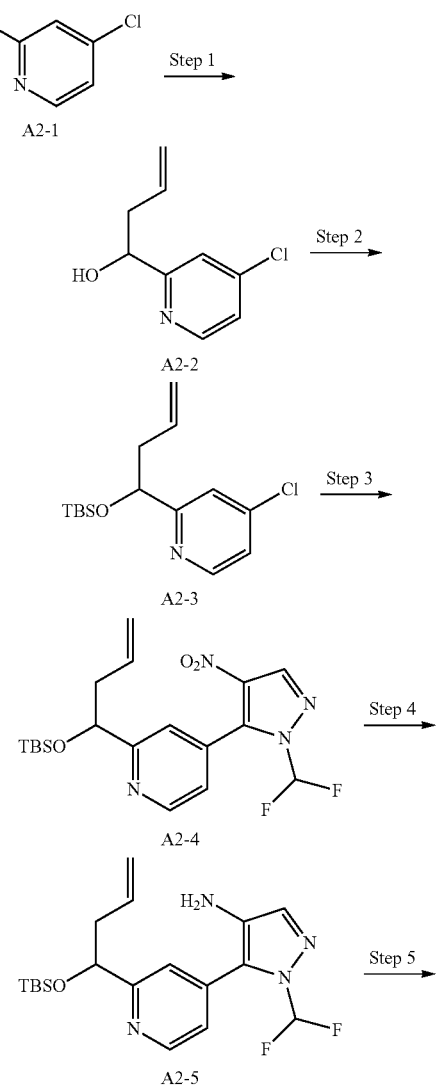

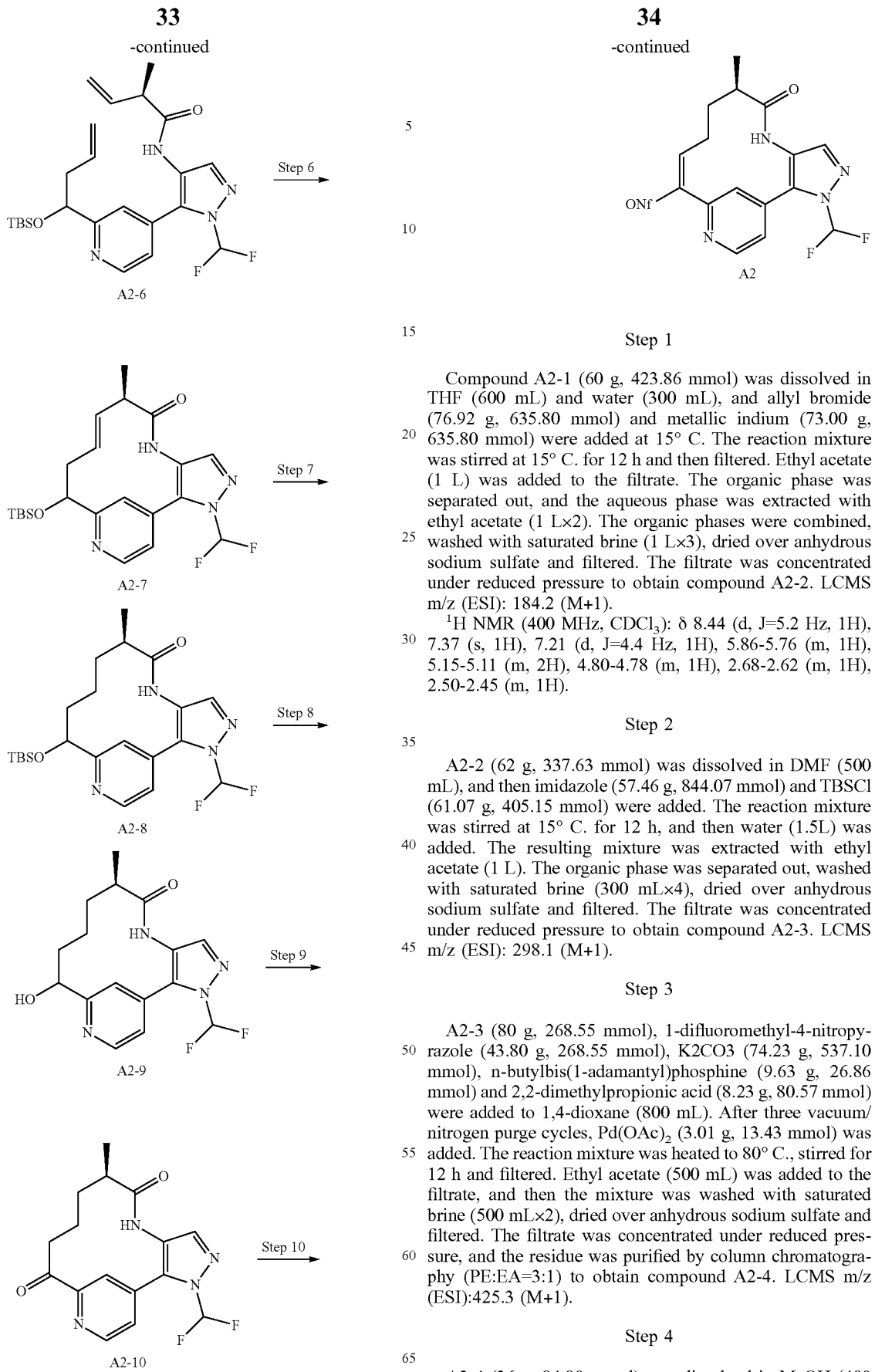

Step 1

Compound A2-1 (60 g, 423.86 mmol) was dissolved in THF (600 mL) and water (300 mL), and allyl bromide (76.92 g, 635.80 mmol) and metallic indium (73.00 g, 635.80 mmol) were added at 15° C. The reaction mixture was stirred at 15° C. for 12 h and then filtered. Ethyl acetate (1 L) was added to the filtrate. The organic phase was separated out, and the aqueous phase was extracted with ethyl acetate (1 L×2). The organic phases were combined, washed with saturated brine (1 L×3), dried over anhydrous sodium sulfate and filtered. The filtrate was concentrated under reduced pressure to obtain compound A2-2. LCMS m/z (ESI): 184.2 (M+1).
$^1$H NMR (400 MHz, CDCl$_3$): δ 8.44 (d, J=5.2 Hz, 1H), 7.37 (s, 1H), 7.21 (d, J=4.4 Hz, 1H), 5.86-5.76 (m, 1H), 5.15-5.11 (m, 2H), 4.80-4.78 (m, 1H), 2.68-2.62 (m, 1H), 2.50-2.45 (m, 1H).

Step 2

A2-2 (62 g, 337.63 mmol) was dissolved in DMF (500 mL), and then imidazole (57.46 g, 844.07 mmol) and TBSCl (61.07 g, 405.15 mmol) were added. The reaction mixture was stirred at 15° C. for 12 h, and then water (1.5L) was added. The resulting mixture was extracted with ethyl acetate (1 L). The organic phase was separated out, washed with saturated brine (300 mL×4), dried over anhydrous sodium sulfate and filtered. The filtrate was concentrated under reduced pressure to obtain compound A2-3. LCMS m/z (ESI): 298.1 (M+1).

Step 3

A2-3 (80 g, 268.55 mmol), 1-difluoromethyl-4-nitropyrazole (43.80 g, 268.55 mmol), K2CO3 (74.23 g, 537.10 mmol), n-butylbis(1-adamantyl)phosphine (9.63 g, 26.86 mmol) and 2,2-dimethylpropionic acid (8.23 g, 80.57 mmol) were added to 1,4-dioxane (800 mL). After three vacuum/nitrogen purge cycles, Pd(OAc)$_2$ (3.01 g, 13.43 mmol) was added. The reaction mixture was heated to 80° C., stirred for 12 h and filtered. Ethyl acetate (500 mL) was added to the filtrate, and then the mixture was washed with saturated brine (500 mL×2), dried over anhydrous sodium sulfate and filtered. The filtrate was concentrated under reduced pressure, and the residue was purified by column chromatography (PE:EA=3:1) to obtain compound A2-4. LCMS m/z (ESI):425.3 (M+1).

Step 4

A2-4 (36 g, 84.80 mmol) was dissolved in MeOH (400 mL), and then zinc power (55.45 g, 848.02 mmol) and solid NH4Cl (45.36 g, 848.02 mmol) were added at 0° C. The reaction mixture was stirred for 2 h and filtered. The filter cake was washed with MeOH (100 mL×3), and the filtrate was collected, concentrated under reduced pressure to remove most of the organic solvent, and then extracted with ethyl acetate (500 mL×2). The organic phases were combined, washed with saturated brine (300 mL×3), dried over anhydrous sodium sulfate and filtered. The filtrate was concentrated under reduced pressure to obtain compound A2-5. LCMS m/z (ESI):395.3 (M+1).

Step 5

A2-5 (46 g, 116.59 mmol), (2R)-2-methyl-3-butenoic acid (11.67 g, 116.59 mmol) and pyridine (8.45 g, 233.19 mmol) were dissolved in THF (500 mL). After three vacuum/nitrogen purge cycles, the reaction mixture was cooled to 0° C., and then T3P (111.29 g, 174.89 mmol, 50% ethyl acetate solution) was added. The reaction mixture was slowly warmed to 20° C. and stirred for 12 h. To the reaction mixture was then added ethyl acetate (200 mL), and the resulting mixture was washed with saturated brine (200 mL×3). The organic phase was separated out, dried over anhydrous sodium sulfate and filtered, and the filtrate was concentrated under reduced pressure. The residue was purified by column chromatography (PE:EA=3:1) to obtain compound A2-6. LCMS m/z (ESI):477.3 (M+1).

Step 6

A2-6 (26.00 g, 54.55 mmol) was dissolved in ethyl acetate (4 L), and then Hoveyda-Grubbs 2nd generation catalyst (10.25 g, 16.36 mmol) was added. After three vacuum/nitrogen cycles, the reaction mixture was then heated to 90° C. and stirred for 12 h. Saturated aqueous $Na_2CO_3$ solution (500 mL) was added to the reaction mixture to quench the reaction. The organic phase was separated out, washed with saturated brine (500 mL×2), dried over anhydrous sodium sulfate and filtered. The filtrate was concentrated under reduced pressure, and the residue was purified by column chromatography (PE:EA=1:1 (V:V)) to obtain compound A2-7. LCMS m/z (ESI):449.3 (M+1).

Step 7

A2-7 (21.00 g, 46.81 mmol) was dissolved in MeOH (1 L), and then palladium on carbon (10 g, 46.81 mmol, content: 10%) was added. The reaction mixture was stirred under hydrogen atmosphere (15 psi) at 20° C. for 24 h. The reaction mixture was filtered, and the filtrate was concentrated under reduced pressure to obtain compound A2-8. LCMS m/z (ESI):451.3 (M+1).

Step 8

A2-8 (20.00 g, 44.39 mmol) was dissolved in 1,4-dioxane (250 mL), and then $HC_{1/1,4}$-dioxane (263.16 mL, 4 M) was added. The reaction mixture was stirred at 15° C. for 12 h and then concentrated under reduced pressure. To the residue was added saturated aqueous $Na_2CO_3$ solution (50 mL), and then the resulting mixture was extracted with ethyl acetate (50 mL×4). The organic phases were combined, dried over anhydrous sodium sulfate and filtered. The filtrate was concentrated under reduced pressure to obtain compound A2-9. LCMS m/z (ESI):337.2 (M+1).

Step 9

A2-9 (8.5 g, 25.27 mmol) was dissolved in DMSO (50 mL), and IBX (14.15 g, 50.54 mmol) was added at 20° C.

The reaction mixture was stirred for 2 h. The reaction mixture was then poured into water (200 mL) and extracted with ethyl acetate (200 mL×3). The organic phases were combined, dried over anhydrous sodium sulfate and filtered. The filtrate was concentrated under reduced pressure to obtain compound A2-10. LCMS m/z (ESI):335.3 (M+1).

Step 10

A2-10 (8.5 g, 25.42 mmol) was dissolved in DMF (100 mL) and toluene (100 mL). The reaction mixture was cooled to −78° C. under nitrogen atmosphere, and then LiHMDS (63.56 mL, 1 M) was added. The reaction mixture was stirred at -78° C. for 0.5 h, and then perfluorobutanesulfonyl fluoride (22.74 g, 76.27 mmol) was added. The reaction mixture was slowly warmed to 15° C. and stirred for 0.5 h, and then saturated aqueous $NH_4Cl$ solution (100 mL) was added to quench the reaction. The resulting mixture and extracted with ethyl acetate (100 mL×2). The organic phases were combined, dried over anhydrous sodium sulfate and filtered. The filtrate was concentrated under reduced pressure, and the residue was purified by column chromatography (PE:EA=1:1) to obtain compound A2. LCMS m/z (ESI):617.0 (M+1).

EXAMPLE 1

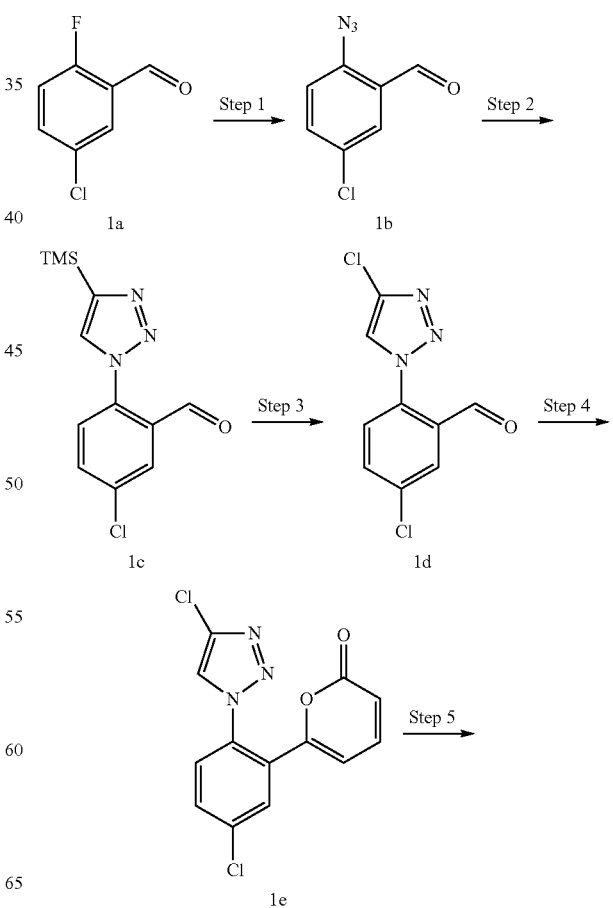

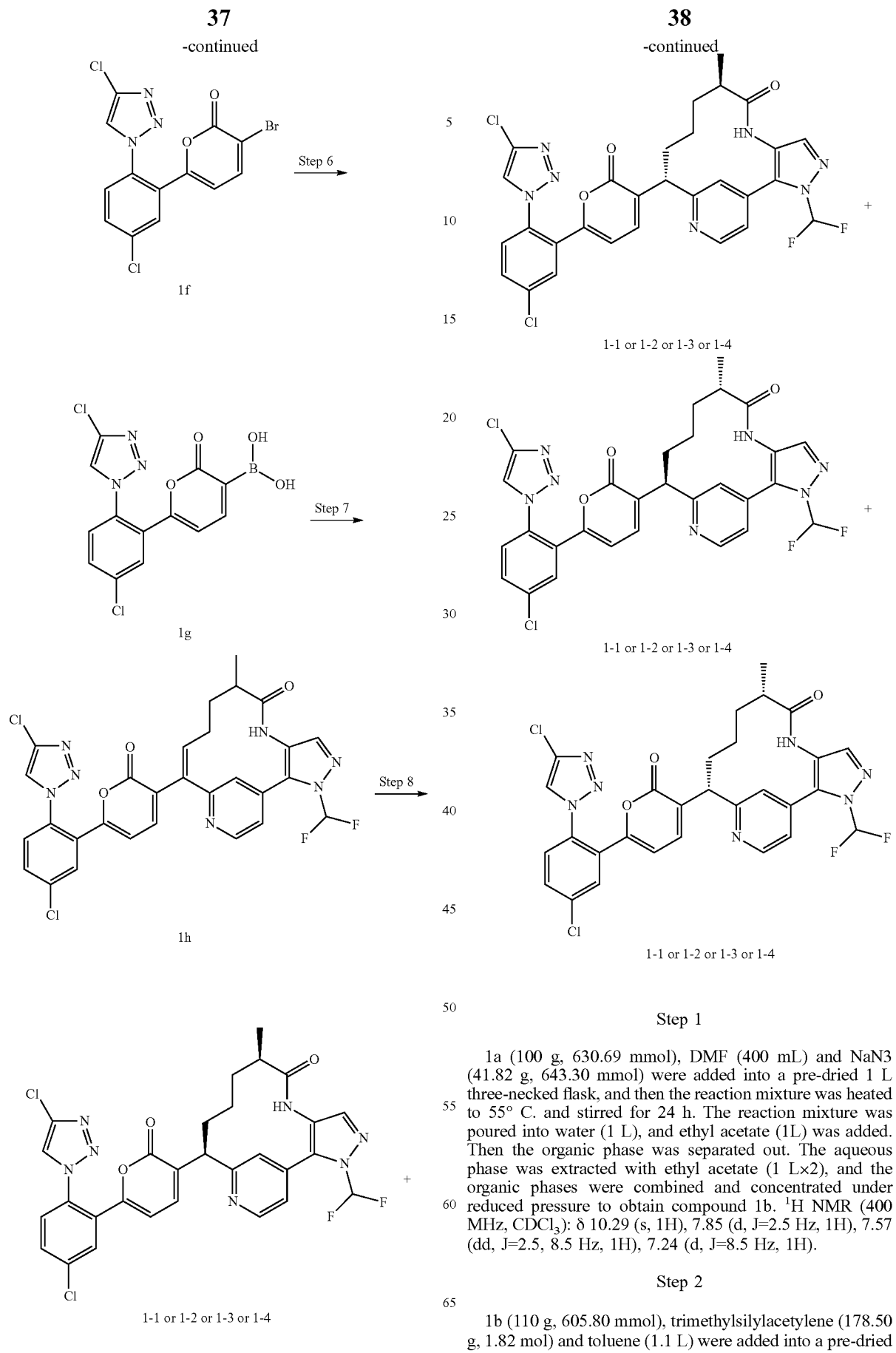

Step 1

1a (100 g, 630.69 mmol), DMF (400 mL) and NaN3 (41.82 g, 643.30 mmol) were added into a pre-dried 1 L three-necked flask, and then the reaction mixture was heated to 55° C. and stirred for 24 h. The reaction mixture was poured into water (1 L), and ethyl acetate (1L) was added. Then the organic phase was separated out. The aqueous phase was extracted with ethyl acetate (1 L×2), and the organic phases were combined and concentrated under reduced pressure to obtain compound 1b. $^1$H NMR (400 MHz, CDCl$_3$): δ 10.29 (s, 1H), 7.85 (d, J=2.5 Hz, 1H), 7.57 (dd, J=2.5, 8.5 Hz, 1H), 7.24 (d, J=8.5 Hz, 1H).

Step 2

1b (110 g, 605.80 mmol), trimethylsilylacetylene (178.50 g, 1.82 mol) and toluene (1.1 L) were added into a pre-dried 2 L flask, and the reaction mixture was stirred at 110° C. for 21 h and then concentrated under reduced pressure. The crude product was purified by column chromatography (PE:EA=20:1 to 2:1) to obtain compound 1c. LCMS m/z (ESI): 280.0 (M+1). $^{1}$H NMR (400 MHz, CDCl$_{3}$): δ 9.86 (s, 1H), 8.08 (d, J=2.4 Hz, 1H), 7.90 (s, 1H), 7.72 (dd, J=2.2, 8.4 Hz, 1H), 7.48 (d, J=8.4 Hz, 1H), 0.41 (s, 9H).

Step 3

1c (130 g, 464.62 mmol) and MeCN (3.5 L) were added into a pre-dried 5 L flask, and NCS (744.49 g, 5.58 mol) and KF (161.97 g, 2.79 mol) were added at 25° C. The reaction mixture was heated to 90° C. and reacted for 40 h. The reaction mixture was directly filtered and the filtrate was dried by rotary evaporation to obtain a crude product. To the crude product was added aqueous NaOH solution until the pH of the mixture was greater than 13, and then ethyl acetate (1 L) was added. The resulting mixture was stirred at 25° C. for half an hour. After the organic phase was separated out, the aqueous phase was extracted with ethyl acetate (1 L×3). The organic phases were combined and concentrated under reduced pressure, and the residue was purified by column chromatography (DCM) to obtain compound 1d. LCMS m/z (ESI): 241.9 (M+1). $^{1}$H NMR (400 MHz, CDCl$_{3}$): δ 9.88 (s, 1H), 8.09 (d, J=2.5 Hz, 1H), 7.94 (s, 1H), 7.76 (dd, 8.5 Hz, 1H), 7.49 (d, J=8.5 Hz, 1H).

Step 4

1d (36.70 g, 151.61 mmol), tricyclohexylphosphine (63.78 g, 227.42 mmol) and CHCl$_{3}$ (1.5 L) were added into a pre-dried flask, and then ethyl 2,3-butadienoate (17 g, 151.61 mmol) was added dropwise. After being sealed, the reaction mixture was heated to 65° C. and stirred for 4 h. The reaction mixture was concentrated under reduced pressure, and the crude product was purified by column chromatography (PE:EA=100:1 to 2:1) to obtain compound 1e. $^{1}$H NMR (400 MHz, CDCl$_{3}$): δ 7.83 (d, J=2.3 Hz, 1H), 7.76 (s, 1H), 7.62 (dd, J=2.3, 8.4 Hz, 1H), 7.46 (d, J=8.6 Hz, 1H), 7.27 (s, 1H), 6.32-6.27 (m, 1H), 5.94 (dd, J=0.8, 6.7 Hz, 1H).

Step 5

1e (24 g, 77.89 mmol), pyridinium bromide perbromide (74.73 g, 233.68 mmol) and AcOH (500 mL) were added into a pre-dried flask, and then the reaction mixture was stirred at 120° C. for 24 h. Ethyl acetate (200 mL) and petroleum ether (200 mL) were added to the reaction mixture. After the phase separation, the organic phase was separated out. The aqueous phase was extracted with a mixture of petroleum ether and ethyl acetate (1:1, 400 mL×3). The organic phases were combined and concentrated under reduced pressure. Petroleum ether (300 mL) was added to the residue, and the mixture was stirred for 10 min, with a solid precipitated. The solid was collected by filtration and dried to obtain compound 1f. LCMS m/z (ESI): 385.9 (M+1). $^{1}$H NMR (400 MHz, CDCl$_{3}$): δ 7.83 (d, J=2.3 Hz, 1H), 7.77 (s, 1H), 7.66-7.60 (m, 2H), 7.45 (d, J=8.4 Hz, 1H), 5.85 (d, J=7.2 Hz, 1H).

Step 6

1f (3 g, 7.75 mmol), bis(pinacolato)diboron (2.95 g, 11.63 mmol), KOAc (1.52 g, 15.50 mmol) and 1,4-dioxane (90 mL) were added into a pre-dried flask. After three vacuum/nitrogen purge cycles, Pd(dppf)Cl$_{2}$ (113.44 mg, 155.03 mol) was added. The reaction mixture was stirred at 80° C. for 5 h. After the reaction mixture was cooled to room temperature, the solid was removed by filtration, and the filtrate was concentrated under reduced pressure. The crude product was purified by preparative HPLC to obtain compound 1g. LCMS m/z (ESI): 352.0 (M+1). $^{1}$H NMR (400 MHz, DMSO-d$_{6}$): δ 8.91 (s, 1H), 8.01 (d, J=2.5 Hz, 1H), 7.93-7.86 (m, 2H), 7.82-7.77 (m, 1H), 6.64 (d, J=6.5 Hz, 1H).

Step 7

Compound 1g (481.44 mg, 1.37 mmol), intermediate A1 (0.58 g, 1.24 mmol) and Cs$_{2}$CO$_{3}$ (729.35 mg, 2.24 mmol) were dissolved in 1,4-dioxane (29 mL) and Pd(dppf)Cl$_{2}$ (101.56 mg, 124.36 μmol) was added under nitrogen atmosphere. The reaction mixture was reacted at 30° C. for 12 h and then filtered. Ethyl acetate (30 mL) and water (20 mL) were added to the filtrate. The organic phase was separated out, and the aqueous phase was extracted with ethyl acetate (20 mL×3). The organic phases were combined and concentrated under reduced pressure, and the residue was purified by column chromatography (PE:EA=20:1 to 0:1) to obtain compound 1 h. LCMS m/z (ESI): 624.1 (M+1).

Step 8

Raney nickel (274.41 mg, 3.20 mmol), THF (40 mL) and 1h (0.4 g, 640.59 μmol) were added into a hydrogenation flask, and then the reaction mixture was reacted at 25° C. for 10 min under hydrogen atmosphere (50 psi). The reaction mixture was directly filtered, and the filtrate was concentrated under reduced pressure. The residue was purified by thin layer chromatography (PE:EA=2.5:1) to obtain two diastereomers. Each isomer was then separated by SFC (separation column: DAICEL CHIRALPAK AD (250 mm×30 mm, 10 μm); mobile phase: isopropanol; gradient: isopropanol 50%-50%, 7 min) to obtain target compounds: compound 1-1 ($t_R$=1.89 min), compound 1-2 ($t_R$=2.31 min), compound 1-3 ($t_R$=1.93 min) and compound 1-4 ($t_R$=2.43 min).

Compound 1-1: LCMS m/z (ESI): 626.2 (M+1). $^{1}$H NMR (400 MHz, CDCl$_{3}$): δ 8.70 (d, J=5.0 Hz, 1H), 7.82 (d, J=2.0 Hz, 1H), 7.72 (s, 1H), 7.64 (s, 1H), 7.59 (dd, J=2.4, 8.4 Hz, 1H), 7.51-7.37 (m, 3H), 7.30 (t, J=58.8 Hz, 1H), 6.60 (s, 1H), 5.96 (d, J=7.0 Hz, 1H), 4.26 (br dd, J=4.6, 12.0 Hz, 1H), 2.57 (br dd, J=3.6, 6.6 Hz, 1H), 2.02-1.82 (m, 3H), 1.65-1.57 (m, 1H), 1.78-1.57 (m, 1H), 1.05 (d, J=6.6 Hz, 3H), 0.60 (br s, 2H).

Compound 1-2: LCMS m/z (ESI): 626.2 (M+1). $^{1}$H NMR (400 MHz, CDCl$_{3}$): δ 8.69 (d, J=5.0 Hz, 1H), 7.81 (d, J=2.0 Hz, 1H), 7.73 (s, 1H), 7.64 (s, 1H), 7.59 (dd, J=2.0, 8.6 Hz, 1H), 7.52-7.35 (m, 3H), 7.30 (t, J=58.8 Hz, 1H), 6.66 (s, 1H), 5.96 (d, J=7.0 Hz, 1H), 4.26 (br dd, J=4.4, 12.3 Hz, 1H), 2.57 (br dd, J=3.6, 6.6 Hz, 1H), 2.02-1.80 (m, 3H), 1.45-1.28 (m, 2H), 1.05 (d, J=7.0 Hz, 3H), 0.59 (br s, 1H).

Compound 1-3: LCMS m/z (ESI): 626.2 (M+1). $^{1}$H NMR (400 MHz, CDCl$_{3}$): δ 8.66 (d, J=5.0 Hz, 1H), 7.83 (d, J=2.0 Hz, 1H), 7.74 (s, 1H), 7.67 (s, 1H), 7.62-7.57 (m, 1H), 7.47-7.41 (m, 2H), 7.35 (br d, J=5.0 Hz, 1H), 7.29 (t, J=58.8 Hz, 1H), 7.14 (s, 1H), 6.59 (s, 1H), 5.98 (d, J=7.0 Hz, 1H), 4.26 (br dd, J=4.6, 12.0 Hz, 1H), 2.29-2.17 (m, 1H), 1.94-1.76 (m, 3H), 1.56-1.37 (m, 2H), 1.28 (d, J=6.6 Hz, 3H), 0.74-0.59 (m, 1H).

Compound 1-4: LCMS m/z (ESI): 626.2 (M+1). $^{1}$H NMR (400 MHz, CDCl$_{3}$): δ 8.66 (d, J=5.0 Hz, 1H), 7.83 (d, J=2.0 Hz, 1H), 7.73 (s, 1H), 7.67 (s, 1H), 7.63-7.56 (m, 2H), 7.44-7.42 (m, 2H), 7.35 (br s, 1H), 7.29 (t, J=58.8 Hz, 1H), 6.56 (s, 1H), 5.98 (d, J=7.0 Hz, 1H), 4.34-4.18 (m, 1H), 2.33-2.17 (m, 1H), 1.95-1.75 (m, 3H), 1.55-1.39 (m, 2H), 1.29 (d, J=7.0 Hz, 3H), 0.76-0.60 (m, 1H).

EXAMPLE 2
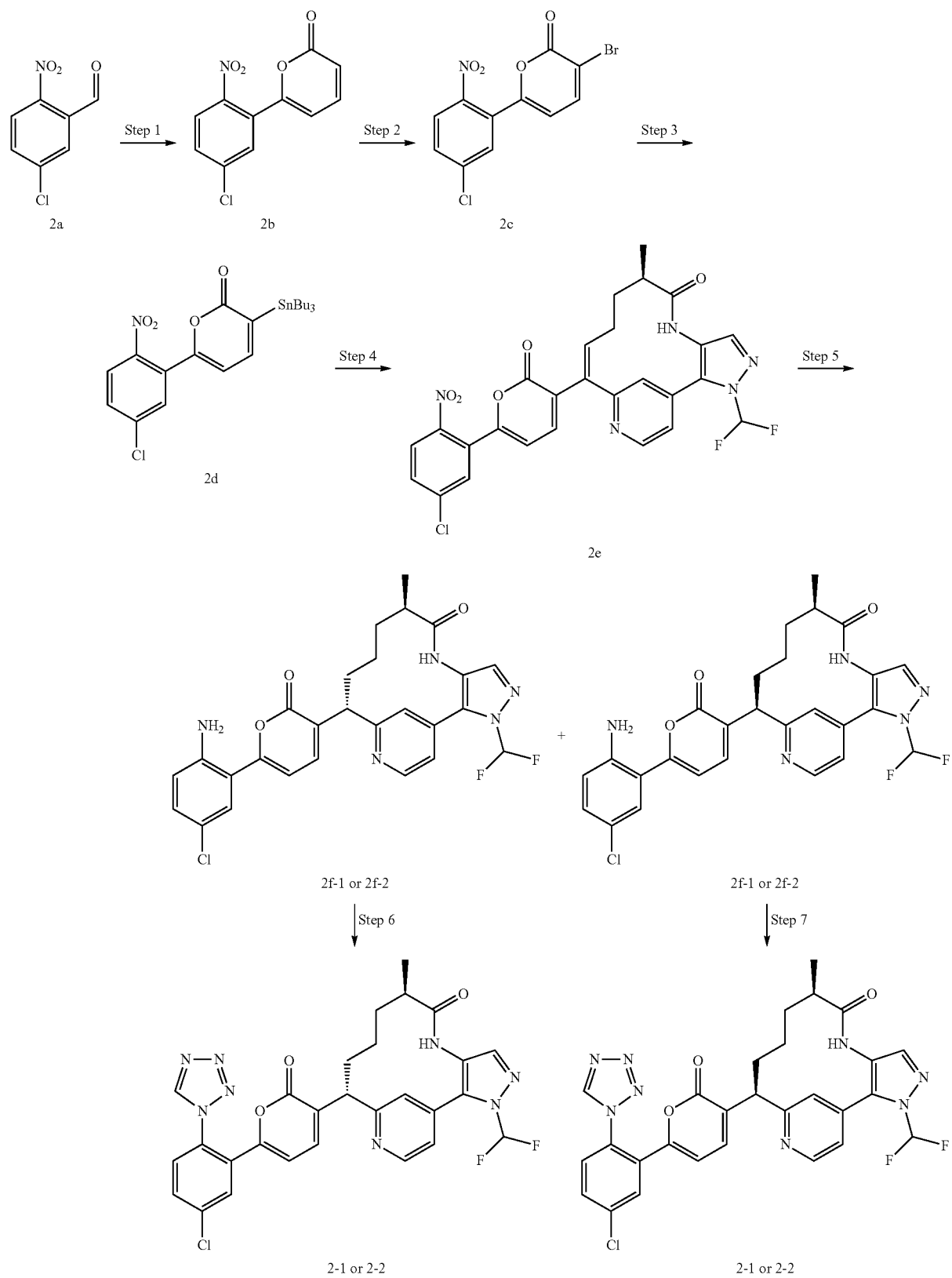

Step 1

Compound 2a (7 g, 37.72 mmol) was dissolved in CHCl₃ (70 mL), and then tricyclohexylphosphine (15.87 g, 56.58 mmol) and ethyl 2,3-butadienoate (4.65 g, 41.50 mmol) were added. The reaction mixture was heated to 65° C. and stirred for 3 h. The reaction mixture was concentrated under reduced pressure, and ethyl acetate (50 mL) and water (20 mL) were added to the residue. The organic phase was separated out, washed with saturated brine (20 mL×2), dried over anhydrous sodium sulfate and filtered. The filtrate was concentrated under reduced pressure, and the residue was purified by column chromatography (PE:EA=5:1 to 2:1) to obtain compound 2b.

Step 2

2b (2 g, 7.95 mmol) was dissolved in AcOH (50 mL), and then pyridinium bromide perbromide (12.71 g, 39.74 mmol) was added. The reaction mixture was heated to 120° C. and stirred for 12 h. The reaction mixture was concentrated under reduced pressure, and water (20 mL) was added to the residue, followed by extraction with ethyl acetate (20 mL×2). The extracts were combined, washed with saturated brine (20 mL×2), dried over anhydrous sodium sulfate and filtered. The filtrate was concentrated under reduced pressure, and the residue was purified by column chromatography (PE:EA=10:1 to 2:1) to obtain compound 2c. LCMS m/z (ESI): 330.1 (M+1).

Step 3

2c (1.1 g, 3.33 mmol), hexabutylditin (2.90 g, 4.99 mmol) and Pd(PPh₃)₄ (384.58 mg, 332.81 µmol) were dissolved in toluene (20 mL). After three vacuum/nitrogen purge cycles, the reaction mixture was heated to 100° C. and stirred for 12 h. To the reaction mixture was added ethyl acetate (40 mL), and the resulting mixture was washed with saturated brine (20 mL×3), dried over anhydrous sodium sulfate and filtered. The filtrate was concentrated under reduced pressure, and the residue was purified by column chromatography (PE:EA=5:1) to obtain compound 2d. LCMS m/z (ESI): 484.2 (M-57).

Step 4

2d (0.4 g, 739.83 µmol), intermediate A2 (456.03 mg, 739.83 µmol), Pd(PPh₃)₄ (128.24 mg, 110.97 µmol), CuCl (732.42 mg, 7.40 mmol) and LiCl (313.64 mg, 7.40 mmol) were dissolved in DMSO (20 mL). The reaction mixture was subjected to three vacuum/nitrogen purge cycles, then heated to 80° C. and stirred for 1 h. To the reaction mixture was added water (50 mL) to quench the reaction, and then the resulting mixture was extracted with ethyl acetate (50 mL×2). The organic phases were combined, washed with saturated brine (50 mL×2), dried over anhydrous sodium sulfate and filtered. The filtrate was concentrated under reduced pressure, and the residue was purified by column chromatography (DCM:EA=1:1) to obtain compound 2e. LCMS m/z (ESI): 568.2 (M+1).

Step 5

2e (0.14 g, 246.51 µmol) was dissolved in MeOH (15 mL), and then Raney nickel (14.47 mg, 246.51 µmol) was added. The reaction mixture was stirred under hydrogen atmosphere (30 psi) at 30° C. for 2 h. The reaction mixture was filtered, and the filtrate was concentrated under reduced pressure. The residue was purified by preparative thin layer chromatography (PE:EA:MeOH=4:4:1) to obtain diastereomers 2f-1 ($R_f$=0.70) and 2f-2 ($R_f$=0.63). LCMS m/z (ESI): 540.2 (M+1).

Step 6

2f-1 (0.04 g, 74.08 µmol) was dissolved in AcOH (3 mL), and then trimethyl orthoformate (78.61 mg, 740.80 µmol) and NaN₃ (85.35 mg, 740.80 µmol) were added. The reaction mixture was heated to 90° C. and stirred for 2 h, and water (10 mL) was added to quench the reaction. The resulting mixture was then extracted with ethyl acetate (20 mL×2). The extracts were combined, washed with saturated brine (20 mL×2), dried over anhydrous sodium sulfate and filtered. The filtrate was concentrated under reduced pressure, and the residue was purified by preparative HPLC (separation column: Shim-pack C₁₈ (25 mm×150 mm, 10 µm); mobile phase: (water (0.225% formic acid)—acetonitrile); gradient: acetonitrile 30-60%, 10 min) to obtain compound 2-1. LCMS m/z (ESI): 593.0 (M+1).
¹H NMR (400 MHz, CD₃OD): δ 9.52 (s, 1H), 8.61 (d, J=5.2 Hz, 1H), 7.95 (d, J=2.4 Hz, 1H), 7.76-7.73 (m, 2H), 7.69-7.59 (m, 4H), 7.43-7.41 (m, 1H), 6.52 (d, J=5.2 Hz, 1H), 4.21-4.16 (m, 1H), 2.72-2.69 (m, 1H), 2.03-1.54 m, 3H), 1.54 (br s, 1H), 1.35 (br s, 1H), 0.99 (d, J=6.8 Hz, 3H), 0.50 (br s, 1H).

Step 7

2f-2 (0.045 g, 83.34 µmol) was dissolved in AcOH (3 mL), and then trimethyl orthoformate (88.44 mg, 833.40 µmol) and TMSN₃ (96.01 mg, 833.40 µmol) were added. The reaction mixture was heated to 90° C. and stirred for 2 h, and water (10 mL) was added to quench the reaction. The resulting mixture was then extracted with ethyl acetate (20 mL×2). The extracts were combined, washed with saturated brine (20 mL×2), dried over anhydrous sodium sulfate and filtered. The filtrate was concentrated under reduced pressure, and the residue was purified by preparative HPLC (separation column: Shim-pack C₁₈ (25 mm×150 mm, 10 µm); mobile phase: (water (0.225% formic acid)—acetonitrile); gradient: acetonitrile 30-60%, 10 min) to obtain compound 2-2. LCMS m/z (ESI): 593.0 (M+1).
¹ NMR (400 MHz, CD₃OD): δ 9.52 (s, 1H), 8.58 (d, J=5.2 Hz, 1H), 7.96 (d, J=2.4 Hz, 1H), 7.82-7.73 (m, 2H), 7.70-7.50 (m, 4H), 7.40 (d, J=5.2 Hz, 1H), 6.51 (d, J=7.1 Hz, 1H), 4.17 (br dd, J=5.6, 10.8 Hz, 1H), 2.36-2.25 (m, 1H), 1.94-1.79 (m, 3H), 1.55-1.44 (m, 1H), 1.40-1.28 (m, 1H), 1.23 (d, J=6.8 Hz, 3H), 0.70 (m, 1H).

EXAMPLE 3

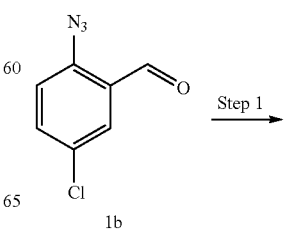

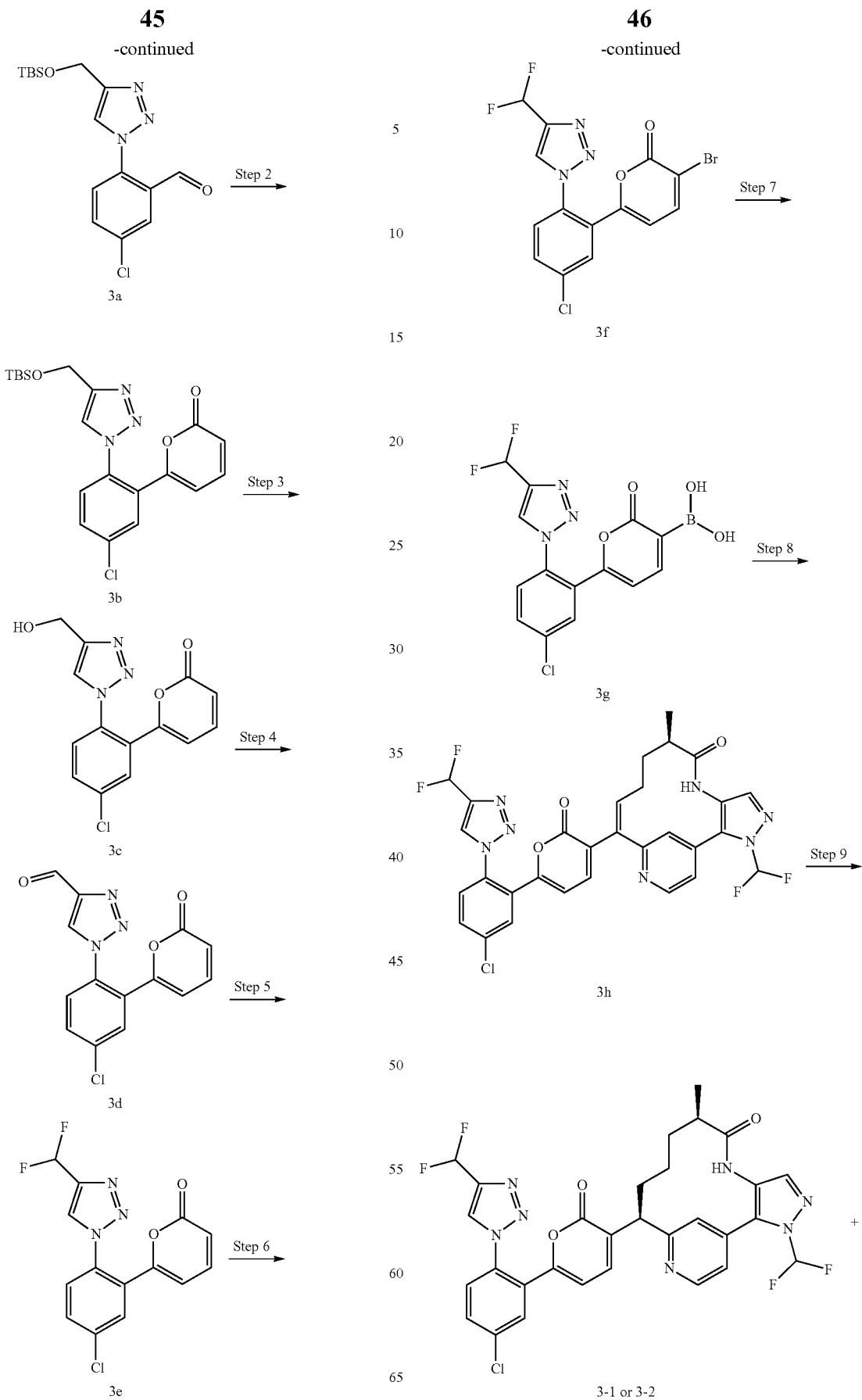

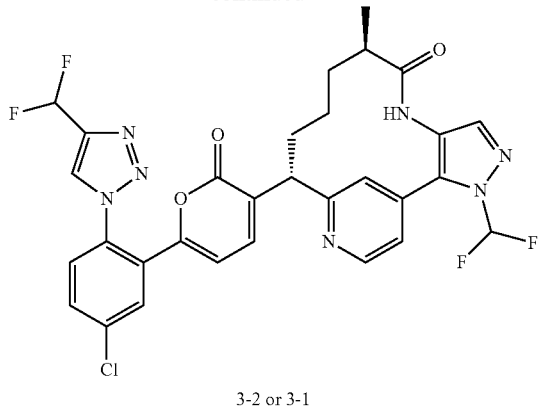 [SMILES: C[C@@H]1CCC[C@@H](c2ccc(-c3cc(Cl)ccc3-n3cc(C(F)F)nn3)oc2=O)c2cc(ccn2)-c2c(cnn2C(F)F)NC1=O]

3-2 or 3-1

Step 1

Compound 1b (10.39 g, 57.24 mmol), tert-butyldimethyl (2-propynyloxy)silane (6.5 g, 38.16 mmol), CuI (145.36 mg, 763.25 μmol) and triethylamine (77.23 mg, 763.25 μmol) were dissolved in acetonitrile (200 mL), and then the reaction mixture was stirred at 25° C. for 12 h under nitrogen atmosphere. The reaction mixture was concentrated under reduced pressure, and ethyl acetate (20 mL) was added to the residue. The mixture was stirred for 20 min and filtered, and the filter cake was dried under vacuum to obtain compound 3a. LCMS m/z (ESI): 352.3 (M+1).

Step 2

Compound 3a (2 g, 5.68 mmol), ethyl 2,3-butadienoate (764.71 mg, 6.82 mmol) and tricyclohexylphosphine (2.39 g, 8.53 mmol) were dissolved in chloroform (200 mL), and then the reaction mixture was heated to 50° C. under nitrogen atmosphere and stirred for 12 h. The reaction mixture was concentrated under reduced pressure, and the residue was purified by column chromatography (PE:EA=1:0 to 3:1) to obtain compound 3b. LCMS m/z (ESI): 418.1 (M+1).

Step 3

Compound 3b (1.4 g, 3.35 mmol) was dissolved in 1,4-dioxane (10 mL), and then hydrochloric acid/1,4-dioxane solution (10 mL, 1 M) was added. The reaction mixture was stirred at 50° C. for 20 min. The reaction mixture was filtered, and the filter cake was dried under vacuum to obtain compound 3c.

Step 4

Compound 3c (1 g, 3.29 mmol) was dissolved in dichloromethane (20 mL), and Dess-Martin reagent (2.09 g, 4.94 mmol) was added at 0° C. The reaction mixture was stirred at 0° C. for 1 h. The reaction mixture was filtered, and the filtrate was concentrated under reduced pressure to obtain compound 3d. LCMS m/z (ESI): 301.9 (M+1).

Step 5

Compound 3d (2.3 g, 7.62 mmol) was dissolved in dichloromethane (40 mL), and then diethylaminosulfur trifluoride (1.84 g, 11.44 mmol) was added. The reaction mixture was stirred at 25° C. for 2 h under nitrogen atmosphere. The reaction mixture was poured into saturated sodium bicarbonate solution (60 mL) at 0° C., and the resulting mixture was warmed to 20° C., stirred for 0.5 h, and then extracted with dichloromethane (40 mL×2). The organic phases were combined, washed with saturated brine (80 mL), dried over anhydrous sodium sulfate and filtered. The filtrate was concentrated under reduced pressure, and the residue was purified by column chromatography (PE:EA=1:0 to 2:1) to obtain compound 3e. LCMS m/z (ESI): 324.2 (M+1).

Step 6

Compound 3e (0.1 g, 308.95 μmol) and pyridinium bromide perbromide (296.42 mg, 926.84 μmol) were dissolved in acetic acid (2 mL), and then the reaction mixture was heated to 90° C. and reacted for 12 h. To the reaction mixture was added water (5 mL), and the resulting mixture was stirred for 10 min and filtered. The filter cake was dried under vacuum to obtain compound 3f. LCMS m/z (ESI): 404.2 (M+1).

Step 7

Compound 3f (60 mg, 149.04 μmol), bis(pinacolato)diboron (45.42 mg, 178.85 μmol), potassium acetate (29.25 mg, 298.08 μmol) and Pd(dppf)Cl$_2$ (2.18 mg, 2.98 μmol) were dissolved in 1,4-dioxane (2 mL). After three vacuum/nitrogen purge cycles, the reaction mixture was heated to 80° C. and reacted for 1.5 h to obtain compound 3g. LCMS m/z (ESI): 368.1 (M+1).

Step 8

Compound 3g (228 mg, 620.41 μmol), A2 (267.70 mg, 434.29 μmol), Pd(dppf)Cl$_2$ (9.08 mg, 12.41 μmol) and cesium carbonate (404.28 mg, 1.24 mmol) were added to 1,4-dioxane (1 mL). After three vacuum/nitrogen purge cycles, the reaction mixture was heated to 48° C. and reacted for 12 h. The reaction mixture was filtered, and the filtrate was concentrated under reduced pressure. The residue was purified by column chromatography (PE:EA=1:2 to EA:DCM=2:1) to obtain compound 3 h. LCMS m/z (ESI): 640.1 (M+1).

Step 9

Compound 3 h (290 mg, 453.13 μmol) was dissolved in THF (10 mL), and then Raney nickel (38.82 mg) was added under nitrogen atmosphere. The reaction mixture was stirred at 25° C. for 30 min under hydrogen atmosphere (50 psi), and then filtered. The filtrate was concentrated under reduced pressure, and the residue was purified by preparative TLC (EA) to obtain two fractions. Fraction 1 was purified by SFC (separation column: DAICEL CHIRALPAK IC (250 mm×30 mm, 10 μm); mobile phase: (0.1% ammonia-methanol); gradient: methanol 45%-45%, 1.9 min, 40 min), and then purified by preparative HPLC (separation column: Phenomenex Synergi C$_{18}$ (25 mm×150 mm, 10 μm); mobile phase: (water (0.225% formic acid)-acetonitrile); gradient: acetonitrile 36%-66%, 10 min) to obtain compound 3-1 ($t_R$=0.901 min); fraction 2 was purified by SFC (separation column: DAICEL CHIRALPAK IC (250 mm×30 mm, 10 μm); mobile phase: (0.1% ammonia-methanol); gradient: methanol 55%-55%, 2.5 min, 50 min), and then purified by preparative HPLC (separation column:

Phenomenex Synergi C18 (25 mm×150 mm, 10 μm); mobile phase: (water (0.225% formic acid)-acetonitrile); gradient: acetonitrile 36%-66%, 10 min) to obtain compound 3-2 ($t_R$=1.403 min).

Compound 3-1: LCMS m/z (ESI): 642.0 (M+1). $^1$H NMR (400 MHz, CD$_3$OD): δ 8.57-8.65 (m, 2H), 7.92 (d, J=2.40 Hz, 1H), 7.79-7.50 (m, 6H), 7.42 (d, J=4.80 Hz, 1H), 7.12-6.85 (m, 1H), 6.43 (d, J=6.80 Hz, 1H), 4.19 (dd, J=4.00, 12.40 Hz, 1H), 2.69 (m, 1H), 1.80-2.08 (m, 3H), 1.49-1.62 (m, 1H), 1.28-1.40 (m, 1H), 0.98 (d, J=6.80 Hz, 3H), 0.50 (br s, 1H).

Compound 3-2: LCMS m/z (ESI): 642.0 (M+1). $^1$H NMR (400 MHz, CD$_3$OD): δ 8.55-8.65 (m, 2H), 7.93 (d, J=2.00 Hz, 1H), 7.72-7.57 (m, 6H), 7.40 (d, J=4.80 Hz, 1H), 7.13-6.85 (m, 1H), 6.44 (d, J=7.20 Hz, 1H), 4.17 (dd, J=4.00, 11.20 Hz, 1H), 2.26-2.37 (m, 1H), 1.78-1.94 (m, 3H), 1.49 (m, 1H), 1.27-1.39 (m, 1H), 1.22 (d, J=6.80 Hz, 3H), 0.70 (m, 1H).

EXAMPLE 4

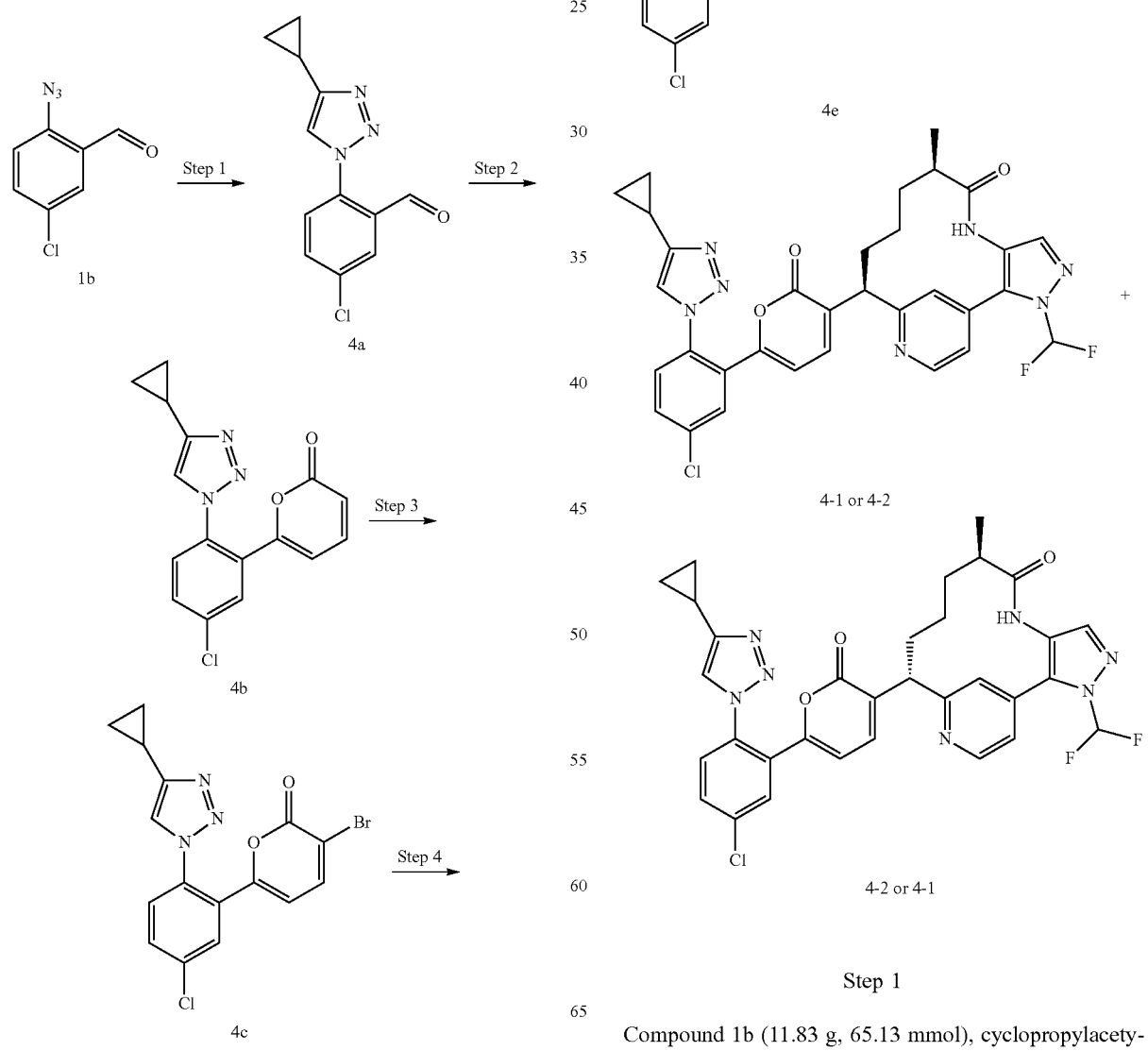

Step 1

Compound 1b (11.83 g, 65.13 mmol), cyclopropylacetylene (4.1 g, 43.42 mmol), CuI (165.38 mg, 868.37 μmol) and triethylamine (87.87 mg, 868.37 μmol) were dissolved in acetonitrile (150 mL), and then the reaction mixture was stirred at 25° C. for 24 h under nitrogen atmosphere. The reaction mixture was concentrated under reduced pressure, and the residue was purified by column chromatography (PE:EA=1:0 to 5:1) to obtain compound 4a.

Step 2

Compound 4a (2.1 g, 8.48 mmol), ethyl 2,3-butadienoate (950.68 mg, 8.48 mmol) and tricyclohexylphosphine (3.57 g, 12.72 mmol) were dissolved in chloroform (20 mL), and then the reaction mixture was heated to 60° C. under nitrogen atmosphere and reacted for 4 h. The reaction mixture was concentrated under reduced pressure, and the residue was purified by column chromatography (PE:EA=1:0 to 2:1) to obtain compound 4b. LCMS m/z (ESI): 314.5 (M+1).

Step 3

Compound 4b (5 g, 15.94 mmol) and pyridinium bromide perbromide (15.29 g, 47.81 mmol) were dissolved in acetic acid (50 mL), and then the reaction mixture was heated to 90° C. and reacted for 12 h. To the reaction mixture was then added ethyl acetate (100 mL), and the resulting mixture was washed with water (600 mL×2). The organic phase was separated out, washed with saturated brine (200 mL), dried over anhydrous sodium sulfate and filtered. The filtrate was concentrated under reduced pressure, and the residue was purified by column chromatography (PE:EA=1:0 to 3:1) to obtain compound 4c. LCMS m/z (ESI): 393.8 (M+1).

Step 4

Compound 4c (0.1 g, 254.69 μmol), bis(pinacolato)diboron (77.61 mg, 305.63 μmol), potassium acetate (49.99 mg, 509.38 μmol) and Pd(dppf)Cl$_2$ (3.73 mg, 5.09 μmol) were dissolved in 1,4-dioxane (1 mL). After three vacuum/nitrogen purge cycles, the reaction mixture was heated to 80° C. and reacted for 2 h to obtain compound 4d.

Step 5

Compound 4d (182 mg, 509.01 μmol), A2 (219.63 mg, 356.31 μmol), Pd(dppf)Cl$_2$ (7.45 mg, 10.18 μmol) and cesium carbonate (331.69 mg, 1.02 mmol) were added to 1,4-dioxane (1 mL). After three vacuum/nitrogen purge cycles, the reaction mixture was heated to 48° C. and reacted for 12 h. The reaction mixture was filtered, and the filtrate was concentrated under reduced pressure. The residue was purified by column chromatography (PE:EA=3:1 to EA:DCM=2:1) to obtain compound 4e. LCMS m/z (ESI): 630.1 (M+1).

Step 6

Compound 4e (450.00 mg, 714.24 μmol) was dissolved in THF (10 mL), and then Raney nickel (61.19 mg) was added under nitrogen atmosphere. The reaction mixture was stirred at 25° C. for 30 min under hydrogen atmosphere (50 psi), and then filtered. The filtrate was concentrated under reduced pressure, and the residue was purified by preparative TLC (EA) to obtain two fractions. Fraction 1 was purified by SFC (separation column: DAICEL CHIRALPAK IC (250 mm×30 mm, 10 μm); mobile phase: (0.1% ammonia-methanol); gradient: methanol 60%-60%, 2.1 min, 50 min), and then purified by preparative HPLC (separation column: Shim-pack C$_8$ (25 mm×150 mm, 10 μm); mobile phase: (water (0.225% formic acid)—acetonitrile); gradient: acetonitrile 40%-70%, 10 min) to obtain compound 4-1 ($t_R$=1.231 min); fraction 2 was purified by SFC (separation column: DAICEL CHIRALPAK IC (250 mm×30 mm, 10 μm); mobile phase: (0.1% ammonia—methanol); gradient: methanol 70%-70%, 3.5 min, 40 min), and then purified by preparative HPLC (separation column: Shim-pack C18 (25 mm×150 mm, 10 μm); mobile phase: (water (0.225% formic acid)—acetonitrile); gradient: acetonitrile 38%-68%, 10 min) to obtain compound 4-2 ($t_R$=1.875 min). Compound 4-1: LCMS m/z (ESI): 632.2 (M+1). $^1$H NMR (400 MHz, CDCl$_3$): δ 8.66 (d, J=4.80 Hz, 1H), 7.79 (d, J=2.40 Hz, 1H), 7.59 (s, 1H), 7.54 (dd, J=2.40, 8.80 Hz, 1H), 7.39~7.28 (m, 6H), 7.14 (s, 1H), 5.86 (d, J=7.20 Hz, 1H), 4.23 (dd, J=4.00, 12.40 Hz, 1H), 2.57 (m, 1H), 1.90-2.03 (m, 3H), 1.83-1.88 (m, 1H), 1.47-1.60 (m, 1H), 1.34 (m, 1H), 0.96-1.04 (m, 5H), 0.82-0.89 (m, 2H), 0.54 (br s, 1H).

Compound 4-2: LCMS m/z (ESI): 632.2 (M+1). $^1$H NMR (400 MHz, CDCl$_3$): δ 8.63 (d, J=5.20 Hz, 1H), 7.80 (d, J=2.00 Hz, 1H), 7.63 (s, 1H), 7.52-7.58 (m, 2H), 7.38-7.13 (m, 5H), 6.97 (s, 1H), 5.86 (d, J=7.20 Hz, 1H), 4.24 (dd, J=4.40, 12.40 Hz, 1H), 2.17-2.29 (m, 1H), 1.97-2.01 (m, 1H), 1.79-1.89 (m, 3H), 1.32-1.53 (m, 2H), 1.25 (d, J=6.80 Hz, 3H), 0.95-1.02 (m, 2H), 0.82-0.89 (m, 2H), 0.58-0.71 (m, 1H).

EXAMPLE 5

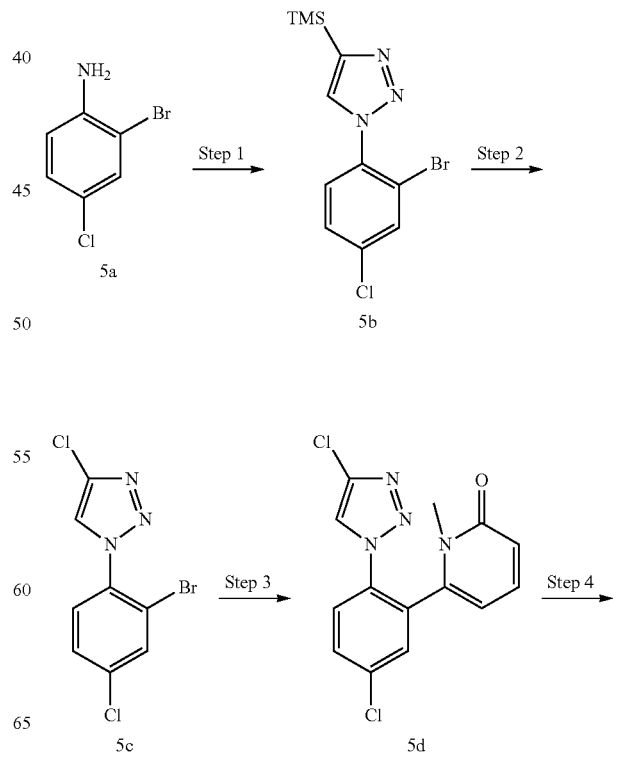

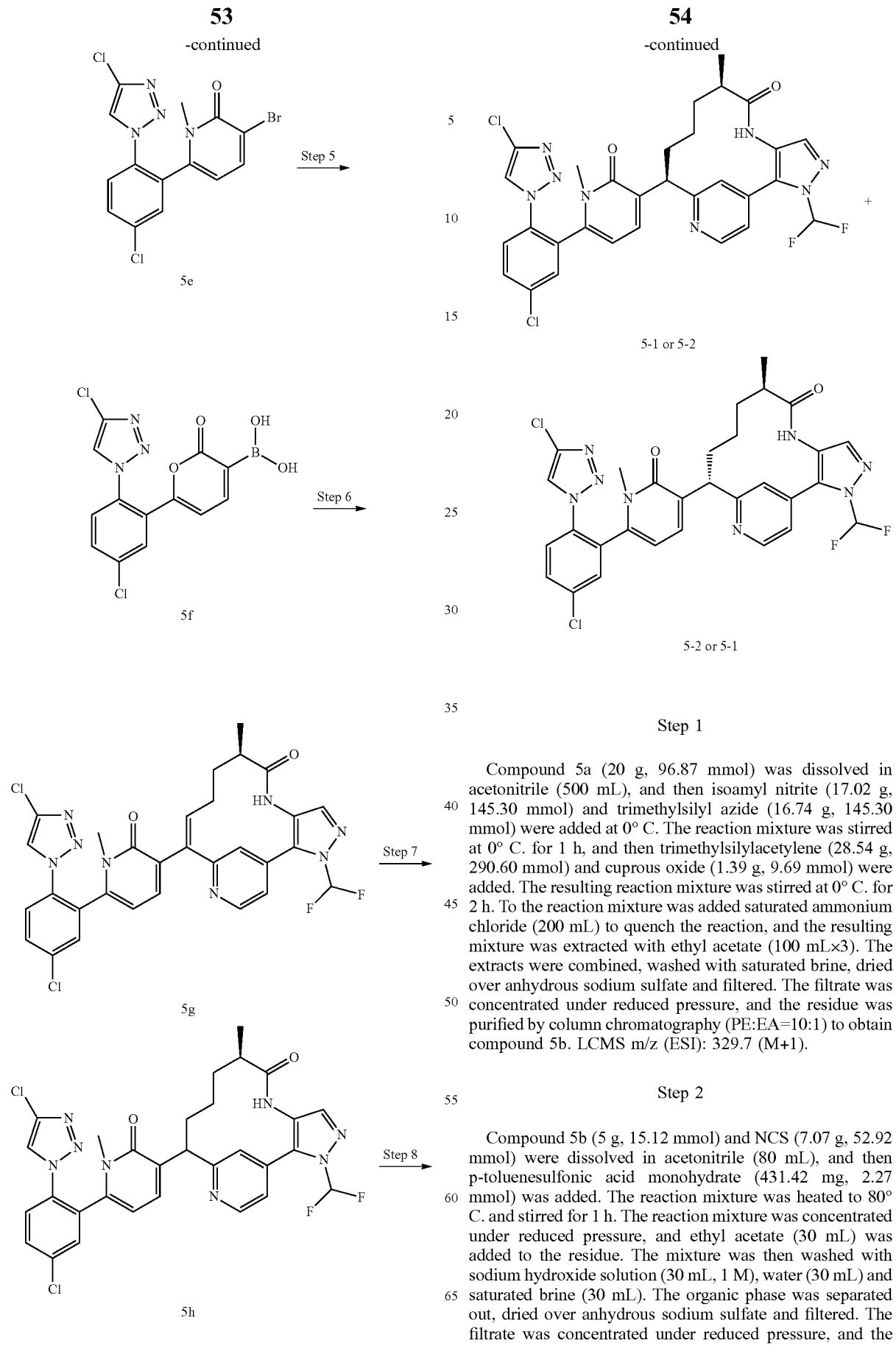

Step 1

Compound 5a (20 g, 96.87 mmol) was dissolved in acetonitrile (500 mL), and then isoamyl nitrite (17.02 g, 145.30 mmol) and trimethylsilyl azide (16.74 g, 145.30 mmol) were added at 0° C. The reaction mixture was stirred at 0° C. for 1 h, and then trimethylsilylacetylene (28.54 g, 290.60 mmol) and cuprous oxide (1.39 g, 9.69 mmol) were added. The resulting reaction mixture was stirred at 0° C. for 2 h. To the reaction mixture was added saturated ammonium chloride (200 mL) to quench the reaction, and the resulting mixture was extracted with ethyl acetate (100 mL×3). The extracts were combined, washed with saturated brine, dried over anhydrous sodium sulfate and filtered. The filtrate was concentrated under reduced pressure, and the residue was purified by column chromatography (PE:EA=10:1) to obtain compound 5b. LCMS m/z (ESI): 329.7 (M+1).

Step 2

Compound 5b (5 g, 15.12 mmol) and NCS (7.07 g, 52.92 mmol) were dissolved in acetonitrile (80 mL), and then p-toluenesulfonic acid monohydrate (431.42 mg, 2.27 mmol) was added. The reaction mixture was heated to 80° C. and stirred for 1 h. The reaction mixture was concentrated under reduced pressure, and ethyl acetate (30 mL) was added to the residue. The mixture was then washed with sodium hydroxide solution (30 mL, 1 M), water (30 mL) and saturated brine (30 mL). The organic phase was separated out, dried over anhydrous sodium sulfate and filtered. The filtrate was concentrated under reduced pressure, and the residue was purified by column chromatography (PE: EA=20:1 to 10:1) to obtain compound 5c. LCMS m/z (ESI): 293.9 (M+1).

Step 3

1-methyl-6-(tributylstannyl)pyridin-2(1H)-one (3.69 g, 9.27 mmol) and compound 5c (2.23 g, 7.60 mmol) were dissolved in toluene (60 mL), and then Pd (PPh$_3$)$_2$Cl$_2$ (650.48 mg, 926.74 μmol) was added under nitrogen atmosphere. The reaction mixture was heated to 130° C., stirred for 13 h and filtered. The filter cake was washed with ethyl acetate (10 mL×3) and a mixed solution of dichloromethane/methanol (2:1, 10 mL×3). The filtrate and washings were combined and concentrated under reduced pressure, and the residue was purified by column chromatography (PE: EA=10:1 to 5:1 to DCM: EA=1:1) to obtain compound 5d. LCMS m/z (ESI): 320.9 (M+1).

Step 4

Compound 5d (1.42 g, 3.08 mmol) and pyridinium bromide perbromide (986.17 mg, 3.08 mmol) were dissolved in acetic acid (30 mL), and then the reaction mixture was heated to 90° C. under nitrogen atmosphere and reacted for 4 h. The reaction mixture was poured into water (60 mL), and then ethyl acetate (20 mL) was added. The resulting reaction mixture was extracted with ethyl acetate (20 mL×3). The organic phases were combined, washed with saturated brine (50 mL×2), dried over anhydrous sodium sulfate and filtered. The filtrate was concentrated under reduced pressure, and the residue was slurried with ethyl acetate (10 mL) at 25° C. for 15 min, filtered and dried to obtain compound 5e. LCMS m/z (ESI): 401.0 (M+1).

Step 5

Compound 5e (0.35 g, 711.10 μmol), bis(pinacolato)diboron (361.15 mg, 1.42 mmol), potassium acetate (139.58 mg, 1.42 mmol) and Pd(dppf)Cl$_2$ (31.22 mg, 42.67 μmol) were dissolved in 1,4-dioxane (2 mL). After three vacuum/nitrogen purge cycles, the reaction mixture was heated to 80° C., and reacted for 0.5 h to obtain compound 5f. LCMS m/z (ESI): 365.3 (M+1).

Step 6

Compound 5f (260 mg, 712.37 μmol), A2 (263.46 mg, 427.42 μmol), Pd(dppf)Cl$_2$ (52.12 mg, 71.24 μmol) and cesium carbonate (464.21 mg, 1.42 mmol) were added to 1,4-dioxane (1.5 mL). After three vacuum/nitrogen purge cycles, the reaction mixture was heated to 50° C. and reacted for 12 h. The reaction mixture was diluted with ethyl acetate (30 mL) and then filtered. The filter cake was washed with ethyl acetate (10 mL×4), and the filtrate and the washings were combined and concentrated under reduced pressure. The residue was purified by column chromatography (PE: EA=2:1 to EA:DCM=1:1) to obtain compound 5g. LCMS m/z (ESI): 637.4 (M+1).

Step 7

Compound 5g (0.21 g, 329.43 μmol) was dissolved in THF (20 mL), and then chloroform (0.2 mL) was added. Raney nickel (282.24 mg) was added under nitrogen atmosphere, and then the reaction mixture was stirred at 25° C. for 0.5 h under hydrogen atmosphere (45 psi) and filtered. The filter cake was washed with ethyl acetate (10 mL×4), and the filtrate and washings were combined and concentrated under reduced pressure. The residue was purified by preparative HPLC (separation column: Phenomenex Synergi C$_{18}$ (25 mm×150 mm, 10 μm); mobile phase: (water (0.225% formic acid)—acetonitrile); gradient: acetonitrile 31%-61%, 10 min) to obtain compound 5 h. LCMS m/z (ESI): 639.2 (M+1).

Step 8

Compound 5 h (70 mg, 167.96 μmol) was separated by SFC (separation column: DAICEL CHIRALPAK IC (250 mm×30 mm, 10 μm); mobile phase: (0.1% ammonia—methanol); gradient: methanol 50%-50%, 4.1 min) to obtain compound 5-1 (t$_R$=1.090 min) and compound 5-2 (t$_R$=2.538 min). Compound 5-1: LCMS m/z (ESI):639.2 (M+1). $^1$H NMR (400 MHz, CD$_3$OD): δ 8.62-8.53 (m, 1H), 8.37-8.17 (m, 1H), 7.82-7.78 (m, 1H), 7.77-7.72 (m, 3H), 7.69-7.61 (m, 2H), 7.59-7.49 (m, 1H), 7.40 (br d, J=3.4 Hz, 1H), 6.29-6.19 (m, 1H), 4.40 (ddd, J=4.2, 7.8, 12.4 Hz, 1H), 3.20 (d, J=15.4 Hz, 3H), 2.76-2.67 (m, 1H), 2.14-1.98 (m, 2H), 1.92-1.77 (m, 1H), 1.63-1.48 (m, 1H), 1.42-1.31 (m, 1H), 0.99 (d, J=6.8 Hz, 3H), 0.51 (br s, 1H). Compound 5-2: LCMS m/z (ESI):639.2 (M+1). $^1$H NMR (400 MHz, CD$_3$OD): δ 8.57 (br dd, J=5.0, 19.8 Hz, 1H), 8.39-8.17 (m, 1H), 7.82-7.73 (m, 4H), 7.69-7.59 (m, 3H), 7.43 (br s, 1H), 6.35-6.20 (m, 1H), 4.45-4.31 (m, 1H), 3.24-3.13 (m, 3H), 2.38-2.26 (m, 1H), 1.87 (br d, J=9.4 Hz, 2H), 1.51 (br d, J=2.8 Hz, 1H), 1.29 (s, 2H), 1.25 (dd, J=4.0, 6.8 Hz, 3H), 0.73 (br d, J=11.2 Hz, 1H).

EXAMPLE 6

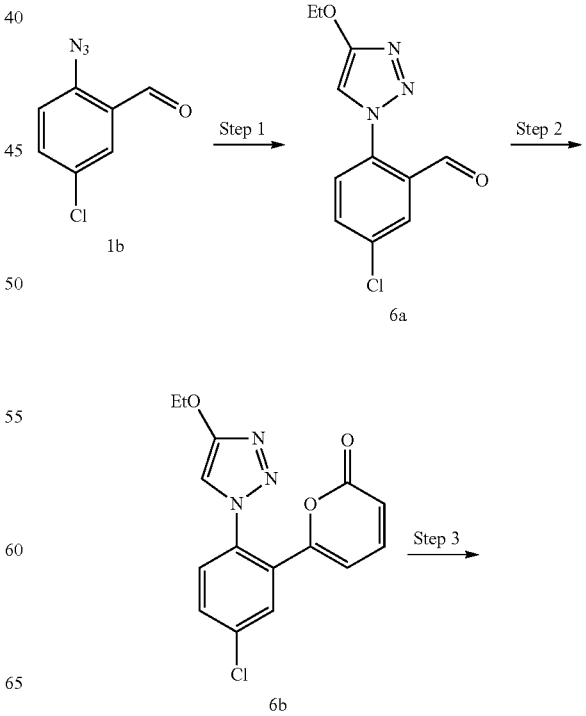

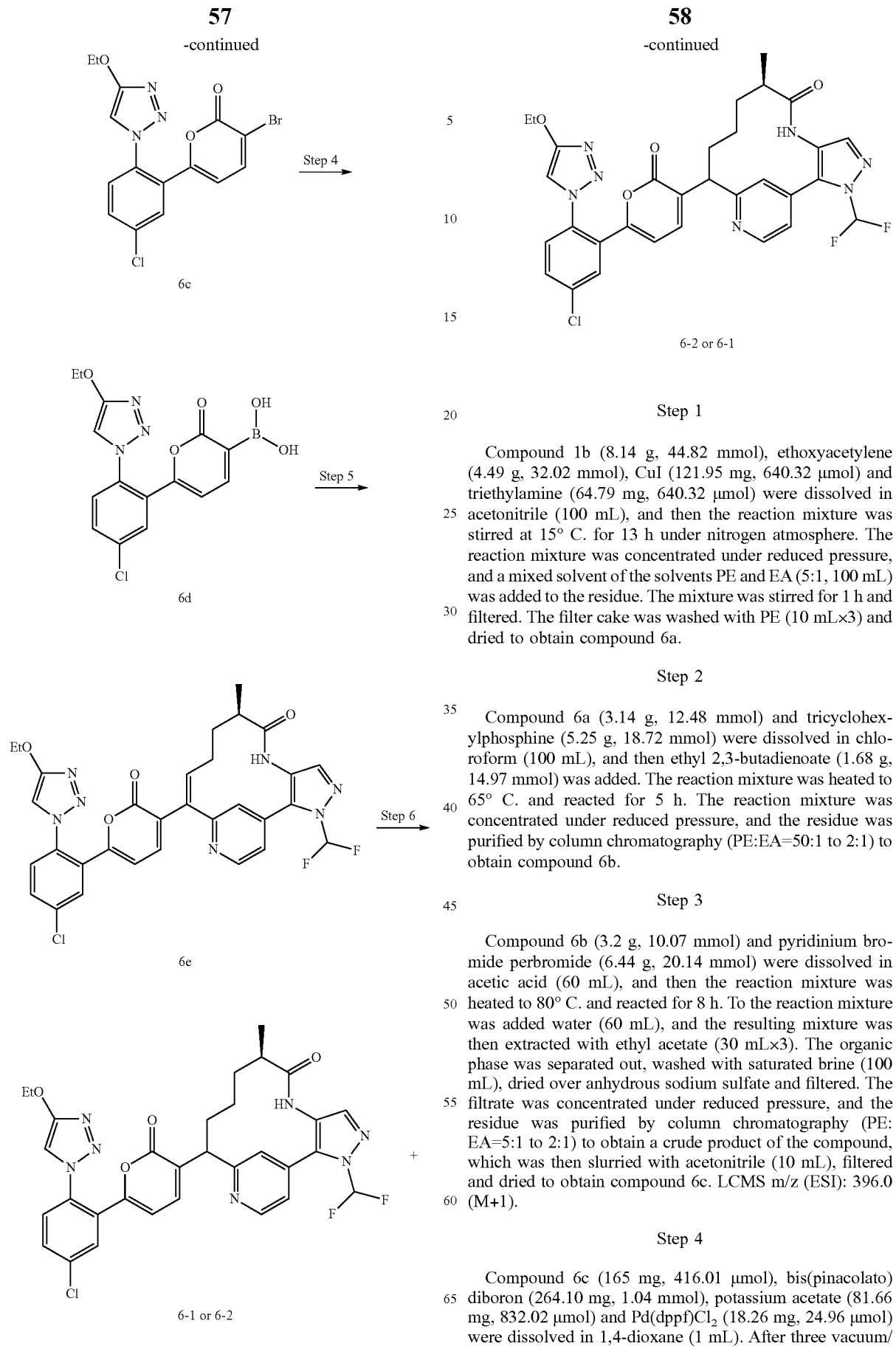

Step 1

Compound 1b (8.14 g, 44.82 mmol), ethoxyacetylene (4.49 g, 32.02 mmol), CuI (121.95 mg, 640.32 μmol) and triethylamine (64.79 mg, 640.32 μmol) were dissolved in acetonitrile (100 mL), and then the reaction mixture was stirred at 15° C. for 13 h under nitrogen atmosphere. The reaction mixture was concentrated under reduced pressure, and a mixed solvent of the solvents PE and EA (5:1, 100 mL) was added to the residue. The mixture was stirred for 1 h and filtered. The filter cake was washed with PE (10 mL×3) and dried to obtain compound 6a.

Step 2

Compound 6a (3.14 g, 12.48 mmol) and tricyclohexylphosphine (5.25 g, 18.72 mmol) were dissolved in chloroform (100 mL), and then ethyl 2,3-butadienoate (1.68 g, 14.97 mmol) was added. The reaction mixture was heated to 65° C. and reacted for 5 h. The reaction mixture was concentrated under reduced pressure, and the residue was purified by column chromatography (PE:EA=50:1 to 2:1) to obtain compound 6b.

Step 3

Compound 6b (3.2 g, 10.07 mmol) and pyridinium bromide perbromide (6.44 g, 20.14 mmol) were dissolved in acetic acid (60 mL), and then the reaction mixture was heated to 80° C. and reacted for 8 h. To the reaction mixture was added water (60 mL), and the resulting mixture was then extracted with ethyl acetate (30 mL×3). The organic phase was separated out, washed with saturated brine (100 mL), dried over anhydrous sodium sulfate and filtered. The filtrate was concentrated under reduced pressure, and the residue was purified by column chromatography (PE:EA=5:1 to 2:1) to obtain a crude product of the compound, which was then slurried with acetonitrile (10 mL), filtered and dried to obtain compound 6c. LCMS m/z (ESI): 396.0 (M+1).

Step 4

Compound 6c (165 mg, 416.01 μmol), bis(pinacolato)diboron (264.10 mg, 1.04 mmol), potassium acetate (81.66 mg, 832.02 μmol) and Pd(dppf)Cl$_2$ (18.26 mg, 24.96 μmol) were dissolved in 1,4-dioxane (1 mL). After three vacuum/ nitrogen purge cycles, the reaction mixture was heated to 80° C. and reacted for 1.5 h to obtain compound 6d. LCMS m/z (ESI): 362.0 (M+1).

Step 5

Compound 6d (150 mg, 414.89 μmol), A2 (179.60 mg, 290.42 μmol), Pd(dppf)Cl$_2$ (30.36 mg, 41.49 μmol) and cesium carbonate (270.36 mg, 829.77 μmol) were added to 1,4-dioxane (1 mL). After three vacuum/nitrogen purge cycles, the reaction mixture was heated to 50° C. and reacted for 12 h. The reaction mixture was filtered, and the filter cake was washed with ethyl acetate (10 mL×3). The filtrates were combined and concentrated under reduced pressure, and the residue was purified by column chromatography (PE: EA=3:1 to EA:DCM=1:1) to obtain compound 6e. LCMS m/z (ESI): 634.2 (M+1).

Step 6

Compound 6e (210 mg, 331.21 μmol) was dissolved in THF (20 mL), and then Raney nickel (28.38 mg) was added under nitrogen atmosphere. The reaction mixture was stirred at 25° C. for 30 min under hydrogen atmosphere (45 psi), and then filtered. The filtrate was concentrated under reduced pressure, and the residue was purified by preparative TLC (DCM:EA=1:1) to obtain 2 fractions. Fraction 1 was purified by SFC (separation column: DAICEL CHIRALPAK IC (250 mm×30 mm, 10 μm); mobile phase: (0.1% ammonia—methanol); gradient: methanol 70%-70%, 2.7 min, 40 min), and then purified by preparative HPLC (separation column: Shim-pack C18 (25 mm×150 mm, 10 μm); mobile phase: (water (0.225% formic acid)—acetonitrile); gradient: acetonitrile 38%-68%, 10 min) to obtain compound 6-1 ($t_R$=1.860 min); fraction 2 was purified by SFC (separation column: DAICEL CHIRALPAK IC (250 mm×30 mm, 10 pm), mobile phase: (0.1% ammonia—methanol); gradient: methanol 70%-70%, 2.8 min, 40 min) to obtain compound 6-2 ($t_R$=1.179 min).

Compound 6-1: LCMS m/z (ESI): 636.3 (M+1). $^1$H NMR (400 MHz, CD$_3$OD): δ 8.58 (d, J=4.8 Hz, 1H), 7.89 (d, J=2.0 Hz, 1H), 7.77 (s, 1H), 7.76 (s, 1H), 7.71-7.56 (m, 5H), 7.42 (br s, 1H), 6.40 (d, J=7.6 Hz, 1H), 4.55 (s, 1H), 4.16-4.21 (m, 2H), 2.31-2.34 (m, 1H), 1.85-1.91 (m, 3H), 1.45-1.55 (m, 1H), 1.27-1.40 (m, 4H), 1.23 (d, J=7.2 Hz, 3H), 0.70 (br s, 1H).

Compound 6-2: LCMS m/z (ESI): 636.3 (M+1). $^1$H NMR (400 MHz, CDCl$_3$): δ 8.61 (d, J=5.6 Hz, 1H), 7.88 (d, J=2.4 Hz, 1H), 7.77 (s, 1H), 7.74 (s, 1H), 7.50-7.79 (m, 5H), 7.44 (br s, 1H), 6.40 (d, J=7.2 Hz, 1H), 4.62 (s, 1H), 4.14-4.22 (m, 2H), 2.68-2.72 (m, 1H), 1.97-2.04 (m, 2H), 1.81-1.92 (m, 1H), 1.36 (t, J=7.2 Hz, 1H), 1.28-1.35 (m, 1H), 0.98 (d, J=6.8 Hz, 3H), 0.49 (br s, 1H).

Activity Assay
1. Screening Assay for Inhibitory Activity against Enzyme hFXIa (Human Factor XIa)
Experimental Objective:
To Test the Inhibitory Activity of the Compounds Disclosed herein Against Human Factor XIa
Experimental Materials:
1) Assay buffer, pH 7.4
100 mM Tris-HCl (Sigma, Cat. No.: T2663, Lot No.: SLBG2775)
200 mM NaCl (Sigma, Cat. No.: 13423, Lot No.: SZBB2360V)
0.02% tween20 (Sigma-P1379)

2) Enzyme and substrate
Enzyme: Human Factor XIa (Abcam, Cat No.: ab62411), total amount of 50 μg; dissolved in assay buffer and packaged.
Substrate: S-2366 (DiaPharma, Cat. No.: S821090), 25 mg 3) Instruments and consumables
SpectraMax 340PC multifunctional microplate reader (Molecular Devices)
384-well black transparent reaction plate (Corning, Cat. No.: 3712)
Echo liquid workstation (Labcyte)
A 384-well polypropylene compound plate (Labcyte-P-05525) was used in Echo
A 384 shallow-well polypropylene compound plate (Labcyte-LP-0200, 2.5-12 μL) was used in Echo
Mutidrop automatic dispenser (Thermo Scientific)
Mutidrop consumables (Thermo Scientific-24073290)

4) Compounds
Test compounds were each dissolved in DMSO to prepare a 10 mM solution and stored in a nitrogen cabinet.
Experimental method:
1) Preparation for compounds
All test compounds were prepared using Echo, subjected to gradient dilution and transferred to a 384-well reaction plate at 100 nL. The reference compound and the test samples, with an initial concentration of 200 μM, were subjected to 3-fold dilution to get 10 concentrations (the final concentration was 1 μM). To high signal wells were added DMSO, and to low signal wells were added 100 μM reference compound. Reference can be made to the sample distribution for distributions of samples and control.

1) Preparation for enzyme human factor XIa
Enzyme human factor XIa was diluted to 0.5 μg/mL with assay buffer.
3) Preparation for substrate S-2306
S-2306 was prepared at a concentration of 1 mM using the assay buffer.
4) 10 μL of 0.5 μg/mL enzyme human factor XIa was added to the reaction plate using a Mutidrop automatic dispenser and the final concentration was 5 ng/well.
5) 10 μL of 1 mM S-2306 was added to the reaction plate using a Mutidrop automatic dispenser and the final concentration was 0.5 mM.
6) Centrifugation was performed at 1000 rpm for 10 s.
7) The reaction plate was incubated in SpectraMax 340PC at 37° C. for 10 min and the absorbance was measured at 405 nm.
8) Data were analyzed using GraphPad Prism 5.0.
% inhibition rate=100%×[1—(sample reading—mean of low signal wells)/(mean of high signal wells—mean of low signal wells)]
IC$_{50}$ was analyzed using 4-factor linear regression:
Y=Bottom+(Top−Bottom)/(1+10^((LogIC$_{50}$−X)*Hill Slope))
Y is % inhibition rate and X is the logarithm of the sample concentration.
Experimental results:
The data of inhibitory activity ICso of the compounds disclosed herein against enzyme hFXIa are shown in Table 1 below:

TABLE 1

| Compounds | hFXIa IC$_{50}$ (nM) |
|---|---|
| 1-2 | 3.9 |
| 1-4 | 34.07 |
| 2-1 | 3.39 |
| 2-2 | 10.69 |
| 3-1 | 3.81 |
| 4-1 | 21.73 |
| 5-1 | 8.22 |
| 6-2 | 20.37 |

Conclusion: The compounds disclosed herein exhibit good inhibitory activity against enzyme hFXIa.

2. Testing of Human Plasma in vitro aPTT (Activated Partial Thromboplastin Time)

Experimental objective:

To test the anticoagulant effect of the compounds disclosed herein against human plasma in vitro Experimental materials:

1) Plasma: fresh human venous blood was mixed well with 0.109 M sodium citrate at a ratio of 9:1, and then the mixture was centrifuged at 3000 rpm for 15 min. The upper plasma was collected and tested within 2-5 h.

2) Reagents: aPTT reagent (activated partial thromboplastin time kit, mindray), PT reagent (prothrombin time kit, mindray), and calcium chloride solution.

3) Instruments: coagulometer (Beijing Precil, C$_{2000}$-4).

Experimental detection:

Test compounds were each dissolved in DMSO to prepare a 10 mM stock solution. The plasma was serially diluted to 400 μM, 200 μM, 100 μM, 50 μM, 25 μM, 12.5 μM, 6.25 μM, 3.125 μM, 1.563 μM, 0.781 μM, 0.390 μM and 0.195 μM with the 10 mM stock solution of each compound, and the blank control was 100% DMSO. The reagents, plasma and compounds were placed at corresponding positions in a coagulometer to detect the aPTT and PT of the compounds.

Data processing:

The concentrations of compounds corresponding to aPTT$_{2x}$ and PT$_{2x}$ (i.e., aPTT and PT of 2-fold blank control) were calculated by Prism curve fitting and the results are shown in Table 2 below:

TABLE 2

| Compounds | aPTT$_{2x}$ (μM) |
|---|---|
| 1-2 | 0.87 |
| 2-1 | 0.65 |
| 3-1 | 1.37 |

Conclusion: The compounds disclosed herein exhibit obvious anticoagulation effect against human plasma in vitro.

3. Pharmacokinetics in Rats

Experimental objective:

To determine the pharmacokinetic parameters of the compounds disclosed herein in rats Experimental scheme:

1) Experimental drug: compound 1-2;

2) Experimental animals: 4 male SD rats aged 7-9 weeks, randomly divided into 2 groups, 2 rats for each group;

3) Drug preparation: a proper amount of the drug was weighed out and dissolved in a mixed solvent of DMAC: solutol:water=10:10:80 to prepare two solutions of 0.2 mg/mL and 0.5 mg/mL, respectively;

Experimental procedures:

Animals in group 1 were administered with the 0.2 mg/mL drug at a dose of 0.5 mg/kg by single injection via the tail vein, and animals in group 2 were administered with the 0.5 mg/mL compound at a dose of 3 mg/kg by gavage. Animal plasma samples were collected 0.0833 (only the tail vein injection group), 0.25, 0.5, 1, 2, 4, 6, 8 and 24 h after administration. The drug concentration in plasma samples was determined using LC-MS/MS method, and the kinetic parameters of the test drug are shown in Table 3:

TABLE 3

Compound 1-2

Tail vein injection group

| Clearance Cl (mL/Kg/min) | Initial concentration C$_0$ (nM) | Volume of distribution Vd (L/Kg) | Half life T$_{1/2}$ (h) | Area under curve AUC (nM · h) |
|---|---|---|---|---|
| 5.65 | 1797 | 0.533 | 1.04 | 2339 |

Gavage administration group

| Peak concentration C$_{max}$ (nM) | Time of peak concentration T$_{1/2}$(h) | Area under curve AUC (nM · h) | Bioavailability F (%) | |
|---|---|---|---|---|
| 986 | 3 | 5205 | 37.1 | — |

— represents absence

Conclusion: The compound disclosed herein exhibits good pharmacokinetic properties in rats.

What is claimed is:

1. A compound of formula (I), an isomer thereof or a pharmaceutically acceptable salt thereof,

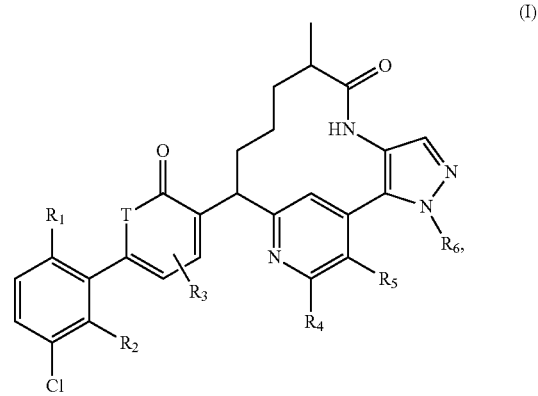

wherein,

T is —O— or —N(R$_a$)—;

R$_a$ is H or C$_{1-3}$ alkyl;

R$_1$ is triazolyl or tetrazolyl, wherein the triazolyl and tetrazolyl are optionally substituted with R$_b$;

R$_2$ is H or F;

R$_3$ is H, F, Cl, Br, CN, C$_{1-6}$ alkyl, C$_{1-6}$ alkoxy or C$_{1-6}$ alkylamino;

R$_4$ and R$_5$ are each independently H, F, Cl, Br, I, C$_{1-3}$ alkyl, C$_{1-3}$ haloalkyl or C$_{1-3}$ alkoxy;

R$_6$ is C$_{1-3}$ alkyl optionally substituted with 1, 2 or 3 R$_c$;

$R_b$ and $R_c$ are each independently F, Cl, Br, I, $C_{1-3}$ alkyl, $C_{1-3}$ haloalkyl, $C_{1-3}$ alkoxy or $C_{3-4}$ cycloalkyl.

2. The compound, the isomer thereof or the pharmaceutically acceptable salt thereof according to claim 1, wherein the compound has a structure shown as formula (I-1) or (I-2):

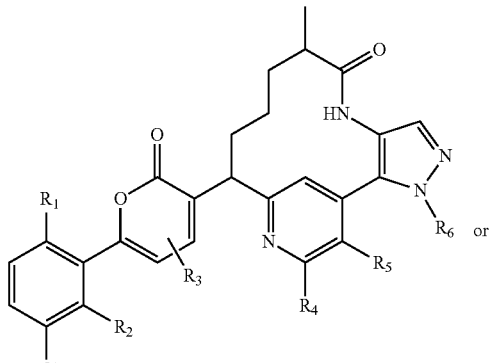
(I-1)

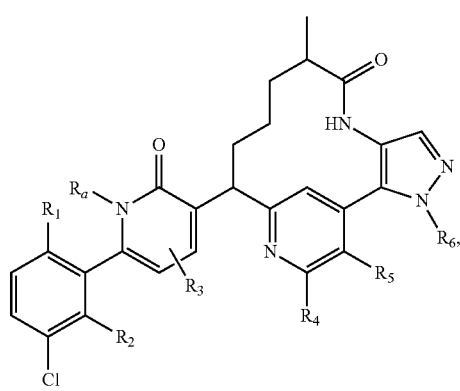
(I-2)

wherein $R_1$, $R_2$, $R_3$, $R_4$, $R_5$, $R_6$ and $R_a$ are as defined in claim 1.

3. The compound, the isomer thereof or the pharmaceutically acceptable salt thereof according to claim 2, wherein the compound has a structure shown as formula (I-1-a) or (I-2-a):

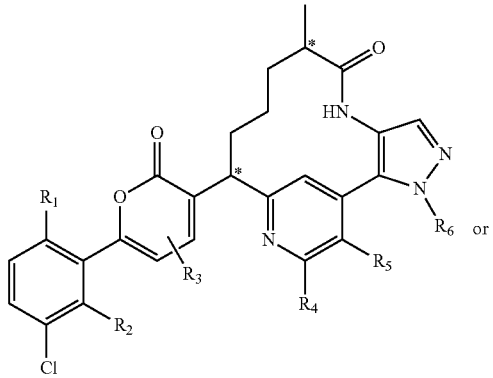
(I-1-a)

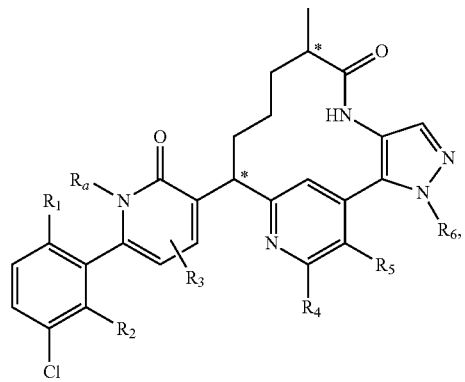
(I-2-a)

wherein the carbon atom with "*" is a chiral carbon atom present in a form of a single (R) or (S) enantiomer or in a form enriched with one enantiomer;

$R_1$, $R_2$, $R_3$, $R_4$, $R_5$, $R_6$ and $R_a$ are as defined in claim 2.

4. The compound, the isomer thereof or the pharmaceutically acceptable salt thereof according to claim 3, wherein the compound has a structure shown as formula (I-1-b) or (I-2-b):

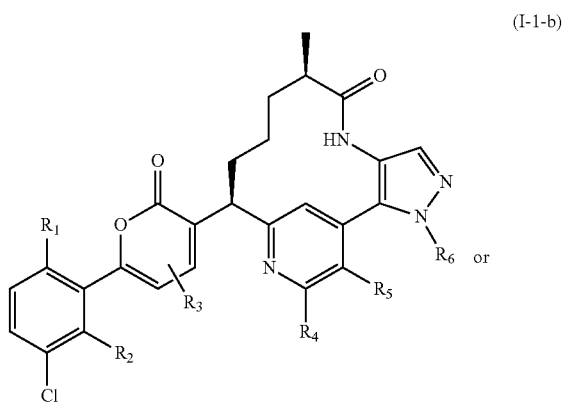
(I-1-b)

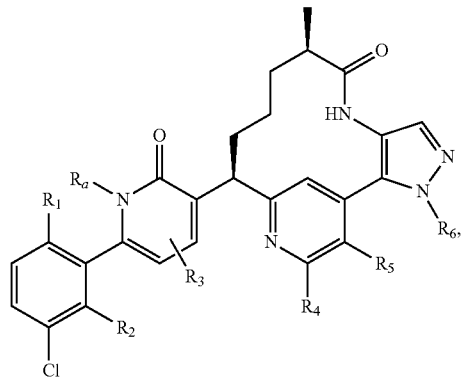
(I-2-b)

wherein $R_1$, $R_2$, $R_3$, $R_4$, $R_5$, $R_6$ and $R_a$ are as defined in claim 3.

5. The compound, the isomer thereof or the pharmaceutically acceptable salt thereof according to claim 1, wherein $R_a$ is H, —$CH_3$ or —$CH_2CH_3$.

6. The compound, the isomer thereof or the pharmaceutically acceptable salt thereof according to claim 1, wherein T is —O—, —NH— or —N($CH_3$)—;

or, $R_1$ is

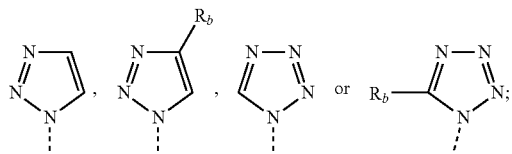

or, $R_3$ is H, F, Cl, Br, CN, $C_{1-3}$ alkyl, $C_{1-3}$ alkoxy or $C_{1-3}$ alkylamino;

or, $R_4$ and $R_5$ are each independently H, F, Cl, Br, I,

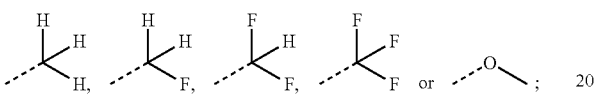

or, $R_6$ is —$CH_3$ optionally substituted with 1, 2 or 3 $R_c$.

7. The compound, the isomer thereof or the pharmaceutically acceptable salt thereof according to claim 1, wherein $R_b$ and $R_c$ are each independently F, Cl, methyl, —$CHF_2$, ethoxy or cyclopropyl.

8. The compound, the isomer thereof or the pharmaceutically acceptable salt thereof according to claim 1, wherein $R_1$ is

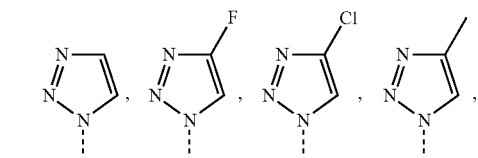

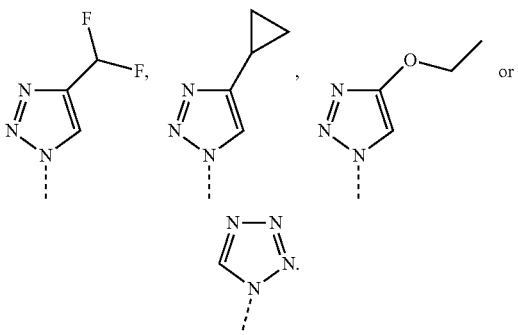

9. The compound, the isomer thereof or the pharmaceutically acceptable salt thereof according to claim 1, wherein $R_3$ is H, F, Cl, Br, CN, —$CH_3$, —$OCH_3$,

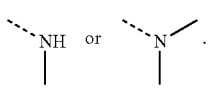

10. The compound, the isomer thereof or the pharmaceutically acceptable salt thereof according to claim 1, wherein $R_6$ is

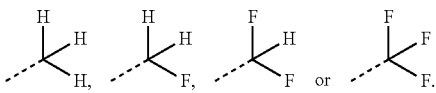

11. The compound, the isomer thereof or the pharmaceutically acceptable salt thereof according to claim 1, wherein

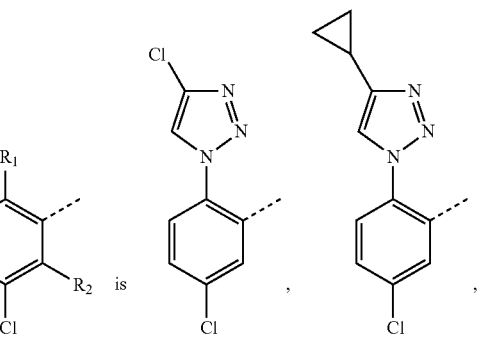

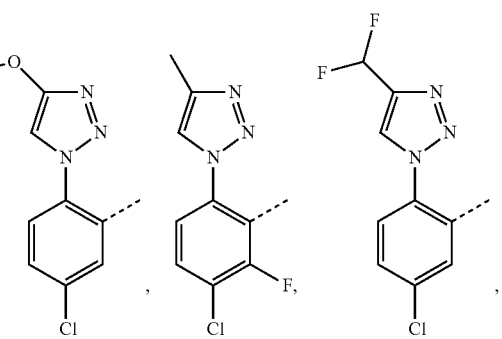

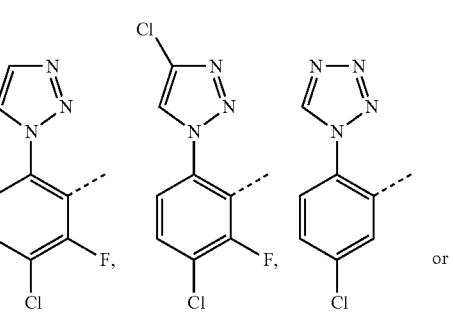

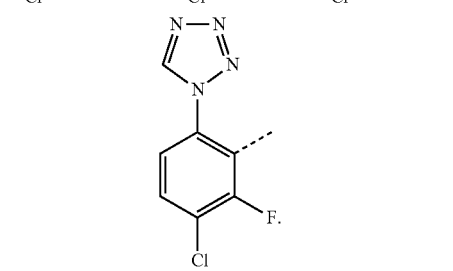

12. The compound, the isomer thereof or the pharmaceutically acceptable salt thereof according to claim 1, wherein

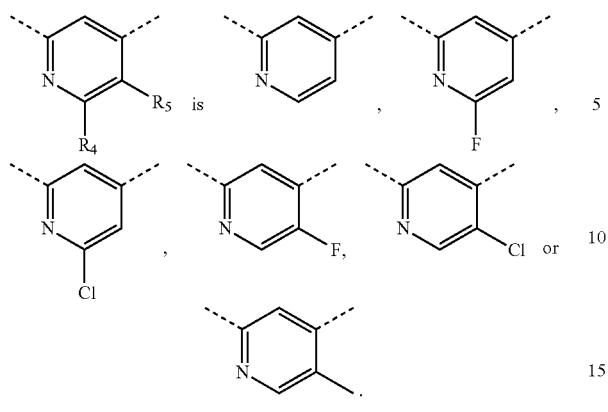

is

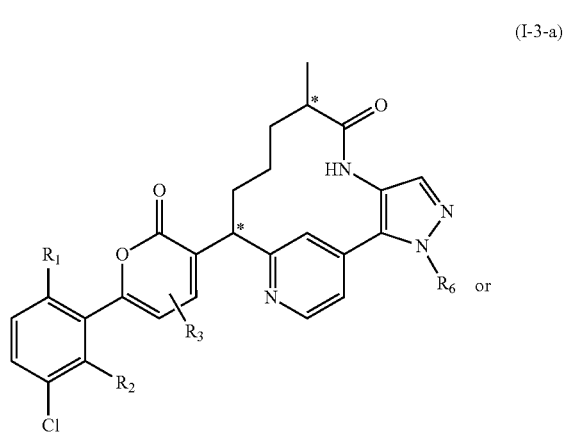

13. The compound, the isomer thereof or the pharmaceutically acceptable salt thereof according to claim 1, wherein the compound has a structure shown as formula (I-3) or (I-4):

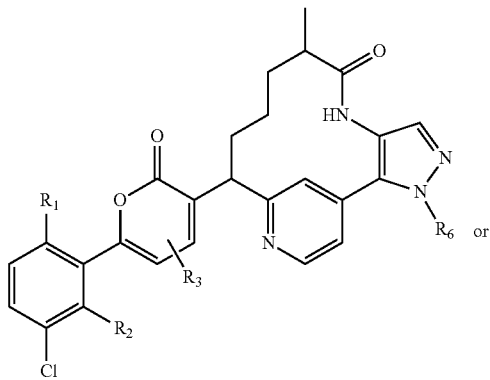

(I-3)

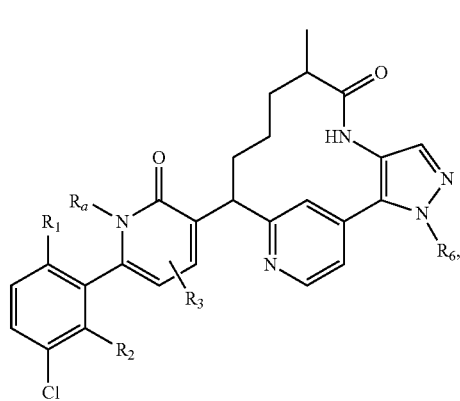

(I-4)

wherein $R_1$ is as defined in claim 1; $R_2$ is as defined in claim 1; $R_3$ is as defined in claim 1; $R_6$ is as defined in claim 1; $R_a$ is as defined in claim 1.

14. The compound, the isomer thereof or the pharmaceutically acceptable salt thereof according to claim 13, wherein the compound has a structure shown as formula (1-3-a) or (1-4-a):

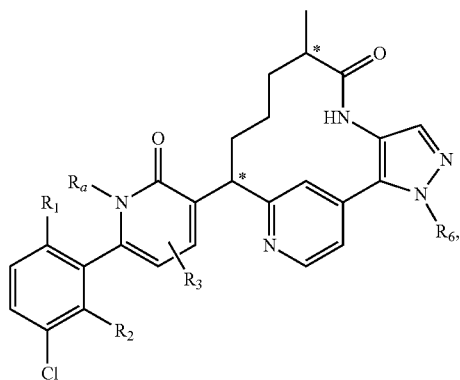

(I-3-a)

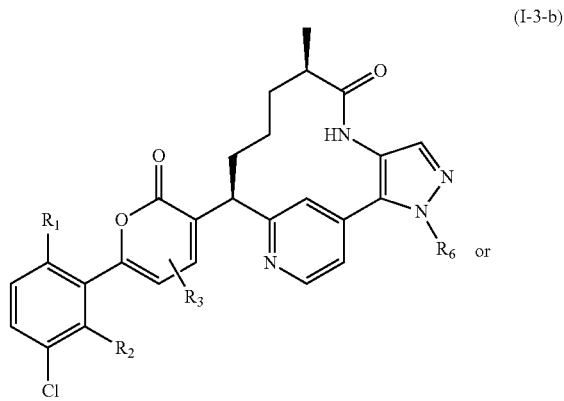

(I-4-a)

wherein the carbon atom with "*" is a chiral carbon atom present in a form of a single (R) or (S) enantiomer or in a form enriched with one enantiomer;

$R_1$, $R_2$, $R_3$, $R_a$ and $R_6$ are as defined in claim 13.

15. The compound, the isomer thereof or the pharmaceutically acceptable salt thereof according to claim 14, wherein the compound has a structure shown as formula (I-3-b) or (1-4-b):

(I-3-b)

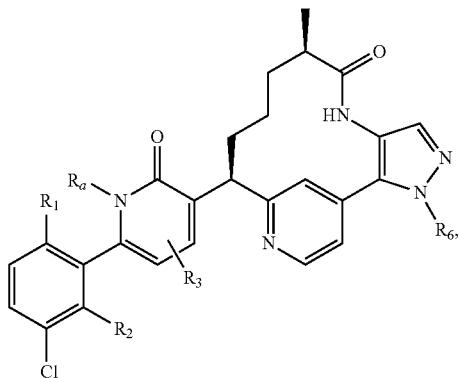

(I-4-b)

wherein R₁, R₂, R₃, Rₐ and R₆ are as defined in claim 14.

16. The compound, the isomer thereof or the pharmaceutically acceptable salt thereof according to claim 1, wherein the compound has a structure shown as formula (I-5) or (I-6):

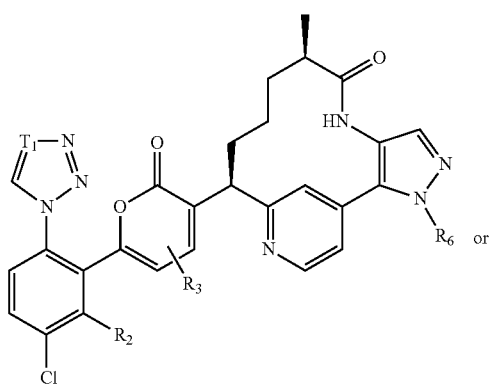

(I-5)

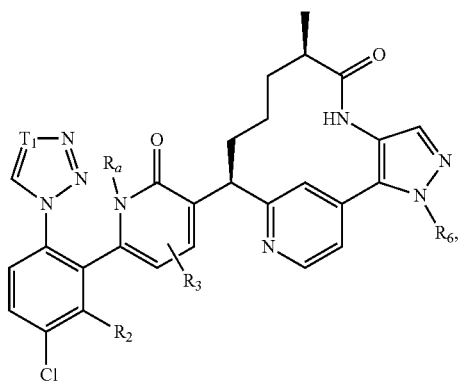

(I-6)

wherein R₂, Rₐ and R₆ are as defined in claim 1, T₁ is N or CR_b, and R_b is as defined in claim 1.

17. A compound, an isomer thereof or a pharmaceutically acceptable salt thereof, wherein the compound is

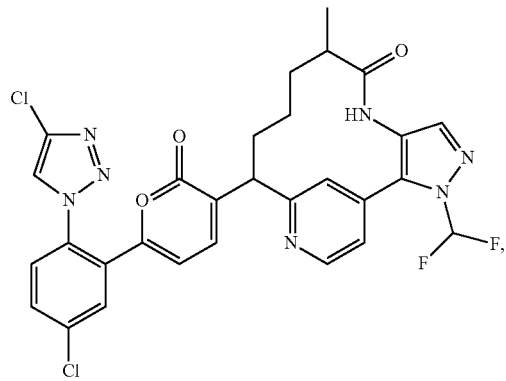

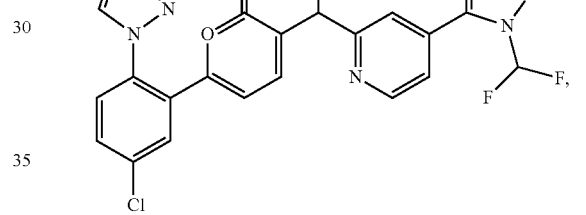

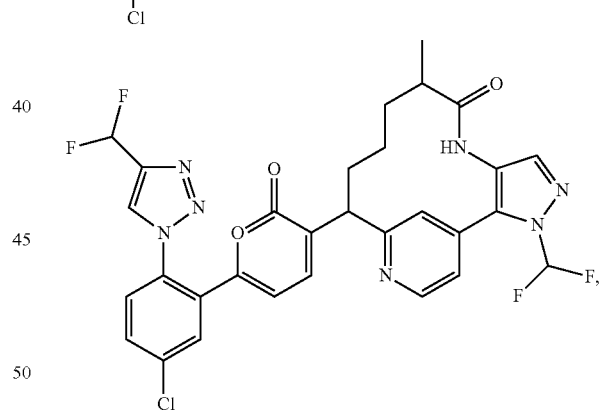

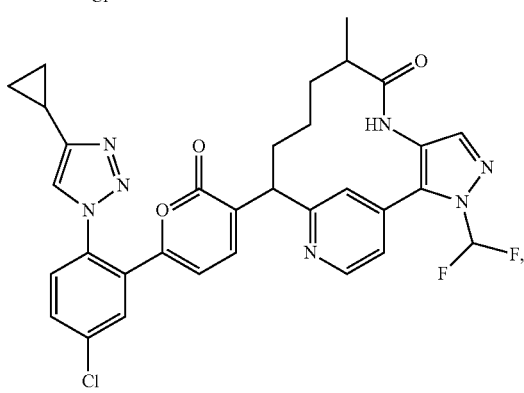

71
-continued
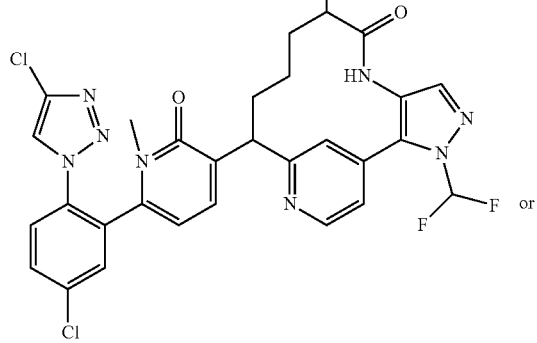
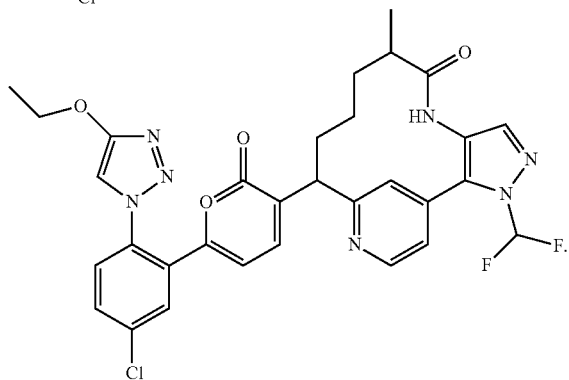
18. A compound, an isomer thereof or a pharmaceutically acceptable salt thereof, wherein the compound is
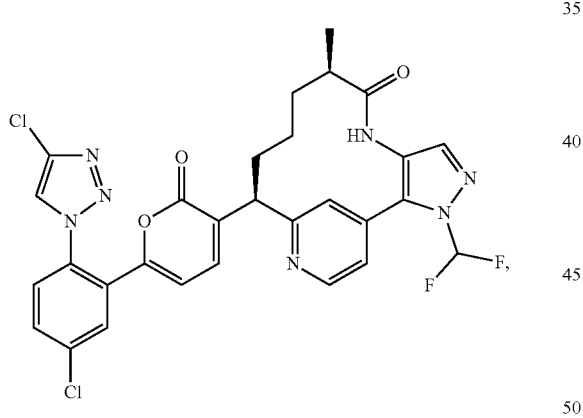
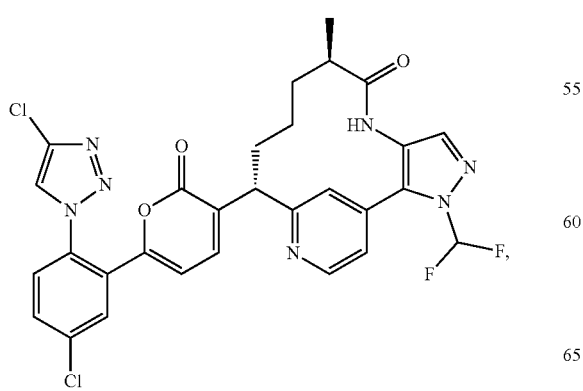
72
-continued
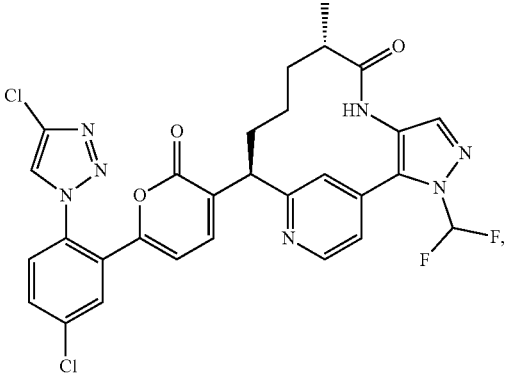
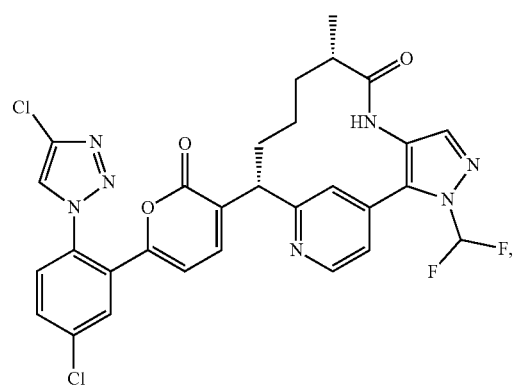
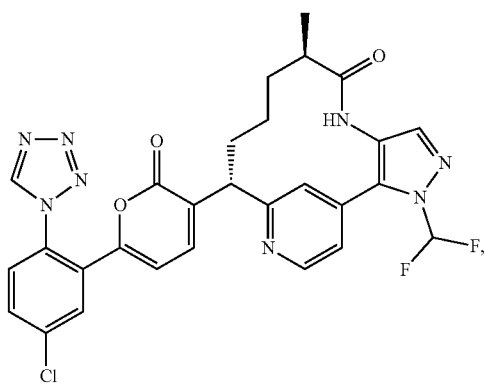

73
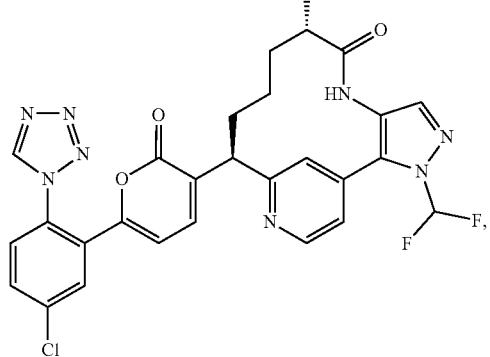
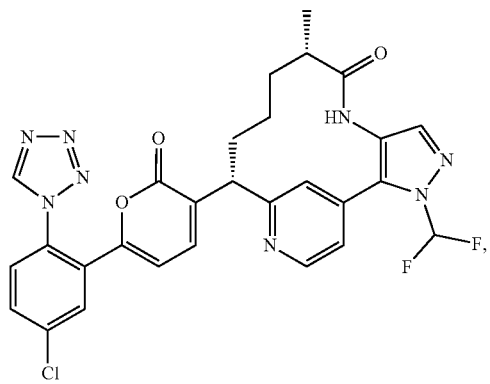
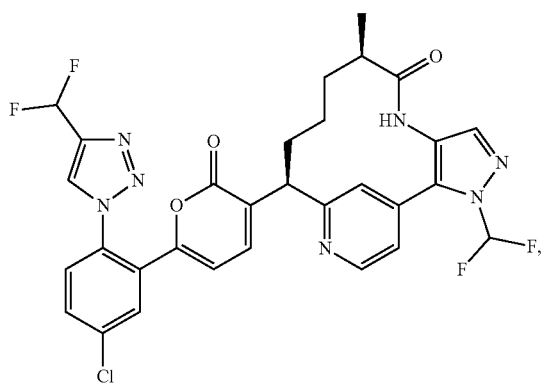
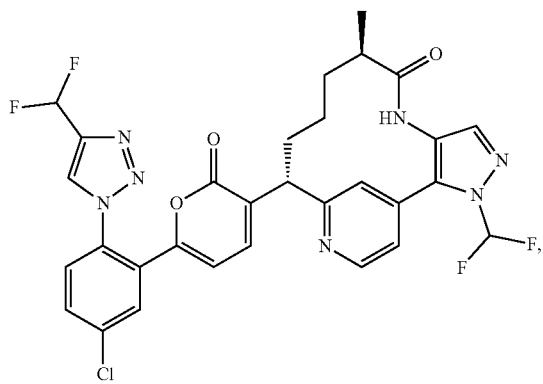
74
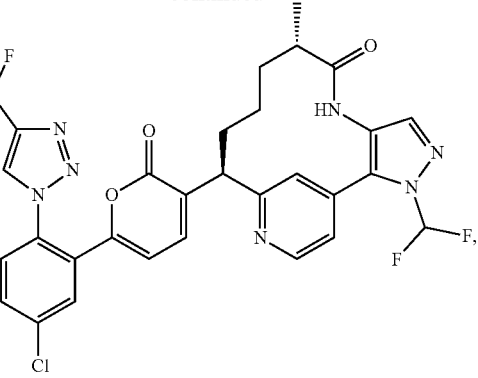
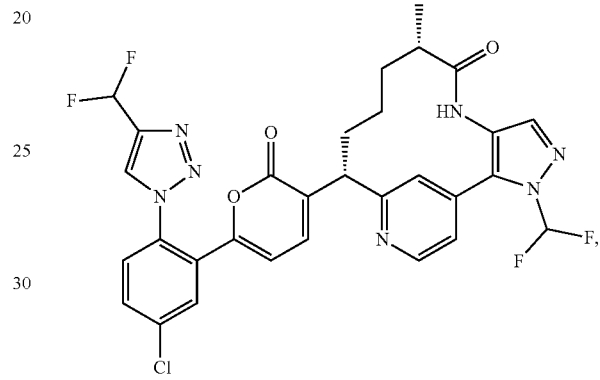
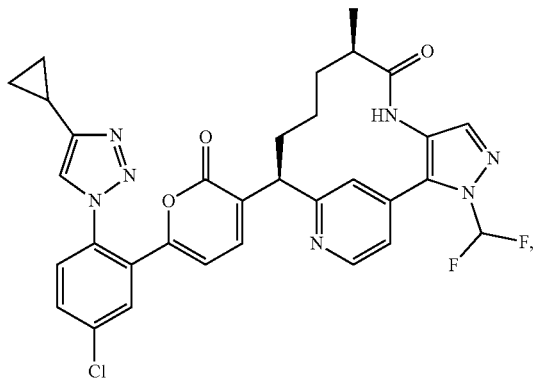
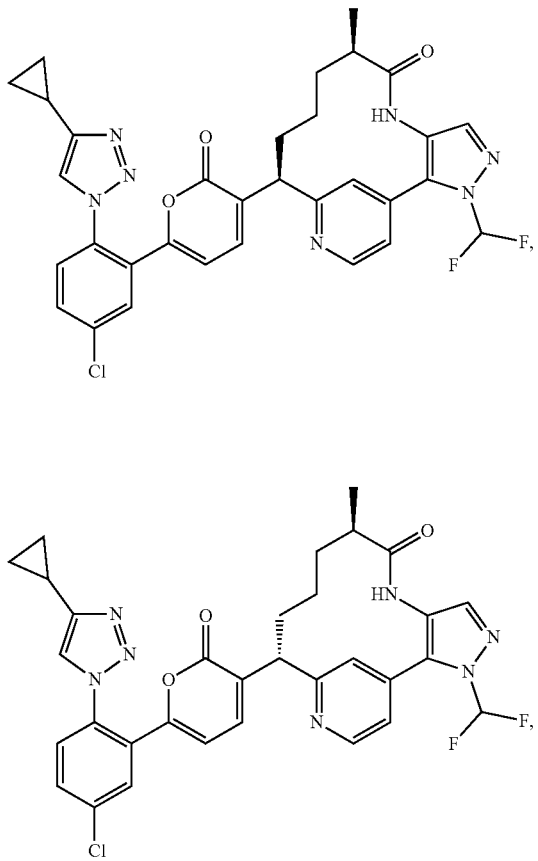

75
-continued
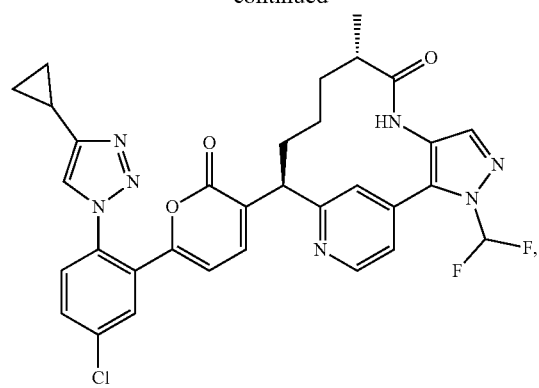
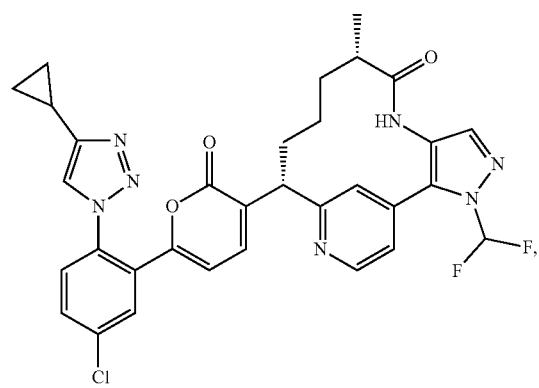
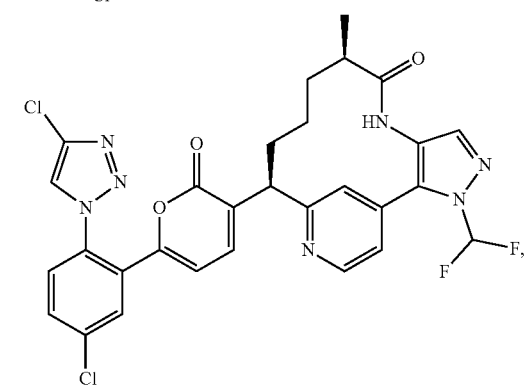
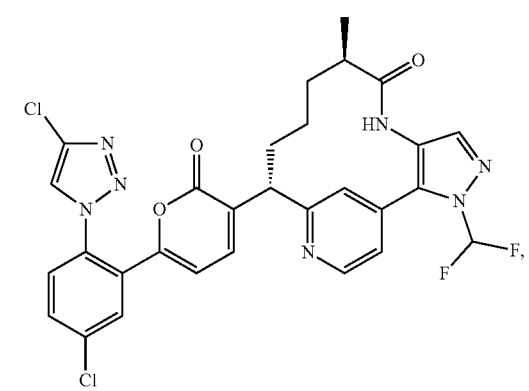
76
-continued
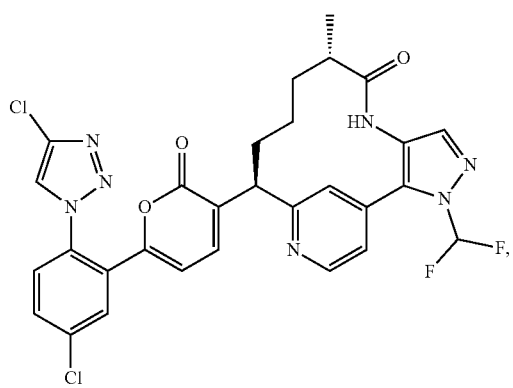
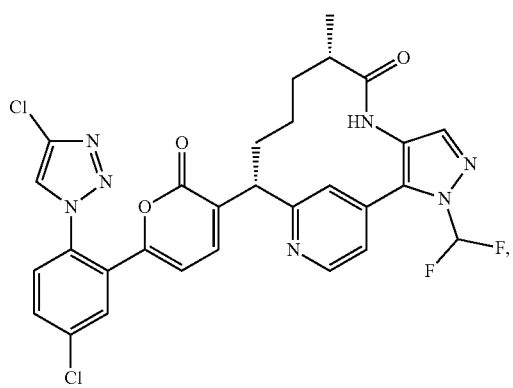
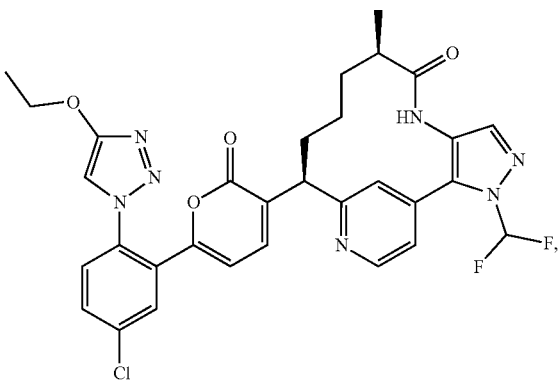

77
-continued

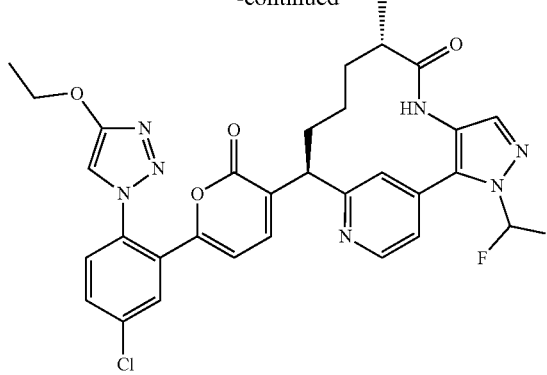

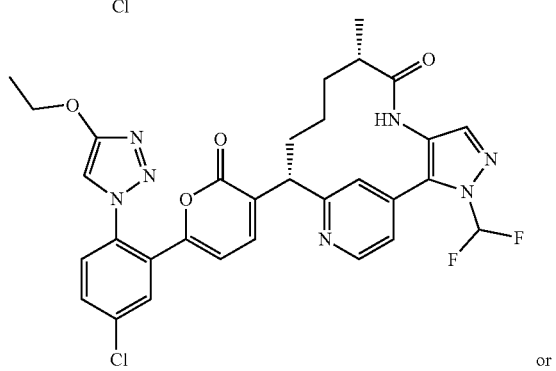

or

78
-continued

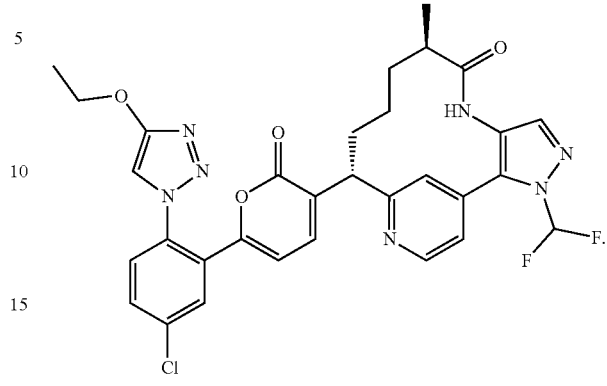

19. A pharmaceutical composition comprising a therapeutically effective amount of the compound, the isomer thereof or the pharmaceutically acceptable salt thereof according to claim 1 and a pharmaceutically acceptable carrier.

20. A method of inhibiting factor XIa in a subject in need thereof, comprising administering the compound, the isomer thereof or the pharmaceutically acceptable salt thereof according to claim 1 to the subject.

* * * * *